United States Patent
Miller et al.

(10) Patent No.: US 9,333,204 B2
(45) Date of Patent: May 10, 2016

(54) SOLID ANTIVIRAL DOSAGE FORMS

(71) Applicants: AbbVie Inc., North Chicago, IL (US); AbbVie Deutschland GmbH & Co. KG, Wiesbaden (DE)

(72) Inventors: Jonathan M. Miller, Lindenhurst, ID (US); John B. Morris, Grayslake, IL (US); Nancy E. Sever, Northbrook, IL (US); Eric A. Schmitt, Libertyville, IL (US); Ping X. Gao, Highland Park, IL (US); Yi Shi, Libertyville, IL (US); Yi Gao, Vernon Hills, IL (US); Bernd Liepold, Dossenheim (DE); Anna Moosmann, Winterbach (DE); Mirko Pauli, Ludwigshafen (DE); Fatih Durak, Ludwigshafen (DE); Thomas Kessler, Schifferstadt (DE); Peter A. Hoelig, Waechtersbach (DE); Karin Rosenblatt, Mannheim (DE); Drazen Kostelac, Mannheim (DE); Rajeev Gokhale, Singapore (SG); Mark Costello, Chicago, IL (US); Carl Knable, Elmhurst, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 14/677,611

(22) Filed: Apr. 2, 2015

(65) Prior Publication Data

US 2015/0258093 A1  Sep. 17, 2015

Related U.S. Application Data

(63) Continuation of application No. PCT/US2015/010060, filed on Jan. 2, 2015.

(60) Provisional application No. 61/976,934, filed on Apr. 8, 2014, provisional application No. 61/923,544, filed on Jan. 3, 2014.

(51) Int. Cl.

| | |
|---|---|
| *A61K 31/4965* | (2006.01) |
| *A01N 43/54* | (2006.01) |
| *A01N 43/36* | (2006.01) |
| *A61K 31/513* | (2006.01) |
| *A61K 47/32* | (2006.01) |
| *A61K 47/38* | (2006.01) |
| *A61K 9/24* | (2006.01) |
| *A61K 31/4025* | (2006.01) |
| *A61K 31/427* | (2006.01) |
| *A61K 31/497* | (2006.01) |

(52) U.S. Cl.
CPC .............. *A61K 31/513* (2013.01); *A61K 9/209* (2013.01); *A61K 31/4025* (2013.01); *A61K 31/427* (2013.01); *A61K 31/497* (2013.01); *A61K 47/32* (2013.01); *A61K 47/38* (2013.01); *A61K 2300/00* (2013.01)

(58) Field of Classification Search
CPC ............ A61K 31/513; A61K 31/4025; A61K 31/427; A61K 31/497
USPC ...................... 514/255.05, 274, 422
See application file for complete search history.

(56) References Cited

U.S. PATENT DOCUMENTS

| | | |
|---|---|---|
| 5,541,206 A | 7/1996 | Kempf et al. |
| 5,830,867 A | 11/1998 | Bhatnagar et al. |
| 5,831,002 A | 11/1998 | Haupt et al. |
| 5,935,982 A | 8/1999 | Dykstra et al. |
| 6,042,847 A | 3/2000 | Kerc et al. |
| 6,235,493 B1 | 5/2001 | Bissell et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,369,091 B1 | 4/2002 | Sircar et al. |
| 6,388,093 B1 | 5/2002 | Chamberlain et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,599,528 B1 | 7/2003 | Rosenberg et al. |
| 6,608,027 B1 | 8/2003 | Tsantrizos et al. |
| 6,642,204 B2 | 11/2003 | Llinas-Brunet et al. |
| 6,653,295 B2 | 11/2003 | Glunz et al. |
| 6,699,855 B2 | 3/2004 | Zhang et al. |
| 6,703,403 B2 | 3/2004 | Norbeck et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,803,374 B2 | 10/2004 | Priestley et al. |
| 6,846,802 B2 | 1/2005 | Chen et al. |
| 6,846,806 B2 | 1/2005 | Priestley |
| 6,867,185 B2 | 3/2005 | Campbell et al. |

(Continued)

FOREIGN PATENT DOCUMENTS

| | | |
|---|---|---|
| BR | PI0401908 A | 1/2006 |
| DE | 75755 C | 6/1894 |

(Continued)

OTHER PUBLICATIONS

Chiou et al., "Pharmaceutical applications of solid dispersion systems," J. Pharm. Sci., 60(9): 1281-1302 (1971).
Food and Drug Administration Guidance for Industry, SUPAC-IR/MR• Immediate Release and Modified Release Solid Oral Dosage Forms, Manufacturing Equipment Addendum, Jan. 1999, CMC 9, Revision 1, (44 pages).
Masters, K., Spray Drying Handbook, Halstead Press, New York, 4th ed., 1985 (Table of Contents only, 7 pages).
Written Opinion from PCT/US2015/010060, dated Mar. 27, 2015 (6 pages).
International Search Report from PCT/US2015/010060, dated Mar. 27, 2015 (6 pages).
International Search Report for Application No. PCT/US2011/065486, mailed on Mar. 26, 2012, 3 pages.

(Continued)

*Primary Examiner* — San-Ming Hui

(57) ABSTRACT

The present disclosure relates to solid dosage forms comprising antiviral compounds and methods of using such dosage forms to treat antiviral infection.

15 Claims, No Drawings

(56) References Cited

U.S. PATENT DOCUMENTS

| | | | |
|---|---|---|---|
| 6,869,964 B2 | 3/2005 | Campbell et al. | |
| 6,872,805 B2 | 3/2005 | Campbell et al. | |
| 6,878,722 B2 | 4/2005 | Campbell et al. | |
| 6,881,741 B2 | 4/2005 | Chan Chun Kong et al. | |
| 6,919,366 B2 | 7/2005 | Sircar et al. | |
| 6,923,988 B2 | 8/2005 | Patel et al. | |
| 6,939,854 B2 | 9/2005 | Priestley | |
| 6,995,174 B2 | 2/2006 | Wang et al. | |
| 7,037,911 B2 | 5/2006 | Zhang | |
| 7,041,698 B2 | 5/2006 | Ripka et al. | |
| 7,065,453 B1 | 6/2006 | Diller et al. | |
| 7,091,184 B2 | 8/2006 | Llinas-Brunet et al. | |
| 7,108,864 B1 | 9/2006 | Martino et al. | |
| 7,112,601 B2 | 9/2006 | Glunz et al. | |
| 7,119,072 B2 | 10/2006 | Llinas-Brunet et al. | |
| 7,122,627 B2 | 10/2006 | Priestley et al. | |
| 7,132,504 B2 | 11/2006 | Scola et al. | |
| 7,135,462 B2 | 11/2006 | Scola et al. | |
| 7,141,574 B2 | 11/2006 | Beaulieu et al. | |
| 7,153,848 B2 | 12/2006 | Hudyma et al. | |
| 7,157,424 B2 | 1/2007 | Chen et al. | |
| 7,173,004 B2 | 2/2007 | McPhee et al. | |
| 7,176,208 B2 | 2/2007 | Nakajima et al. | |
| 7,183,270 B2 | 2/2007 | Cherney et al. | |
| 7,183,302 B2 | 2/2007 | Romine et al. | |
| 7,189,844 B2 | 3/2007 | Gallou et al. | |
| 7,309,708 B2 | 12/2007 | Tu et al. | |
| 7,323,447 B2 | 1/2008 | Sin et al. | |
| 7,348,425 B2 | 3/2008 | Hudyma et al. | |
| 7,368,452 B2 | 5/2008 | Nakajima et al. | |
| 7,375,218 B2 | 5/2008 | Gallou | |
| 7,488,832 B2 | 2/2009 | Cole et al. | |
| 7,491,794 B2 | 2/2009 | Blatt et al. | |
| 7,504,378 B2 | 3/2009 | Llinas-Brunet et al. | |
| 7,544,798 B2 | 6/2009 | Busacca et al. | |
| 7,566,719 B2 | 7/2009 | Nakajima et al. | |
| 7,592,419 B2 | 9/2009 | Venkatraman et al. | |
| 7,601,709 B2 | 10/2009 | Miao et al. | |
| 7,608,590 B2 | 10/2009 | Rosenquist et al. | |
| 7,642,235 B2 | 1/2010 | Llinas-Brunet et al. | |
| 7,642,339 B2 | 1/2010 | Chaudhary et al. | |
| 7,659,245 B2 | 2/2010 | Simmen et al. | |
| 7,659,270 B2 | 2/2010 | Bachand et al. | |
| 7,687,459 B2 | 3/2010 | Niu et al. | |
| 7,704,992 B2 | 4/2010 | Bachand et al. | |
| 7,728,027 B2 | 6/2010 | Pack et al. | |
| 7,732,457 B2 | 6/2010 | Malamas et al. | |
| 7,741,281 B2 | 6/2010 | D'Andrea et al. | |
| 7,741,347 B2 | 6/2010 | Bachand et al. | |
| 7,745,636 B2 | 6/2010 | Bachand et al. | |
| 7,759,495 B2 | 7/2010 | Bachand et al. | |
| 7,763,584 B2 | 7/2010 | Wang et al. | |
| 7,763,731 B2 | 7/2010 | Rockway et al. | |
| 7,772,180 B2 | 8/2010 | Sin et al. | |
| 7,772,183 B2 | 8/2010 | Carini et al. | |
| 7,829,665 B2 | 11/2010 | Blatt et al. | |
| 7,838,711 B2 | 11/2010 | Herweck et al. | |
| 7,906,655 B2 | 3/2011 | Belema et al. | |
| 8,025,899 B2 | 9/2011 | Berndl et al. | |
| 8,101,643 B2 | 1/2012 | Qiu et al. | |
| 8,202,912 B2 | 6/2012 | Curatolo et al. | |
| 8,268,349 B2 | 9/2012 | Rosenberg et al. | |
| 8,415,315 B2 * | 4/2013 | Chakrabarti | C12N 9/12 514/44 A |
| 8,476,225 B2 | 7/2013 | Casarez et al. | |
| 8,501,238 B2 * | 8/2013 | Flentge | C07D 239/22 424/489 |
| 8,642,538 B2 * | 2/2014 | Ku | C07K 1/113 514/4.3 |
| 8,691,938 B2 * | 4/2014 | DeGoey | C07D 401/14 514/4.3 |
| 2002/0016442 A1 | 2/2002 | Llinas-Brunet et al. | |
| 2002/0037998 A1 | 3/2002 | Llinas-Brunet et al. | |
| 2002/0111313 A1 | 8/2002 | Campbell et al. | |
| 2002/0183319 A1 | 12/2002 | Liang et al. | |
| 2003/0004203 A1 | 1/2003 | Sircar et al. | |
| 2003/0100582 A1 | 5/2003 | Sircar et al. | |
| 2003/0181363 A1 | 9/2003 | Llinas-Brunet et al. | |
| 2003/0186895 A1 | 10/2003 | Llinas-Brunet et al. | |
| 2003/0187018 A1 | 10/2003 | Llinas-Brunet et al. | |
| 2003/0191067 A1 | 10/2003 | Llinas-Brunet et al. | |
| 2003/0195228 A1 | 10/2003 | Chen et al. | |
| 2003/0224977 A1 | 12/2003 | Llinas-Brunet et al. | |
| 2003/0232386 A1 | 12/2003 | Shah et al. | |
| 2004/0002448 A1 | 1/2004 | Tsantrizos et al. | |
| 2004/0013697 A1 | 1/2004 | Berndl et al. | |
| 2004/0038872 A1 | 2/2004 | Campbell et al. | |
| 2004/0048802 A1 | 3/2004 | Ripka et al. | |
| 2004/0058982 A1 | 3/2004 | Harris | |
| 2004/0072243 A1 | 4/2004 | Sands et al. | |
| 2004/0106559 A1 | 6/2004 | Wang et al. | |
| 2004/0180815 A1 | 9/2004 | Nakajima et al. | |
| 2004/0229776 A1 | 11/2004 | Chen et al. | |
| 2004/0229777 A1 | 11/2004 | Cerreta et al. | |
| 2004/0229818 A1 | 11/2004 | Llinas-Brunet | |
| 2004/0248779 A1 | 12/2004 | Dersch et al. | |
| 2004/0248806 A1 | 12/2004 | Temsamani et al. | |
| 2004/0266668 A1 | 12/2004 | Nakajima et al. | |
| 2005/0020503 A1 | 1/2005 | Llinas-Brunet et al. | |
| 2005/0049187 A1 | 3/2005 | Brandenburg et al. | |
| 2005/0075279 A1 | 4/2005 | Llinas-Brunet et al. | |
| 2005/0075343 A1 | 4/2005 | Sircar et al. | |
| 2005/0080005 A1 | 4/2005 | Llinas-Brunet et al. | |
| 2005/0084529 A1 | 4/2005 | Rosenberg et al. | |
| 2005/0090432 A1 | 4/2005 | McPhee et al. | |
| 2005/0119168 A1 | 6/2005 | Venkatraman et al. | |
| 2005/0143316 A1 | 6/2005 | Tu et al. | |
| 2005/0148085 A1 | 7/2005 | Larsen | |
| 2005/0153877 A1 | 7/2005 | Miao et al. | |
| 2005/0153900 A1 | 7/2005 | Velazquez et al. | |
| 2005/0164921 A1 | 7/2005 | Njoroge et al. | |
| 2005/0192212 A1 | 9/2005 | Llinas-Brunet et al. | |
| 2005/0197375 A1 | 9/2005 | Sircar et al. | |
| 2005/0209135 A1 | 9/2005 | Busacca et al. | |
| 2005/0214366 A1 | 9/2005 | Harris | |
| 2005/0215423 A1 | 9/2005 | Brenner et al. | |
| 2005/0222045 A1 | 10/2005 | Auvin et al. | |
| 2005/0267018 A1 | 12/2005 | Blatt et al. | |
| 2005/0267151 A1 | 12/2005 | Busacca et al. | |
| 2006/0003942 A1 | 1/2006 | Tung et al. | |
| 2006/0009667 A1 | 1/2006 | Herweck et al. | |
| 2006/0019905 A1 | 1/2006 | Bailey et al. | |
| 2006/0046965 A1 | 3/2006 | Bailey et al. | |
| 2006/0052602 A1 | 3/2006 | Kim et al. | |
| 2006/0058317 A1 | 3/2006 | Gravestock et al. | |
| 2006/0063915 A1 | 3/2006 | Gallou et al. | |
| 2006/0063916 A1 | 3/2006 | Gallou | |
| 2006/0068007 A1 | 3/2006 | Li et al. | |
| 2006/0089300 A1 | 4/2006 | Llinas-Brunet et al. | |
| 2006/0105997 A1 | 5/2006 | Arrington et al. | |
| 2006/0122123 A1 | 6/2006 | Chaudhary et al. | |
| 2006/0166893 A1 | 7/2006 | Auvin et al. | |
| 2006/0172950 A1 | 8/2006 | Wang et al. | |
| 2006/0199773 A1 | 9/2006 | Sausker et al. | |
| 2006/0205638 A1 | 9/2006 | Busacca et al. | |
| 2006/0257980 A1 | 11/2006 | Li | |
| 2006/0258868 A1 | 11/2006 | Bailey et al. | |
| 2006/0275366 A1 | 12/2006 | Malcolm et al. | |
| 2006/0276405 A1 | 12/2006 | Albrecht | |
| 2006/0276407 A1 | 12/2006 | Albrecht et al. | |
| 2006/0281688 A1 | 12/2006 | Zhang et al. | |
| 2007/0004635 A1 | 1/2007 | Albrecht et al. | |
| 2007/0004741 A1 | 1/2007 | Apodaca et al. | |
| 2007/0010431 A1 | 1/2007 | Malcolm et al. | |
| 2007/0010455 A1 | 1/2007 | Hewawasam et al. | |
| 2007/0060510 A1 | 3/2007 | Nakajima et al. | |
| 2007/0060565 A1 | 3/2007 | Meanwell et al. | |
| 2007/0072809 A1 | 3/2007 | Cho et al. | |
| 2007/0078081 A1 | 4/2007 | Casarez et al. | |
| 2007/0078122 A1 | 4/2007 | Bergstrom et al. | |
| 2007/0093414 A1 | 4/2007 | Carini et al. | |
| 2007/0099825 A1 | 5/2007 | D'Andrea et al. | |
| 2007/0142434 A1 | 6/2007 | Sandanayaka et al. | |
| 2007/0161575 A1 | 7/2007 | Miao et al. | |

(56) References Cited

U.S. PATENT DOCUMENTS

| | | |
|---|---|---|
| 2007/0179167 A1 | 8/2007 | Cottrell et al. |
| 2007/0184024 A1 | 8/2007 | Meanwell et al. |
| 2007/0185083 A1 | 8/2007 | Bergstrom et al. |
| 2007/0197558 A1 | 8/2007 | Betebenner et al. |
| 2007/0232627 A1 | 10/2007 | Betebenner et al. |
| 2007/0232645 A1 | 10/2007 | Rockway et al. |
| 2007/0237818 A1 | 10/2007 | Malcolm et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0281884 A1 | 12/2007 | Sun et al. |
| 2007/0281885 A1 | 12/2007 | Sun et al. |
| 2007/0287664 A1 | 12/2007 | Ralston et al. |
| 2007/0287694 A1 | 12/2007 | Yeung et al. |
| 2007/0299068 A1 | 12/2007 | Karp et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0044379 A1 | 2/2008 | Bachand et al. |
| 2008/0044380 A1 | 2/2008 | Bachand et al. |
| 2008/0045536 A1 | 2/2008 | Vaccaro et al. |
| 2008/0050336 A1 | 2/2008 | Bachand et al. |
| 2008/0075696 A1 | 3/2008 | Parsons et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0145334 A1 | 6/2008 | Wang et al. |
| 2008/0146537 A1 | 6/2008 | Bender et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0171015 A1 | 7/2008 | Bender et al. |
| 2008/0181868 A1 | 7/2008 | Sun et al. |
| 2008/0188494 A1 | 8/2008 | Dietz et al. |
| 2008/0200497 A1 | 8/2008 | Bailey et al. |
| 2008/0221107 A1 | 9/2008 | Giordanetto et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz |
| 2008/0279821 A1 | 11/2008 | Niu et al. |
| 2008/0299075 A1 | 12/2008 | Bachand et al. |
| 2008/0311075 A1 | 12/2008 | Bachand et al. |
| 2008/0311077 A1 | 12/2008 | Chaudhary et al. |
| 2009/0004111 A1 | 1/2009 | Rice et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041716 A1 | 2/2009 | Kim et al. |
| 2009/0041721 A1 | 2/2009 | Niu et al. |
| 2009/0043107 A1 | 2/2009 | Pack et al. |
| 2009/0047252 A1 | 2/2009 | Cai et al. |
| 2009/0068140 A1 | 3/2009 | Bachand et al. |
| 2009/0075869 A1 | 3/2009 | Holloway et al. |
| 2009/0093456 A1 | 4/2009 | Arnold et al. |
| 2009/0093533 A1 | 4/2009 | Beigelman et al. |
| 2009/0104151 A1 | 4/2009 | Hanson et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0162318 A1 | 6/2009 | Bender et al. |
| 2009/0163706 A1 | 6/2009 | Hildbrand et al. |
| 2009/0169510 A1 | 7/2009 | Blatt et al. |
| 2009/0175822 A1 | 7/2009 | Moore et al. |
| 2009/0176858 A1 | 7/2009 | Niu et al. |
| 2009/0180981 A1 | 7/2009 | Niu et al. |
| 2009/0186869 A1 | 7/2009 | Cottell et al. |
| 2009/0191153 A1 | 7/2009 | Sun et al. |
| 2009/0202478 A1 | 8/2009 | Bachand et al. |
| 2009/0202480 A1 | 8/2009 | Parsy et al. |
| 2009/0202483 A1 | 8/2009 | Bachand et al. |
| 2009/0257978 A1 | 10/2009 | Cho et al. |
| 2009/0269305 A1 | 10/2009 | Seiwert et al. |
| 2009/0274648 A1 | 11/2009 | Wang et al. |
| 2009/0274652 A1 | 11/2009 | Sin et al. |
| 2009/0281141 A1 | 11/2009 | Simmen et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0304626 A1 | 12/2009 | Wang et al. |
| 2009/0304629 A1 | 12/2009 | Miao et al. |
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0021540 A1 | 1/2010 | Gopinathan et al. |
| 2010/0022578 A1 | 1/2010 | Raboisson et al. |
| 2010/0028300 A1 | 2/2010 | Llinas-Brunet et al. |
| 2010/0029666 A1 | 2/2010 | Harper et al. |
| 2010/0036116 A1 | 2/2010 | Scalone et al. |
| 2010/0041591 A1 | 2/2010 | Niu et al. |
| 2010/0041728 A1 | 2/2010 | Antonov et al. |
| 2010/0055071 A1 | 3/2010 | Leivers et al. |
| 2010/0068176 A1 | 3/2010 | Belema et al. |
| 2010/0068182 A1 | 3/2010 | Huang et al. |
| 2010/0069294 A1 | 3/2010 | Petter et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0080772 A1 | 4/2010 | Belema et al. |
| 2010/0081700 A1 | 4/2010 | Wang et al. |
| 2010/0081713 A1 | 4/2010 | Sharma et al. |
| 2010/0093792 A1 | 4/2010 | Berkenbusch et al. |
| 2010/0099695 A1 | 4/2010 | Liverton et al. |
| 2010/0113440 A1 | 5/2010 | Belfrage et al. |
| 2010/0124545 A1 | 5/2010 | Zhang et al. |
| 2010/0143499 A1 | 6/2010 | Condon |
| 2010/0144608 A1 | 6/2010 | Ku et al. |
| 2010/0150866 A1 | 6/2010 | Wang et al. |
| 2010/0158862 A1 | 6/2010 | Kim et al. |
| 2010/0160355 A1 | 6/2010 | Degoey et al. |
| 2010/0160403 A1 | 6/2010 | Link et al. |
| 2010/0168138 A1 | 7/2010 | Degoey et al. |
| 2010/0168384 A1 | 7/2010 | McDaniel et al. |
| 2010/0196321 A1 | 8/2010 | Cooper et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0240698 A1 | 9/2010 | Simmen et al. |
| 2010/0249190 A1 | 9/2010 | Lopez et al. |
| 2010/0260708 A1 | 10/2010 | Belema et al. |
| 2010/0260710 A1 | 10/2010 | Parsy et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0272674 A1 | 10/2010 | Hiebert et al. |
| 2010/0292219 A1 | 11/2010 | Agarwal et al. |
| 2010/0297079 A1 | 11/2010 | Almond et al. |
| 2010/0303755 A1 | 12/2010 | Lopez et al. |
| 2010/0310512 A1 | 12/2010 | Guo et al. |
| 2010/0316607 A1 | 12/2010 | Or et al. |

(56) References Cited

U.S. PATENT DOCUMENTS

| | | |
|---|---|---|
| 2010/0317568 A1 | 12/2010 | Degoey et al. |
| 2011/0008288 A1 | 1/2011 | Or et al. |
| 2011/0020272 A1 | 1/2011 | Schubert |
| 2011/0059047 A1 | 3/2011 | Seiwert et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0065737 A1 | 3/2011 | Liu et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0178107 A1 | 7/2011 | Wang et al. |
| 2011/0189129 A1 | 8/2011 | Qiu et al. |
| 2011/0195044 A1 | 8/2011 | Romine |
| 2011/0207660 A1 | 8/2011 | Sheth et al. |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2011/0312973 A1 | 12/2011 | Liepold et al. |
| 2012/0004196 A1 | 1/2012 | Degoey et al. |
| 2012/0028978 A1 | 2/2012 | Zhong et al. |
| 2012/0040977 A1 | 2/2012 | Li et al. |
| 2012/0076756 A1 | 3/2012 | Qiu et al. |
| 2012/0114600 A1 | 5/2012 | McKinnell et al. |
| 2012/0122864 A1 | 5/2012 | Zhong et al. |
| 2012/0172290 A1 | 7/2012 | Krueger et al. |
| 2012/0220562 A1 | 8/2012 | Degoey et al. |
| 2012/0258909 A1 | 10/2012 | Liepold et al. |
| 2013/0253008 A1 | 9/2013 | Ivachtchenko et al. |

FOREIGN PATENT DOCUMENTS

| | | | |
|---|---|---|---|
| DE | 4442257 A1 | 5/1996 | |
| EP | 1437362 A1 | 7/2004 | |
| EP | 1169339 B1 | 9/2004 | |
| EP | 1880715 A1 | 1/2008 | |
| EP | 1472278 B1 | 11/2008 | |
| EP | 1455809 B1 | 6/2011 | |
| EP | 2583680 A2 | 4/2013 | |
| EP | 2242751 B1 | 7/2015 | |
| JP | 2003282270 A | 10/2003 | |
| JP | 2007320925 A | 12/2007 | |
| JP | 2010126571 A | 6/2010 | |
| RU | 2286343 C2 | 10/2006 | |
| WO | 9427627 A1 | 12/1994 | |
| WO | 9640751 A1 | 12/1996 | |
| WO | 9640752 A1 | 12/1996 | |
| WO | 9907733 A2 | 2/1999 | |
| WO | 9961020 A1 | 12/1999 | |
| WO | 0000179 A1 | 1/2000 | |
| WO | 0009543 A2 | 2/2000 | |
| WO | 0009558 A1 | 2/2000 | |
| WO | 0012521 A1 | 3/2000 | |
| WO | 0059929 A1 | 10/2000 | |
| WO | 0214314 A2 | 2/2002 | |
| WO | 02060926 A2 | 8/2002 | |
| WO | 03053349 A2 | 7/2003 | |
| WO | 03064416 A1 | 8/2003 | |
| WO | 03064455 A2 | 8/2003 | |
| WO | 03064456 A1 | 8/2003 | |
| WO | 03066103 A1 | 8/2003 | |
| WO | 03082186 A2 | 10/2003 | |
| WO | 03099274 A1 | 12/2003 | |
| WO | 2004005283 A1 | 1/2004 | |
| WO | 2004014313 A2 | 2/2004 | |
| WO | 2004014852 A2 | 2/2004 | |
| WO | 2004030670 A1 | 4/2004 | |
| WO | 2004037855 A1 | 5/2004 | |
| WO | 2004039833 A1 | 5/2004 | |
| WO | 2004072243 A2 | 8/2004 | |
| WO | 2004087741 A1 | 10/2004 | |
| WO | 2004089974 A1 | 10/2004 | |
| WO | 2004092203 A2 | 10/2004 | |
| WO | 2004093798 A2 | 11/2004 | |
| WO | 2004093915 A1 | 11/2004 | |
| WO | 2004094452 A2 | 11/2004 | |
| WO | 2004103996 A1 | 12/2004 | |
| WO | 2005028501 A1 | 3/2005 | |
| WO | 2005037214 A2 | 4/2005 | |
| WO | 2005046712 A2 | 5/2005 | |
| WO | 2005051410 A1 | 6/2005 | |
| WO | 2005051980 A1 | 6/2005 | |
| WO | 2005054430 A2 | 6/2005 | |
| WO | 2005070955 A1 | 8/2005 | |
| WO | 2005075502 A1 | 8/2005 | |
| WO | 2005090383 A2 | 9/2005 | |
| WO | 2005095403 A2 | 10/2005 | |
| WO | 2005116054 A1 | 12/2005 | |
| WO | 2006000085 A1 | 1/2006 | |
| WO | 2006005479 A2 | 1/2006 | |
| WO | 2006020276 A2 | 2/2006 | |
| WO | 2006020951 A1 | 2/2006 | |
| WO | 2006033703 A2 | 3/2006 | |
| WO | 2006033851 A1 | 3/2006 | |
| WO | 2006033878 A1 | 3/2006 | |
| WO | 2006036614 A2 | 4/2006 | |
| WO | 2006093867 A1 | 9/2006 | |
| WO | 2006096652 A2 | 9/2006 | |
| WO | 2006114405 A2 | 11/2006 | |
| WO | 2006119061 A2 | 11/2006 | |
| WO | 2006122188 A2 | 11/2006 | |
| WO | 2006128455 A2 | 12/2006 | |
| WO | 2006130552 A2 | 12/2006 | |
| WO | 2006130553 A2 | 12/2006 | |
| WO | 2006130607 A2 | 12/2006 | |
| WO | 2006130626 A2 | 12/2006 | |
| WO | 2006130627 A2 | 12/2006 | |
| WO | 2006130628 A2 | 12/2006 | |
| WO | 2006130666 A2 | 12/2006 | |
| WO | 2006130686 A2 | 12/2006 | |
| WO | 2006130687 A2 | 12/2006 | |
| WO | 2006130688 A2 | 12/2006 | |
| WO | 2006133326 A1 | 12/2006 | |
| WO | 2007001406 A2 | 1/2007 | |
| WO | 2007005838 A2 | 1/2007 | |
| WO | 2007008657 A2 | 1/2007 | |
| WO | 2007009109 A2 | 1/2007 | |
| WO | 2007009227 A1 | 1/2007 | |
| WO | 2007014919 A1 | 2/2007 | |
| WO | 2007014921 A1 | 2/2007 | |
| WO | 2007014923 A1 | 2/2007 | |
| WO | 2007014924 A1 | 2/2007 | |
| WO | 2007014925 A1 | 2/2007 | |
| WO | 2007014926 A1 | 2/2007 | |
| WO | 2007015824 A2 | 2/2007 | |
| WO | 2007016441 A1 | 2/2007 | |
| WO | 2007030656 A1 | 3/2007 | |
| WO | 2007044893 A2 | 4/2007 | |
| WO | 2007044933 A1 | 4/2007 | |
| WO | 2007056120 A1 | 5/2007 | |
| WO | 2007070556 A2 | 6/2007 | |
| WO | 2007070600 A2 | 6/2007 | |
| WO | 2007076034 A2 | 7/2007 | |
| WO | 2007076035 A2 | 7/2007 | |
| WO | 2007081517 A2 | 7/2007 | |
| WO | 2007082554 A1 | 7/2007 | |
| WO | 2007131366 A1 | 11/2007 | |
| WO | 2007131966 A1 | 11/2007 | |

(56) References Cited

FOREIGN PATENT DOCUMENTS

| | | |
|---|---|---|
| WO | 2007139585 A1 | 12/2007 |
| WO | 2007143694 A2 | 12/2007 |
| WO | 2007144174 A1 | 12/2007 |
| WO | 2007148135 A1 | 12/2007 |
| WO | 2008002924 A2 | 1/2008 |
| WO | 2008008502 A1 | 1/2008 |
| WO | 2008008776 A2 | 1/2008 |
| WO | 2008014236 A1 | 1/2008 |
| WO | 2008014238 A2 | 1/2008 |
| WO | 2008019289 A2 | 2/2008 |
| WO | 2008019303 A2 | 2/2008 |
| WO | 2008021927 A2 | 2/2008 |
| WO | 2008021928 A2 | 2/2008 |
| WO | 2008021936 A2 | 2/2008 |
| WO | 2008021956 A2 | 2/2008 |
| WO | 2008021960 A2 | 2/2008 |
| WO | 2008022006 A2 | 2/2008 |
| WO | 2008039538 A2 | 4/2008 |
| WO | 2008046860 A2 | 4/2008 |
| WO | 2008051475 A2 | 5/2008 |
| WO | 2008051514 A2 | 5/2008 |
| WO | 2008057208 A2 | 5/2008 |
| WO | 2008057209 A2 | 5/2008 |
| WO | 2008057871 A2 | 5/2008 |
| WO | 2008057873 A2 | 5/2008 |
| WO | 2008057875 A2 | 5/2008 |
| WO | 2008057995 A2 | 5/2008 |
| WO | 2008059046 A1 | 5/2008 |
| WO | 2008060927 A2 | 5/2008 |
| WO | 2008062457 A2 | 5/2008 |
| WO | 2008064057 A1 | 5/2008 |
| WO | 2008064061 A1 | 5/2008 |
| WO | 2008064066 A1 | 5/2008 |
| WO | 2008064218 A2 | 5/2008 |
| WO | 2008070447 A2 | 6/2008 |
| WO | 2008070733 A2 | 6/2008 |
| WO | 2008074450 A2 | 6/2008 |
| WO | 2008086161 A1 | 7/2008 |
| WO | 2008092954 A2 | 8/2008 |
| WO | 2008095058 A1 | 8/2008 |
| WO | 2008096001 A1 | 8/2008 |
| WO | 2008098368 A1 | 8/2008 |
| WO | 2008101665 A1 | 8/2008 |
| WO | 2008106130 A2 | 9/2008 |
| WO | 2008114006 A1 | 9/2008 |
| WO | 2008124384 A2 | 10/2008 |
| WO | 2008128121 A1 | 10/2008 |
| WO | 2008128921 A1 | 10/2008 |
| WO | 2008133753 A2 | 11/2008 |
| WO | 2008137779 A2 | 11/2008 |
| WO | 2008141227 A1 | 11/2008 |
| WO | 2008144380 A1 | 11/2008 |
| WO | 2009003009 A1 | 12/2008 |
| WO | 2009005676 A2 | 1/2009 |
| WO | 2009005677 A1 | 1/2009 |
| WO | 2009010804 A1 | 1/2009 |
| WO | 2009014730 A1 | 1/2009 |
| WO | 2009020534 A2 | 2/2009 |
| WO | 2009020825 A1 | 2/2009 |
| WO | 2009020828 A1 | 2/2009 |
| WO | 2009039127 A1 | 3/2009 |
| WO | 2009039134 A1 | 3/2009 |
| WO | 2009053828 A2 | 4/2009 |
| WO | 2009067108 A1 | 5/2009 |
| WO | 2009070689 A1 | 6/2009 |
| WO | 2009070692 A1 | 6/2009 |
| WO | 2009073713 A1 | 6/2009 |
| WO | 2009073719 A1 | 6/2009 |
| WO | 2009073780 A1 | 6/2009 |
| WO | 2009080542 A1 | 7/2009 |
| WO | 2009082697 A1 | 7/2009 |
| WO | 2009082701 A1 | 7/2009 |
| WO | 2009085659 A1 | 7/2009 |
| WO | 2009094224 A1 | 7/2009 |
| WO | 2009099596 A2 | 8/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2009129109 A1 | 10/2009 |
| WO | 2009136290 A1 | 11/2009 |
| WO | 2009137432 A1 | 11/2009 |
| WO | 2009139792 A1 | 11/2009 |
| WO | 2009140475 A1 | 11/2009 |
| WO | 2009140500 A1 | 11/2009 |
| WO | 2009142842 A2 | 11/2009 |
| WO | 2009143361 A1 | 11/2009 |
| WO | 2009146347 A1 | 12/2009 |
| WO | 2009148923 A1 | 12/2009 |
| WO | 2009149377 A1 | 12/2009 |
| WO | 2009155709 A1 | 12/2009 |
| WO | 2010000459 A1 | 1/2010 |
| WO | 2010015090 A1 | 2/2010 |
| WO | 2010015545 A1 | 2/2010 |
| WO | 2010017035 A2 | 2/2010 |
| WO | 2010017401 A1 | 2/2010 |
| WO | 2010021717 A2 | 2/2010 |
| WO | 2010028236 A1 | 3/2010 |
| WO | 2010030359 A2 | 3/2010 |
| WO | 2010033443 A1 | 3/2010 |
| WO | 2010033444 A1 | 3/2010 |
| WO | 2010033466 A1 | 3/2010 |
| WO | 2010034105 A1 | 4/2010 |
| WO | 2010036551 A1 | 4/2010 |
| WO | 2010036871 A1 | 4/2010 |
| WO | 2010036896 A1 | 4/2010 |
| WO | 2010039793 A1 | 4/2010 |
| WO | 2010042834 A1 | 4/2010 |
| WO | 2010048468 A1 | 4/2010 |
| WO | 2010059667 A1 | 5/2010 |
| WO | 2010059858 A1 | 5/2010 |
| WO | 2010059937 A1 | 5/2010 |
| WO | 2010062821 A1 | 6/2010 |
| WO | 2010065577 A1 | 6/2010 |
| WO | 2010065668 A1 | 6/2010 |
| WO | 2010065674 A1 | 6/2010 |
| WO | 2010065681 A1 | 6/2010 |
| WO | 2010075376 A2 | 7/2010 |
| WO | 2010075380 A1 | 7/2010 |
| WO | 2010077783 A1 | 7/2010 |
| WO | 2010080389 A1 | 7/2010 |
| WO | 2010088394 A1 | 8/2010 |
| WO | 2010091413 A1 | 8/2010 |
| WO | 2010096302 A1 | 8/2010 |
| WO | 2010096462 A1 | 8/2010 |
| WO | 2010096777 A1 | 8/2010 |
| WO | 2010099527 A1 | 9/2010 |
| WO | 2010111483 A1 | 9/2010 |
| WO | 2010111534 A1 | 9/2010 |
| WO | 2010111673 A1 | 9/2010 |
| WO | 2010115767 A1 | 10/2010 |
| WO | 2010117635 A1 | 10/2010 |
| WO | 2010117704 A1 | 10/2010 |
| WO | 2010117977 A1 | 10/2010 |
| WO | 2010118078 A1 | 10/2010 |
| WO | 2010120476 A2 | 10/2010 |
| WO | 2010120621 A1 | 10/2010 |
| WO | 2010120935 A1 | 10/2010 |
| WO | 2010122162 A1 | 10/2010 |
| WO | 2010128521 A2 | 11/2010 |
| WO | 2010132538 A1 | 11/2010 |
| WO | 2010132601 A1 | 11/2010 |
| WO | 2010135520 A1 | 11/2010 |
| WO | 2010135748 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2010148006 A1 | 12/2010 |
| WO | 2011004276 A1 | 1/2011 |
| WO | 2011009084 A2 | 1/2011 |
| WO | 2011015658 A1 | 2/2011 |

(56) References Cited

FOREIGN PATENT DOCUMENTS

| | | |
|---|---|---|
| WO | 2011017389 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |
| WO | 2011050146 A1 | 4/2011 |
| WO | 2011054834 A1 | 5/2011 |
| WO | 2011059850 A1 | 5/2011 |
| WO | 2011059887 A1 | 5/2011 |
| WO | 2011060000 A1 | 5/2011 |
| WO | 2011063501 A1 | 6/2011 |
| WO | 2011063502 A1 | 6/2011 |
| WO | 2011066241 A1 | 6/2011 |
| WO | 2011068941 A2 | 6/2011 |
| WO | 2011075439 A1 | 6/2011 |
| WO | 2011075607 A1 | 6/2011 |
| WO | 2011075615 A1 | 6/2011 |
| WO | 2011079327 A1 | 6/2011 |
| WO | 2011081918 A1 | 7/2011 |
| WO | 2011082077 A1 | 7/2011 |
| WO | 2011087740 A1 | 7/2011 |
| WO | 2011091417 A1 | 7/2011 |
| WO | 2011091446 A1 | 7/2011 |
| WO | 2011091532 A1 | 8/2011 |
| WO | 2011109274 A1 | 9/2011 |
| WO | 2011112429 A1 | 9/2011 |
| WO | 2011112558 A2 | 9/2011 |
| WO | 2011119853 A1 | 9/2011 |
| WO | 2011119858 A1 | 9/2011 |
| WO | 2011119860 A1 | 9/2011 |
| WO | 2011119870 A1 | 9/2011 |
| WO | 2011127350 A1 | 10/2011 |
| WO | 2011146401 A1 | 11/2011 |
| WO | 2011150243 A1 | 12/2011 |
| WO | 2011156543 A2 | 12/2011 |
| WO | 2011156578 A1 | 12/2011 |
| WO | 2012039717 A1 | 3/2012 |
| WO | 2012040389 A2 | 3/2012 |
| WO | 2012040923 A1 | 4/2012 |
| WO | 2012040924 A1 | 4/2012 |
| WO | 2012041014 A1 | 4/2012 |
| WO | 2012041227 A1 | 4/2012 |
| WO | 2012050848 A1 | 4/2012 |
| WO | 2012050850 A1 | 4/2012 |
| WO | 2012051361 A1 | 4/2012 |
| WO | 2012068234 A2 | 5/2012 |
| WO | 2012074437 A2 | 6/2012 |
| WO | 2012083043 A1 | 6/2012 |
| WO | 2012083048 A2 | 6/2012 |
| WO | 2012083053 A2 | 6/2012 |
| WO | 2012083058 A2 | 6/2012 |
| WO | 2012083059 A1 | 6/2012 |
| WO | 2012083061 A2 | 6/2012 |
| WO | 2012083164 A1 | 6/2012 |
| WO | 2012087976 A2 | 6/2012 |
| WO | 2012116257 A1 | 8/2012 |
| WO | 2014004674 A2 | 1/2014 |
| WO | 2014063101 A1 | 4/2014 |

OTHER PUBLICATIONS

Abagyan R. et al., "ICM-A New Method for Protein Modeling and Design: Applications to Docking and Structure Prediction from the Distorted Native Conformation," Journal of Computational Chemistry, 1994, vol. 15 (5), pp. 488-506.
Adjabeng G. et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.
Adjabeng G. et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.
Akimoto M. et al., "Gastric pH Profiles of Beagle Dogs and their Use as an Alternative to Human Testing," European Journal of Pharmaceutics and Biopharmaceutics, 2000, vol. 49 (2), pp. 99-102.
Aldous D.J. et al., "A Simple Enantioselective Preparation of (2S,5S)-2,5-diphenylpyrrolidine and Related Diaryl Amines," Tetrahedron Asymmetry, 2000, vol. 11, pp. 2455-2462.
Alesso E.N. et al., "Synthesis of Diastereoisomeric 1,2,3-Triphenylindans," Australian Journal of Chemistry, 1997, vol. 50, pp. 149-152.
Alonzo D.E. et al., "Understanding the Behavior of Amorphous Pharmaceutical Systems During Dissolution," Pharmaceutical Research, 2010, vol. 27 (4), pp. 608-618.
Altschuel S.F. et al., "Basic Local Alignment Search Tool," Journal of Molecular Biology, 1990, 215 (3), pp. 403-410.
Altschul S.F. et al., "Gapped BLAST and PSI-BLAST: A New Generation of Protein Database Search Programs," Nucleic Acids Research, 1997, 25 (17), pp. 3389-3402.
Angiolini M. et al., "Synthesis of Azabicycloalkane Amino Acid Scaffolds as Reverse-Turn Inducer Dipeptide Mimics," European Journal Organization Chemistry, 2000, vol. 2000 (14), pp. 2571-2581.
Antares Health Products, "Vitamin E TPGS" downloaded from http://www.tpgs.com/.
Baker D. et al., "Protein Structure Prediction and Structural Genomics," Science, 2001, vol. 294 (5540), pp. 93-96.
Barbato G. et al, "Inhibitor Binding Induces Active Site Stabilization of the Hcv Ns3 Protein Serine Protease Domain," The EMBO Journal, 2000, vol. 19 (6), pp. 1195-1206.
Bartenschlager R., "Hepatitis C Virus Molecular Clones: From cDNA to Infectious Virus Particles in Cell Culture," Current Opinion in Microbiology, 2006, vol. 9 (4), pp. 416-422.
Bartenschlager R., "Hepatitis C Virus Replicons: Potential Role for Drug Development," Nature Reviews Drug Discovery, 2002, vol. 1 (11), pp. 911-916.
Bauer H. et al., "Methods for Determining Wetability and Their Potential Uses in Pharmaceutical Technology", Pharmacy, 1975, 30 (11), 689-693 (with Translation).
Beaumont, K. et al., "Design of Ester Prodrugs to Enhance Oral Absorption of Poorly Permeable Compounds Challenges to the Discovery Scientist," Current Drug Metabolism, 2003, vol. 4 (6), pp. 461-485.
Boehm T. et al., "Uber Die Bildung Von Gamma-Piperidonderivaten Aus Azetessigester, Aromatischen Aldehyden und Aminen, Eine Modifikation Der Hantzschschen Pyridinsynthese," Pharmaceutical, 1943, vol. 281, pp. 62-77 (with translation).
Bohm H.J., "The Computer Program LUDI: A New Method for the De Novo Design of Enzyme Inhibitors," Journal of Computer-Aided Molecular Design, 1992, vol. 6, pp. 61-78.
Brandrup J. et al., Editors, Polymer Handbook, Second Ed., Wiley-Interscience Publishers, 1975, Table of Contents.
Breitenbach J. et al., "Confocal Raman-Spectroscopy: Analytical Approach to Solid Dispersions and Mapping of Drugs," 1999, Pharmaceutical Research, vol. 16 (7), pp. 1109-1113.
Brettle R. et al., "A Highly Efficient Enzymic Route to Novel Chiral Liquid Crystals based on 3-Aryl-2-cycloalken-1-ones," Journal of the Chemical Society, Chemical Communications, 1994, vol. 1994 (19), pp. 2305-2306.
Brunger A.T. et al., "Recent Developments for the Efficient Crystallographic Refinement of Macromolecular Structures," Current Opinion in Structural Biology, 1998, vol. 8, pp. 606-611.
Buhler, V. "Kollidon®: Polyvinylpyrrolidone Excipients For The Pharmaceutical Industry," BASF SE, Pharma Ingredients & Services, Ludwlgshafen, Germany, Mar. 2008, 9th Ed. (331 pages).
Buhler, V., "Polyvinylpyrrolidone-Excipients for Pharmaceuticals" Povidone, Crospovidone and Copovidone Springer, Published 2005 (258 pages), Submitted in nine parts due to size.
Bundgaard H. Editor "Design of Pro Drugs," 1985 Elsevier Science Publishers, Chapters 1 and 2, pp. 1-133.
Charifson P.S. et al., "Novel Dual-Targeting Benzimidazole Urea Inhibitors of DNA Gyrase and Topoisomerase IV Possessing Potent Antibacterial Activity: Intelligent Design and Evolution through the

(56) References Cited

OTHER PUBLICATIONS

Judicious Use of Structure-Guided Design and Stucture-Activity Relationships," Journal of Medicinal Chemistry, 2008, vol. 51 (17), pp. 5243-5263.
Chong J.M. et al., "Asymmetric Synthesis of trans.2,5-Diphenylpyrrolidine: A C2-Symmetric Chiral Amine," Tetrahedron Asymmetry, 1995, vol. 6 (2), pp. 409-418.
Clark W.M. et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (1), pp. 1839-1842.
Clarke P.A. et al., "Pot, Atom and Step Economic (PASE) Synthesis of Highly Functionalized Piperidines: A Five-Component Condensation," Tetrahedron Letters, 2007, vol. 48, pp. 5209-5212.
Clarke P.A. et al., "Pot, Atom and Step Economic (PASE) Synthesis of Highly Substituted Piperidines: A Five-Component Condensation," Synthesis, 2008, No. 21, pp. 3530-3532.
Collado I. et al., "Stereoselective Addition of Grignard-Derived Organocopper Reagents to N-Acyliminium Ions: Synthesis of Enantiopure 5- and 4,5-Substituted Prolinates ,"Journal of Organic Chemistry, 1995, vol. 60, pp. 5011-5015.
Conte I. et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.
Cornell, W.D. et al., "A Second Generation Force Field for the Simulation of Proteins, Nucleic Acids, and Organic Molecules," Journal of the American Chemical Society, 1995, vol. 117, pp. 5179-5197.
De Francesco R. et al., "Challenges and Successes in Developing New Therapies for Hepatitis C," Nature, 2005, vol. 436 (7053), pp. 953-960.
Dell'Erba C. et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.
Dymock B.W., "Emerging Therapies for Hepatitis C Virus Infection," Expert Opinion on Emerging Drugs, 2001, vol. 6 (1), pp. 13-42.
Effenberger F. et al., "Synthesis, Structure, and Spectral Behavior of Donor-Acceptor Substituted Biphenyls," The Journal of Organic Chemistry, 1983, vol. 48 (24), pp. 4649-4658.
Eldridge M.D. et al., "Empirical Scoring Functions: I. The Development of a Fast Empirical Scoring Function to Estimate the Binding Affinity of Ligands in Receptor Complexes," Journal of Computer Aided Molecular Design, 1997, vol. 11 (5), pp. 425-445.
Eswar N. et al., "Comparative Protein Structure Modeling Using Modeller," Current Protocols in Bioinformatics, 2006, Suppl. 15, pp. 5.6.1-5.6.30.
Ettmayer P. et al., "Lessons Learned from Marketed and Investigational Prodrugs," Journal Medicinal Chemistry, 2004, vol. 47 (10), pp. 2393-2404.
European Search Report for Application No. EP12155991, dated Mar. 29, 2012, 2 pages.
Fan X. et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.
Feig M. et al., "Performance Comparison of Generalized Born and Poisson Methods in the Calculation of Electrostatic Salvation Energies for Protein Structures," Journal of Computational Chemistry, 2004, vol. 25 (2), pp. 265-284.
Fiedler, H. P., Encyclopedia of Excipients for Pharmaceuticals, Cosmetics and related Areas, 5th Edition, Hoepfner E.M. et al. Editors, Editio Cantor Verlag Aulendorf, 2002, Table of Contents (6 pages).
Fiser A. et al., "Modeling of Loops in Protein Structures," Protein Science, 2000, vol. 9 (9), pp. 1753-1773.
Forster A. et al., "Selection of Excipients for Melt Extrusion with Two Poorly Water-Soluble Drugs by Solubility Parameter Calculation and Thermal Analysis," International Journal of Pharmaceutics, 2001, vol. 226, pp. 147-161.

Galun E. et al., "Hepatitis C Virus Viremia in SCID-BNX Mouse Chimera," Journal of Infectious Diseases, 1995, vol. 172 (1), pp. 25-30.
Gastreich M. et al., "Ultrafast De Novo Docking Combining Pharmacophores and Combinatorics," Journal of Computer-Aided Molecular Design, 2006, vol. 20 (12), pp. 717-734.
Gillet V. et al., "SPROUT: A Program for Structure Generation," Journal of Computer-Aided Molecular Design, 1993, vol. 7 (2), pp. 127-153.
Gohlke H. et al., "Approaches to the Description and Prediction of the Binding Affinity of Small-Molecule Ligands to Macromolecular Receptors," Angewandte Chemie International Edition, 2002, vol. 41 (15), pp. 2644-2676.
Goodford P.J., "A Computational Procedure for Determining Energetically Favorable Binding Sites on Biologically Important Macromolecules," Journal of Medicinal Chemistry, 1985, vol. 28 (7), pp. 849-857.
Goodsell D.S. et al., "Automated Docking of Substrates to Proteins by Simulated Annealing," Proteins, 1990, vol. 8 (3), pp. 195-202.
Gordon T.D., et al, "Synthetic Approaches to the Azole Peptide Mimetics," Tetrahedron Letters, 1993, vol. 34(12), pp. 1901-1904.
Goudreau N. et al., "NMR Structural Characterization of Peptide Inhibitors Bound to the Hepatitis C Virus NS3 Protease: Design of a New P2 Substituent," Journal of Medicinal Chemistry, 2004, vol. 47 (1), pp. 123-132.
Goudreau N. et al., "The therapeutic potential of NS3 protease inhibitors in HCV infection," Expert Opinion on Investigational Drugs, vol. 14, No. 9, 2005, 1129-1144.
Greene, T.W. et al., Protective Groups in Organic Synthesis, 3rd Edition, John Wiley and Sons, Inc., 1999, Table of Contents, Abbreviations, pp. 494-653 and Index (pp. 749-779).
Halperin I. et al., "Principles of Docking: An Overview of Search Algorithms and a Guide to Scoring Functions," Proteins: Structure, Function, and Genetics, 2002, vol. 47 (4), pp. 409-443.
Han H.K. et al., "Targeted Prodrug Design to Optimize Drug Delivery," AAPS PharmSci, 2000, vol. 2 (1), pp. 1-11.
Hartwig J.F. et al., "111.3.2 Palladium-Catalyzed Amination of Aryl Halides and Related Reactions," Handbook of Organopalladium Chemistry for Organic Synthesis, E-I Negishi Editor, John Wiley & Sons, Inc. 2002, pp. 1051-1096.
Hoover J. et al. Editors, Remington's Pharmaceutical Sciences, 15th Edition, 1975, Table of Contents.
Hubbard S.R. et al., "Src Autoinhibition: Let us Count the Ways," Nature Structural Biology, 1999, vol. 6 (8), pp. 711-714.
International Search Report and Written Opinion for Application No. PCT/US2010/038077, mailed Jan. 21, 2011, 16 pages.
International Search Report for Application No. PCT/US2009/05082, mailed on Apr. 1, 2010, 1 page.
International Search Report and Written Opinion for Application No. PCT/US2009/069177, mailed on Aug. 10, 2010, 17 pages.
International Preliminary Report on Patentability and Written Opinion for Application No. PCT/US2009/069188, mailed on Jun. 29, 2011, 10 pages.
International Search Report for Application No. PCT/US2009/069188, mailed on Jun. 8, 2010, 4 pages.
International Preliminary Report on Patentability and Written Opinion for Application No. PCT/US2010/031102, mailed on Oct. 18, 2011, 7 pages.
International Search Report for Application No. PCT/US2010/031102, mailed on Sep. 1, 2010, 4 pages.
International Search Report for Application No. PCT/US2011/027511, mailed on Nov. 10, 2011, 3 pages.
International Search Report for Application No. PCT/US2011/039769, mailed on Oct. 6, 2011, 4 pages.
International Search Report for Application No. PCT/US2011/056045, mailed on Apr. 2, 2012, 4 pages.
International Search Report for Application No. PCT/US2011/065206, mailed on May 22, 2012, 3 pages.
International Search Report for Application No. PCT/US2011/065215, mailed on Jun. 12, 2012, 3 pages.
International Search Report for Application No. PCT/US2011/065224, mailed on Jun. 12, 2012, 3 pages.

(56) References Cited

OTHER PUBLICATIONS

International Search Report for Application No. PCT/US2011/065239, mailed on Jul. 30, 2012, 3 pages.
International Search Report for Application No. PCT/US2011/065242, mailed on May 22, 2012, 3 pages.
International Search Report for Application No. PCT/US2011/065247, mailed on Jun. 12, 2012, 3 pages.
International Search Report for Application No. PCT/US2011/065468, mailed on Mar. 26, 2012, 3 pages.
International Search Report for Application No. PCT/US2012/026456, mailed on Jun. 22, 2012, 3 pages.
International Search Report and Written Opinion for Application No. PCT/US2013/065760, mailed Dec. 12, 2013, 13 pages.
Jacques et al., "Enantiomers, Racemates, and Resolutions," J. Wiley & Sons, 1981 Chapter 3, pp. 197-213.
Jeffrey J.L. et al., "Concise Synthesis of Pauciflorol F Using a Larock Annulation," Organic Letters, 2009, vol. 11 (23), pp. 5450-5453.
Jing Q. et al., "Bulky Achiral Triarylphosphines Mimic BINAP in Ru(ll)- Catalyzed Asymmetric Hydrogenation of Ketones," Advanced Synthesis & Catalysis, 2005, vol. 347, pp. 1193-1197.
Johansson A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 2003, vol. 11 (12), pp. 2551-2568.
Jones G. et al., "Development and Validation of a Genetic Algorithm for Flexible Docking," Journal of Molecular Biology, 1997, vol. 267 (3), pp. 727-748.
Jones G. et al., "Docking Small-Molecule Ligands into Active Sites," Current Opinion in Biotechnology, 1995, vol. 6 (6), pp. 652-656.
Jones G. et al., "Molecular Recognition of Receptor Sites using a Genetic Algorithm with a Description of Desolvation," Journal of Molecular Biology, 1995, vol. 245 (1), pp. 43-53.
Kahlson G. et al "Mobilization and Formation of Histamine in the Gastric Mucosa as Related to Acid Secretion," Journal of Physiology, 1964, vol. 174, pp. 400-416.
Khan A.T. et al., "Effects of Substituents in the β-Position of 1,3-Dicarbonyl Compounds in Bromodimethylsulfonium Bromide-Catalyzed Multicomponent Reactions: A Facile Access to Functionalized Piperidines," Journal of Organic Chemistry, 2008, vol. 73, pp. 8398-8402.
Kim J.L. et al., "Crystal Structure of the Hepatitis C Virus NS3 Protease Domain Complexed with a Synthetic NS4A Cofactor Peptide," Cell, 1996, vol. 87 (2), pp. 343-355.
KOLLIDON® VA 64 and KOLLIDON® VA 64 Fine, Technical Information, BASF Chemical Company, Pharma Ingredients & Services, Aug. 2011 Issue (16 pages).
Kolykhalov A.A. et al., "Transmission of Hepatitis C by Intrahepatic Inoculation with Transcribed RNA," Science, 1997, vol. 277 (5325), pp. 570-574.
Kuethe J.T. et al., "Asymmetric Synthesis of 1,2,3-Trisubstituted Cyclopentanes and Cyclohexanes as Kev Components of Substance P Antagonists," Journal of Organic Chemistry, 2002, vol. 67 (17), pp. 5993-6000.
Kuntz I.D. et al., "A Geometric Approach to Macromolecule-Ligand Interactions," Journal of Molecular Biology, 1982, vol. 161 (2), pp. 269-288.
Lattman, E., "Use of the Rotation and Translation Functions," Methods in Enzymology, 1985, vol. 115, pp. 55-77.
Li, C. et al., "Olefination of Ketenes for the Enantioselective Synthesis of Allenes via an Ylide Route," Tetrahedron, 2007, vol. 63, pp. 8046-8053.
Lieberman H. et al., Editors, "Pharmaceutical Dosage Forms," vol. 1, Marcel Dekker, Inc., 1980, Table of Contents (5 pages).
Llinas-Brunet M. et al., "Peptide-Based Inhibitors of the Hepatitis C Virus Serine Protease," Bioorganic & Medicinal Chemistry Letters, 1998, vol. 8 (13), pp. 1713-1718.
Louie J. et al., "Palladium-Catalyzed Amination of Aryl Triflates and Importance of Triflate Addition Rate," Journal of Organic Chemistry, 1997, vol. 62 (5), pp. 1268-1273.

L-Selectride, Retrieved from the Internet: URL:http://en.wikipedia.org/w/index.php"oldid=488453454 (3 pages).
Lu, L. et al., "Mutations Conferring Resistance to a Potent Hepatitis C Virus Serine Protease Inhibitor in Vitro," Antimicrobial Agents and Chemotherapy, 2004, vol. 48 (6), pp. 2260-2266.
Lucas S. et al., "In Vivo Active Aldosterone Synthase Inhibitors with Improved Aelectivity: Lead Optimization Providing a Series of Pyridine Substituted 3,4-Dihydro-1 HQuinolin-2-one Derivatives," Journal of Medicinal Chemistry, 2008, vol. 51 (24), pp. 8077-8087.
Marti-Renom M.A. et al., "Comparative Protein Structure Modeling of Genes and Genomes," Annual Review of Biophysics and Biomolecular Structure, 2000, vol. 29, pp. 291-325.
Maschke A. "Excipients & Activities for Pharma", ExAct, No. 20, May 2008, Publisher BASF SE, 16 pages.
Masui M. et al., "A Practical Method for Asymmetric Borane Reduction of Prochiral Ketones Using Chiral Amino Alcohols and Trimethyl Borate," Synlett, 1997, vol. 1997 (3), pp. 273-274.
Matzeit A. et al., "Radical Tandem Cyclizations by Anodic Decarboxylation of Carboxylic Acids," Synthesis, 1995, vol. 1995 (11), pp. 1432-1444.
Mercer D.F. et al., "Hepatitis C Virus Replication in Mice with Chimeric Human Livers," Nature Medicine, 2001, vol. 7 (8), pp. 927-933.
Miranker A. et al., "Functionality Maps of Binding Sites: A Multiple Copy Simultaneous Search Method," Proteins: Structure, Function, and Genetics, 1991, vol. 11 (1), pp. 29-34.
Misra M. et al., "Organocatalyzed Highly Atom Economic One Pot Synthesis of Tetrahydropyridines as Antimalarials," Bioorganic & Medicinal Chemistry, 2009, vol. 17, pp. 625-633.
Moinet C. et al., "Novel Non-Peptide Ligands for the Somatostatin sst3 Receptor," Bioorganic & Medicinal Chemistry Letters, 2001, vol. 11 (8), pp. 991-995.
Muci A.R. et al., "Practical Palladium Catalysts for C-N and C-0 Bond Formation," Topics in Current Chemistry, 2002, vol. 219, pp. 131-209.
Muller C.E. "Prodrug Approaches for Enhancing the Bioavailability of Drugs with Low Solubility," Chemistry & Biodiversity, 2009, vol. 6 (11), pp. 2071-2083.
Muri E.M.F. et al., "Pseudo-Peptides Derived From lsomannide As Potential Inhibitors Of Serine Proteases," Amino Acids, 2005, vol. 28 (4), pp. 413-419.
Navaza J. "AMoRe: An Automated Package for Molecular Replacement," Acta Crystallographica, 1994, vol. A50 (2), pp. 157-163.
Naylor E.M. et al., "3-Pyridylethanolamines: Potent and Selective Human 63 Adrenergic Receptor Agonists," Bioorganic & Medicinal Chemistry Letters, 1998, vol. 8 (21), pp. 3087-3092.
Nevar N. M. et al., "One Step Preparation of 1,4-Diketones from Methyl Ketones and a-Bromomethyl Ketones in the Presence of ZnCl2•t-BuOH•Et2NR as a Condensation Agent," Synthesis, 2000, vol. 9, pp. 1259-1262.
Nishibata Y. et al., "Confirmation of Usefulness of a Structure Construction Program Based on Three-Dimensional Receptor Structure for Rational Lead Generation," Journal of Medicinal Chemistry, 1993, vol. 36 (20), pp. 2921-2928.
Pak V.D. et al., "Catalytic Condensation of Schiff's Base With P-Methoxybenzal Acetone," Catalytic Synthesis of Organic Nitrate Compounds, 1970, vol. 68 (Part 4), pp. 66-71.
Peng T. et al., "Construction of a Library of Rhodol Fluorophores for Developing New Fluorescent Probes," Organic Letters, 2010, vol. 12 (3), pp. 496-499.
Penning T.D. et al, "Discovery and SAR of 2-(1-Propylpiperidin-4-yl)-1 H-Benzimidazole-4-Carboxamide: A Potent Inhibitor of Poly(ADP-ribose) Polymerase (PARP) for the Treatment of Cancer," Bioorganic & Medicinal Chemistry, 2008, vol. 16(14), pp. 6965-6975.
Rancourt J. et al., "Peptide-Based Inhibitors of the Hepatitis C Virus NS3 Protease: Structure-Activity Relationship at the C-Terminal Position," Journal of Medicinal Chemistry, 2004, vol. 47 (10), pp. 2511-2522.
Rao S.N. et al., "Validation Studies of the Site-Directed Docking Program LibDock," Journal of Chemical Information and Modeling, 2007, vol. 47 (6), pp. 2159-2171.

(56) References Cited

OTHER PUBLICATIONS

Rarey M. et al., "A Fast Flexible Docking Method using an Incremental Construction Algorithm," Journal of Molecular Biology, 1996, vol. 261 (3), pp. 470-489.
Reintjes T. Editor "Solubility Enhancement with BASF Pharma Polymers: Solubilizer Compendium," BASF SE, Pharma Ingredients & Services, Lampertheim, Germany, Oct. 2011 (130 pages). Submitted in two parts due to size.
Ronn R. et al., "Exploration of Acyl Sulfonamides as Carboxylic Acid Replacements in Protease Inhibitors of the Hepatitis C Virus Full-length N53," Bioorganic & Medicinal Chemistry Letters, 2006, vol. 14 (2), pp. 544-559.
Rosen M.H. et al., "Contraceptive Agents from Cycloaddition Reactions of Diarylcyclopropenones and Diarylthiirene 1,1-Dioxides," Journal of Medicinal Chemistry, 1976, vol. 19 (3), pp. 414-419.
Rosenberg J. et al., "Amorphous Embedding of a Lipophilic Drug Substance by Meltrex-Technology," Journal of Controlled Release, Abstracts, 2003, vol. 87, pp. 264-267.
Rossmann M.G., "The Molecular Replacement Method: A Collection of Papers on the Use of Non-Crystallographic Symmetry" Gordon and Breach Science Publishers, 1972, Table of Contents, 6 pages.
Sali A. et al., "Comparative Protein Modelling by Satisfaction of Spatial Restraints," Journal of Molecular Biology, 1993, vol. 234 (3), pp. 779-815.
Sato H. et al., "Prediction of Multiple Binding Modes of the CDK2 Inhibitors, Anilinopyrazoles, Using the Automated Docking Programs GOLD, FlexX, and LigandFit: An Evaluation of Performance," Journal of Chemical Information and Modeling, 2006, vol. 46 (6), pp. 2552-2562.
Sato M. et al., "Efficient Preparation of Optically Pure C2-Symmetrical Cyclic Amines for Chiral Auxiliary," Synthesis, 2004, vol. 9, pp. 1434-1438.
Sawyer J.S. et al., "Synthetic and Structure/Activity Studies on Acid-Substituted 2-Arylphenols: Discovery of 2-[2-Propyl-3-[3-[2-ethyl-4-(4-fluorophenyl)-5-hydroxyphenoxy]-propoxy]phenoxy] benzoic Acid, a High Affinity Leukotriene B4 Receptor Antagonist," Journal of Medicinal Chemistry, 1995, vol. 38 (22), pp. 4411-4432.
Serajuddin A.T.M., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.
Singh Y. et al., "Recent Trends in Targeted Anticancer Prodrug and Conjugate Design," Current Medical Chemistry, 2008, vol. 15 (18), pp. 1802-1826.
Smith A.B. et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.
Smith D.C. et al., "Reissert Compound Chemistry. XXVI. The Syntheses of Bis-Benzvlisoquinolines," Journal of Heterocyclic Chemistry, 1976, vol. 13, pp. 573-576.
SOLUPLUS®, Technical Information, BASF Chemical Company, Pharma Ingredients & Services, Jul. 2010 Issue (8 pages).
Sousa S.F. et al., "Protein-Ligand Docking: Current Status and Future Challenges," Proteins: Structure, Function, and Bioinformatics, 2006, vol. 65 (1), pp. 15-26.
Sperling L. H. Editor, "Introduction to Physical Polymer Science," 2nd Edition, John Wiley & Sons, Inc., 1992, Table of Contents.
Sree Giri Prasad.B. et al., "Formulation and Evaluation of Oro Dispersible Tablets of Stavudine by Direct Compression Technique", Der Pharmacia Lettre, 2012, vol. 4 (5), pp. 1505-1514.
Sugawara M. et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.
Takagi S. et al., "Antimicrobial Agents From Bletilla Striata," Phytochemistry, 1983, vol. 22 (4), pp. 1011-1015.
Tatsumi K. et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.
Tellinghuisen T.L. et al., "Structure of the Zinc-Binding Domain of an Essential Component of the Hepatitis C Virus Replicase," Nature, 2005, vol. 435 (7040), pp. 374-379.
Testa B. et al., "Prodrug Research: Futile or Fertile?," Biochemical Pharmacology, 2004, vol. 68, pp. 2097-2106.
Thayer A. M., "Finding Solutions, Custom manufacturers take on drug solubility issues to help pharmaceutical firms move products through development," Chemical & Engineering News, 2010, vol. 88 (22), pp. 13-18.
Tsantrizos Y.S. et al., "Macrocyclic Inhibitors of the NS3 Protease as Potential Therapeutic Agents of Hepatitis C Virus Infection," Angewandte Chemie International Edition, 2003, vol. 42 (12), pp. 1355-1360.
Vagin A. et al., "MOLREP: An Automated Program for Molecular Replacement," Journal of Applied Crystallography, 1997, vol. 30, pp. 1022-1025.
Vallee M.R.J. et al., "Photoannelation Reactions of 3-(Alk-1-ynyl)cyclohept-2-en-1-ones," Helvetica Chimica Acta, 2010, vol. 93 (1), pp. 17-24.
Verboom W. et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.
Warren G.L. et al., "A Critical Assessment of Docking Programs and Scoring Functions," Journal of Medicinal Chemistry, 2006, vol. 49 (20), pp. 5912-5931.
Willis M.C. et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.
Wolfe J.P. et al., "Palladium-Catalyzed Amination of Aryl Triflates," Journal of Organic Chemistry, 1997, vol. 62 (5), pp. 1264-1267.
Written Opinion for Application No. PCT/US2011/027511, dated Nov. 10, 2011, 6 pages.
Wu G.Y. et al., "A Novel Immunocompetent Rat Model of HCV Infection and Hepatitis," Gastroenterology, 2005, vol. 128 (5), pp. 1416-1423.
Xiao D. et al., "A Practical Synthetic Pathway to Polysubstituted Tetrahydropyridines via Multicomponent Reactions Catalyzed by BF3•OEt2," Synlett, 2005, vol. 10, pp. 1531-1534.
Xie Z.C. et al., "Transmission of Hepatitis C Virus Infection to Tree Shrews," Virology, 1998, vol. 244 (2), pp. 513-520.
Yanagi M. et al., "Transcripts from a Single Full-Length cDNA Clone of Hepatitis C Virus are Infectious when Directly Transfected into the Liver of a Chimpanzee," Proceedings of the National Academy of Sciences, 1997, vol. 94 (16), pp. 8738-8743.
Yu H. et al., "The Discovery of Novel Vascular Endothelial Growth Factor Receptor Tyrosine Kinases Inhibitors: Pharmacophore Modeling, Virtual Screening and Docking Studies," Chemical Biology and Drug Design, 2007, vol. 69 (3), pp. 204-211.
Zhang J. et al., "Stereoselective Bromination-Suzuki Cross-Coupling of Dehydroamino Acids To Form Novel Reverse-Turn Peptidomimetics: Substituted Unsaturated and Saturated Indolizidinone Amino Acids," Organic Letters, 2002, vol. 4 (23), pp. 4029-4032.
Zhu Q. et al., "Novel Robust Hepatitis C Virus Mouse Efficacy Model," Antimicrobial Agents and Chemotherapy, 2006, vol. 50 (10), pp. 3260-3268.

* cited by examiner

SOLID ANTIVIRAL DOSAGE FORMS

CROSS-REFERENCE TO RELATED APPLICATIONS

This application is a continuation of International Application No. PCT/US2015/010060 with an international filing date of Jan. 2, 2015, which is incorporated herein by reference in its entirety, and claims priority to U.S. Provisional Application No. 61/976,934 filed Apr. 8, 2014, and U.S. Provisional Application No. 61/923,544 filed Jan. 3, 2014, both of which are incorporated herein by reference in their entirety.

FIELD OF THE INVENTION

The present disclosure relates to solid dosage forms comprising antiviral compounds, methods of preparing the solid dosage forms, and methods of using such dosage forms to treat antiviral infection.

BACKGROUND OF THE INVENTION

Hepatitis C virus ("HCV") infection is associated with progressive liver pathology, including cirrhosis and hepatocellular carcinoma. Standard of care for treating chronic HCV infection generally comprises administration of peginterferon-alpha in combination with ribavirin to the patient. Treatment often additionally comprises administering a hepatitis C protease inhibitor to genotype 1-infected patients. Many patients, however, suffer side effects from the treatment, and viral elimination from the body is often inadequate. In view of the limited efficacy and tolerability of such standard of care treatment, there remains a need for new drugs to treat HCV infection.

BRIEF DESCRIPTION OF THE INVENTION

The present disclosure relates to solid dosage forms comprising Compound 1, Compound 2, Compound 3, and Compound 4 (as those compounds are defined in the disclosure below).

In an aspect, the present disclosure relates to solid dosage forms comprising Compound 1, Compound 2, and Compound 3 in a first composition, and Compound 4 in a second composition.

In one aspect, the present disclosure relates to solid dosage forms comprising Compound 1, Compound 2, Compound 3, and Compound 4, wherein the weight ratio (free acid or free base) of Compound 1:Compound 2:Compound 3 is from 10:1:2 to 2:1:3.

In another aspect, the disclosure relates to solid dosage forms comprising:
 (a) 40 mg to 180 mg (free acid equivalent weight) of Compound 1;
 (b) 5 mg to 30 mg (free base equivalent weight) of Compound 2;
 (c) 25 mg to 120 mg (free base equivalent weight) of Compound 3; and
 (d) 75 mg to 900 mg (free acid equivalent weight) of Compound 4.

In another aspect, the disclosure relates to solid dosage forms comprising:
 (a) a first composition comprising:
  (i) 40 mg to 90 mg (free acid equivalent weight) of Compound 1;
  (ii) 5 mg to 15 mg (free base equivalent weight) of Compound 2; and
  (iii) 25 mg to 60 mg (free base equivalent weight) of Compound 3; and
 (b) a second composition comprising:
  (i) 75 mg to 450 mg (free acid equivalent weight) of Compound 4;
  (ii) a pharmaceutically acceptable stabilizing polymer, or combination of pharmaceutically acceptable stabilizing polymers, in an amount of at least 5% by weight of the second composition; and
  (iii) a pharmaceutically acceptable release rate-modifying polymer, or combination of pharmaceutically acceptable release rate-modifying polymers, in an amount of at least 5% by weight of the second composition;
  wherein the stabilizing polymer, or combination of stabilizing polymers, and the release rate-modifying polymer, or combination of release rate-modifying polymers, can be the same or different.

In another aspect, the disclosure relates to methods for treating HCV infection in a subject in need of such treatment, wherein the methods comprise administering at least one dosage form of the present disclosure once daily to the subject. In one aspect, the methods comprise administering two dosage forms of the present disclosure once daily to the subject. In another aspect, the methods comprise administering three dosage forms of the present disclosure once daily to the subject.

In another aspect, the disclosure relates to methods for treating liver disease in a subject in need of such treatment, wherein the methods comprise administering at least one dosage form of the present disclosure once daily to the subject. In one aspect, the methods comprise administering two dosage forms of the present disclosure once daily to the subject. In another aspect, the methods comprise administering three dosage forms of the present disclosure once daily to the subject.

In another aspect, the disclosure relates to kits comprising one or more of the dosage forms of the present disclosure.

In another aspect, the disclosure relates to processes for making the dosage forms of the present disclosure, wherein the processes comprise:
 (a) preparing a melt comprising Compound 1, Compound 2, Compound 3, a hydrophilic polymer, and a surfactant;
 (b) solidifying the melt to provide an amorphous solid dispersion;
 (c) preparing a first composition comprising the amorphous solid dispersion;
 (d) preparing a second composition comprising Compound 4 and a pharmaceutically acceptable stabilizing polymer, or combination of pharmaceutically acceptable stabilizing polymers; and
 (e) formulating the first composition and the second composition to provide the dosage form.

In another aspect, the disclosure relates to solid dosage forms prepared in accordance with the above processes.

DETAILED DESCRIPTION OF THE INVENTION

This written description uses examples to illustrate the invention and also to enable any person skilled in the art to practice the invention, including making and using any compositions and performing any related methods. The patentable scope of the invention is defined by the claims, and may include other examples that occur to those skilled in the art. Such other examples are intended to be within the scope of the claims if they have structural elements that do not differ from the literal language of the claims or if they include equivalent structural elements with insubstantial differences from the literal language of the claims.

I. DEFINITIONS

Section headings as used in this section and the entire disclosure are not intended to be limiting.

Where a numeric range is recited, each intervening number within the range is explicitly contemplated with the same degree of precision. For example, for the range 6 to 9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated. In the same manner, all recited ratios also include all sub-ratios falling within the broader ratio.

The term "$AUC_\infty$" refers to the area under the plasma concentration-time curve from the time 0 (time of dosing) to infinity (∞), as calculated by the linear trapezoidal method.

The term "$C_{max}$" refers to the maximum observed plasma concentration over the entire sampling period.

The term "$C_{24}$" refers to the plasma concentration at 24 hours.

The term "particle size" refers to particle size as measured by conventional particle size measuring techniques such as laser light scattering. The term "$D_{10}$ particle size" means the particle size distribution of at least 10% of the particles as measured by laser light scattering particle size measuring techniques. The term "$D_{50}$ particle size" means the particle size distribution of at least 50% of the particles as measured by laser light scattering particle size measuring techniques. The term "$D_{90}$ particle size" means the particle size distribution of at least 90% of the particles as measured by laser light scattering particle size measuring techniques.

The term "subject" refers to a human subject.

The term "$T_{max}$" refers to the time of the maximum observed plasma concentration ($C_{max}$).

The abbreviation "cTAB" means cetyltrimethylammonium bromide.

The abbreviation "FeSSIF" means Fed-State Simulated Intestinal Fluid.

The abbreviation "HCV" means hepatitis C virus.

The abbreviation "HLB" means Hydrophobic-Lipophilic Balance.

The abbreviation "HPMC" means hydroxypropyl methylcellulose.

The abbreviation "PXRD" means powder X-ray diffraction.

The abbreviation "$T_g$" means glass transition temperature.

The abbreviation "v/v" refers to volume/volume.

The abbreviation "w/v" refers to weight/volume.

The abbreviation "w/w" refers to weight/weight.

II. SOLID DOSAGE FORMS

Combination therapy treatment of HCV-infected adult human subjects comprising the administration to those subjects of Compound 1, Compound 2, Compound 3, and Compound 4 (which are further described below) was evaluated in Phase III clinical trials. The Phase III trials employed two separate dosage forms, a first tablet comprising Compound 1, Compound 2, and Compound 3 (the "Triple Tablet"), and a second tablet comprising Compound 4 as the only active ingredient (the "Single Tablet"). The daily dosing regimen under evaluation in the Phase III clinical trials has required administration to the subject of two Triple Tablets and one Single Tablet in the morning and the administration of one Single Tablet to the subject in the evening. Initial results have indicated that such combination therapy treatment is effective.

A. Active Ingredients

Compound 1:

The compound (2R,6S,13aS,14aR,16aS,Z)—N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide (also known as ABT-450 or paritaprevir) is an HCV protease inhibitor and has the structure shown below:

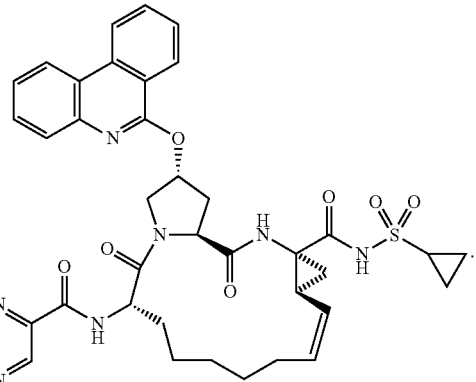

For convenience, this compound and its pharmaceutically acceptable salts are collectively referred to as Compound 1 throughout this disclosure. The synthesis and formulation of Compound 1 are described, for example, in U.S. Patent Application Publication Nos. 2010/0144608 and 2011/0312973.

Compound 2:

The compound dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis-(oxomethylene)bis(pyrrolidine-2,1-diyl))bis(3-methyl-1-oxobutane-2,1-diyl)-dicarbamate (also known as ABT-267 or ombitasvir) is an HCV NS5A inhibitor and has the structure shown below:

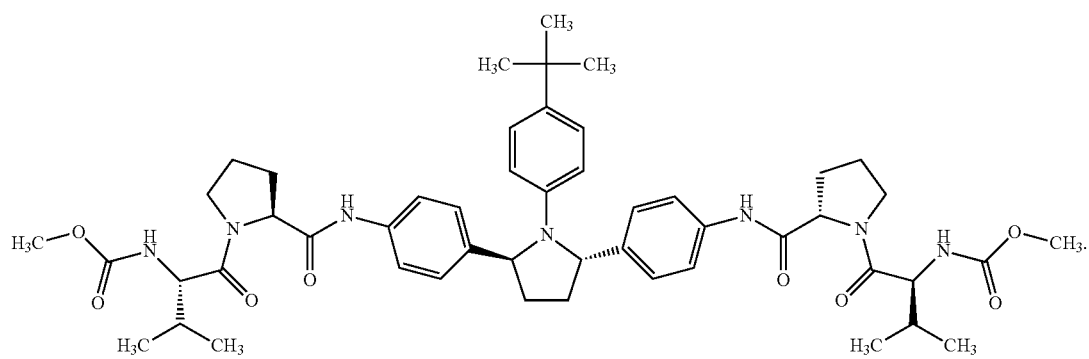 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

For convenience, this compound and its pharmaceutically acceptable salts are collectively referred to as Compound 2 throughout this disclosure. The synthesis and formulation of Compound 2 are described, for example, in U.S. Patent Application Publication Nos. 2010/0317568 and 2012/0258909.

Compound 3:

The compound 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]-amino}butanamido]-1,6-diphenylhexan-2-yl]carbamate (also known as ritonavir) is a protease inhibitor and has the structure shown below:

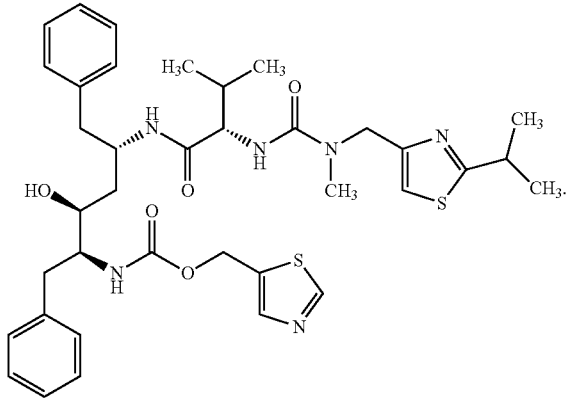 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

For convenience, this compound and its pharmaceutically acceptable salts are collectively referred to as Compound 3 throughout this disclosure. The synthesis and formulation of Compound 3 are described, for example, in U.S. Pat. No. 5,541,206 and U.S. Pat. No. 8,268,349. Compound 3 is the active ingredient in the commercially available product NORVIR®.

Compound 4:

The compound N-(6-(3-tert-butyl-5-(2,4-dioxo-3,4-dihydropyrimidin-1(2H)-yl)-2-methoxyphenyl)naphthalen-2-yl)methanesulfonamide (also known as ABT-333 or dasabuvir) is a polymerase inhibitor and has the structure shown below:

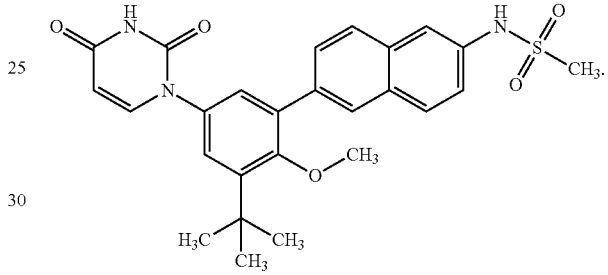

For convenience, this compound and its pharmaceutically acceptable salts are collectively referred to as Compound 4 throughout this disclosure. The synthesis and formulation of Compound 4 are described, for example, in International Application Publication WO2009/039134.

Unless otherwise stated, any reference in this disclosure to an amount of Compound 1, Compound 2, Compound 3, or Compound 4 is intended to refer to the free acid or free base equivalent weight of the compound. For example, 350 mg of Compound 4 refers to 350 mg of the free acid of Compound 4 or an equivalent amount of a salt (e.g., a sodium salt) of Compound 4.

The present disclosure relates, in part, to one or more solid dosage forms that comprise all four of the active ingredients (Compound 1, Compound 2, Compound 3, and Compound 4) employed in the combination therapy evaluated in Phase III clinical trials discussed above. Such solid dosage forms, inter alia, can be administered to the subject pursuant to a once-daily dosing regimen, provide substantially comparable efficacy relative to, and are preferably bioequivalent to, the Triple Tablet/Single Tablet dosing regimen, and/or result in improved patient compliance. However, co-formulation of all four active ingredients in a single solid dosage form has been challenging in view of a number of factors, including the following:

(a) Total Daily Dose: The combined daily dose of Compound 1 (150 mg), Compound 2 (25 mg), Compound 3 (100 mg), and Compound 4 (500 mg) administered to the subject in Phase III clinical trials is relatively large, totaling 775 mg and must be administered in four tablets.

(b) Dosage Form Size: The Triple Tablet (1117 mg) and Single Tablet (697 mg) administered to subjects in Phase III clinical trials are large in size.

(c) Drug Loading: Drug loading limitations previously impacted the development of the Triple Tablet. Consolidating the four active ingredients into a single dosage form only exacerbates that problem.

(d) Different Pharmacokinetic Profiles: The daily dosing regimen for the Triple Tablet (once-daily dosing regimen) and the Single Tablet (twice-daily dosing regimen) differ, and deliver a specific pharmacokinetic profile for each of the four compounds.

(e) Solubility: Compound 1, Compound 2, Compound 3, and Compound 4 have low solubility. They generally exhibit lower bioavailability and/or higher variability in bioavailability relative to more soluble compounds due to their poor aqueous solubility and low dissolution.

(f) Free Acid Conversion (Compound 4): The free acid of Compound 4 exhibits good permeability but poor solubility in the gastrointestinal tract. Administering a salt of Compound 4 (such as the sodium salt) rather than the free acid form of Compound 4, however, does not improve Compound 4 solubility and uptake in the gastrointestinal tract to the extent expected due to unknown reasons.

(g) Regional Absorption (Compound 4): The rate and extent of Compound 4 absorption varies throughout the gastrointestinal tract, making it difficult to design a once daily dosing that is bioequivalent to twice daily dosing.

Individually, the above considerations present significant challenges to co-formulating all four active ingredients in a suitable solid dosage form. Collectively, these considerations further increase the difficulty of co-formulating all four active ingredients in a suitable solid dosage form without adversely impacting dosage form size and/or the number of unit dosage forms that must be administered on a daily basis while achieving suitable efficacy and bioavailability.

B. Therapeutic Dose and Regimen

The dosage forms of the present invention are administered in accordance with a daily dosing regimen that orally delivers a therapeutic amount of Compounds 1, 2, 3, and 4 to a subject. This daily dosing regimen generally delivers an amount of Compounds 1, 2, 3, and 4 within the ranges set forth in Table A below.

TABLE A

| Daily Therapeutic Dose | |
|---|---|
| ACTIVE INGREDIENT | DAILY THERAPEUTIC DOSE (mg) |
| Compound 1 | 80 to 180 (e.g., 150) |
| Compound 2 | 10 to 30 (e.g., 25) |
| Compound 3 | 50 to 120 (e.g., 100) |
| Compound 4 | 450 to 900 (e.g., 500 or 600) |

Due to drug loading limitations and dosage form size constraints, administration of two or more of the dosage forms of the present invention typically will be required to deliver the necessary daily therapeutic dose to the subject. In one aspect, daily administration of two of the dosage forms will provide the necessary daily therapeutic dose to the subject. In another aspect, daily administration of three of the dosage forms will provide the necessary daily therapeutic dose to the subject. If desired, however, daily administration of four or more of the dosage forms can be employed to provide the necessary daily therapeutic dose to the subject.

C. Dosage Form: Illustrative Embodiments

The present disclosure relates, in part, to a solid dosage form comprising:

(a) 40 mg to 180 mg (free acid equivalent weight) of Compound 1, wherein Compound 1 is:

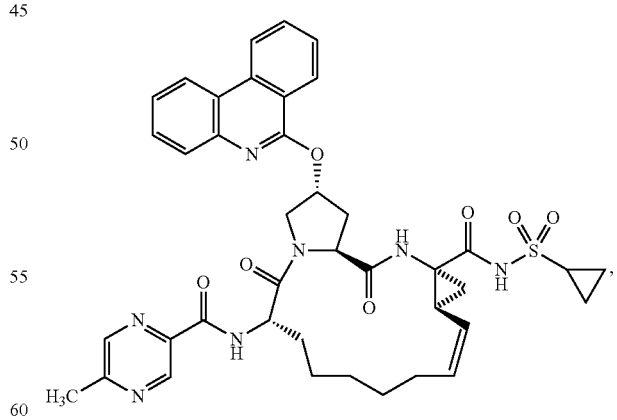

or a pharmaceutically acceptable salt thereof;

(b) 5 mg to 30 mg (free base equivalent weight) of Compound 2, wherein Compound 2 is:

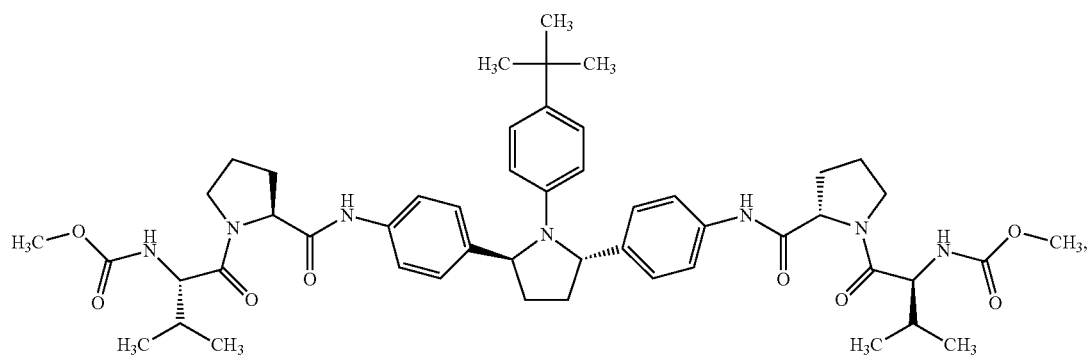 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

or a pharmaceutically acceptable salt thereof;
(c) 25 mg to 120 mg (free base equivalent weight) of Compound 3, wherein Compound 3 is ritonavir, or a pharmaceutically acceptable salt thereof; and
(d) 75 mg to 900 mg (free acid equivalent weight) of Compound 4, wherein Compound 4 is:

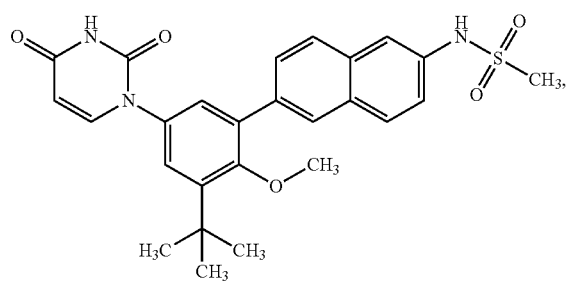 [SMILES: COc1c(-c2ccc3cc(NS(C)(=O)=O)ccc3c2)cc(-n2ccc(=O)[nH]c2=O)cc1C(C)(C)C]

or a pharmaceutically acceptable salt thereof.

The dosage form generally will comprise Compounds 1, 2, and 3 at a weight ratio (free acid or free base) of 3:2:24 to 60:3:5 (Compound 1:Compound 2:Compound 3). In one aspect, the weight ratio is 10:1:2 to 2:1:3 (Compound 1:Compound 2:Compound 3). In another aspect, the weight ratio is 6:1:4 (Compound 1:Compound 2:Compound 3).

Suitable dosage forms (e.g., tablets, capsules, sachets, etc.) and representative examples of such dosage form types are discussed in greater detail in Section II.J below.

As mentioned above, the dosage forms of the present disclosure may be administered pursuant to a daily dosing regimen that comprises, for example, either administering two of the dosage forms daily to the subject or administering three of the dosage forms daily to the subject. In one aspect, the two or three dosage forms are administered to the subject substantially simultaneously each day. In one aspect, the two or three dosage forms are administered to the subject substantially sequentially each day. Representative embodiments of dosage forms that can be employed in each regimen are set forth below.

In one embodiment, the dosage forms comprises:
(a) 40 mg to 90 mg (free acid equivalent weight) of Compound 1;
(b) 5 mg to 15 mg (free base equivalent weight) of Compound 2;
(c) 25 mg to 60 mg (free base equivalent weight) of Compound 3; and
(d) 75 mg to 450 mg (free acid equivalent weight) of Compound 4.

In another embodiment, the dosage form comprises:
(a) a first composition comprising:
(i) 40 mg to 90 mg (free acid equivalent weight) of Compound 1;
(ii) 5 mg to 15 mg (free base equivalent weight) of Compound 2; and
(iii) 25 mg to 60 mg (free base equivalent weight) of Compound 3; and
(b) a second composition comprising:
(i) 75 mg to 450 mg (free acid equivalent weight) of Compound 4;
(ii) a pharmaceutically acceptable stabilizing polymer, or combination of pharmaceutically acceptable stabilizing polymers, in an amount of at least 5% by weight of the second composition; and
(iii) a pharmaceutically acceptable release rate-modifying polymer, or combination of pharmaceutically acceptable release rate-modifying polymers, in an amount of at least 5% by weight of the second composition;
wherein the stabilizing polymer, or combination of stabilizing polymers, and the release rate-modifying polymer, or combination of release rate-modifying polymers, can be the same or different.

The first composition may further comprise a portion of the total amount of Compound 4 present in the dosage form. The amount of Compound 4 present in the first composition may not exceed the amount of Compound 4 present in the second composition. In one aspect, the amount of Compound 4 present in the first composition is less than or equal to 45% of the amount of Compound 4 present in the dosage form. In another aspect, the amount of Compound 4 present in the first composition is less than or equal to 40% of the amount of Compound 4 present in the dosage form. In another aspect, the amount of Compound 4 present in the first composition is less than or equal to 35% of the amount of Compound 4 present in the dosage form. In another aspect, the amount of Compound 4 present in the first composition is less than or equal to 30% of the amount of Compound 4 present in the dosage form. In another aspect, the amount of Compound 4 present in the first composition is less than or equal to 25% of the amount of Compound 4 present in the dosage form. In another aspect, the amount of Compound 4 present in the first composition is less than or equal to 20% of the amount of Compound 4 present in the dosage form. In another aspect, the amount of Compound 4 present in the first composition is less than or equal to 15% of the amount of Compound 4 present in the dosage form. In another aspect, the amount of Compound 4 present in the first composition is 25% of the amount of Compound 4 present in the dosage form.

In another embodiment of the dosage form:
the first composition comprises (i) 60 mg to 90 mg (free acid equivalent weight) of Compound 1; (ii) 10 mg to 15 mg (free base equivalent weight) of Compound 2; and (iii) 40 mg to 60 mg (free base equivalent weight) of Compound 3; and
the second composition comprises 225 mg to 450 mg (free acid equivalent weight) of Compound 4.

In another embodiment of the dosage form:
the first composition comprises (i) 70 mg to 80 mg (free acid equivalent weight) of Compound 1; (ii) 11 mg to 14 mg (free base equivalent weight) of Compound 2; and (iii) 45 mg to 55 mg (free base equivalent weight) of Compound 3; and
the second composition comprises 225 mg to 400 mg (free acid equivalent weight) of Compound 4.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the second composition comprises 300 mg to 400 mg (free acid equivalent weight) of Compound 4.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the second composition comprises 300 mg to 400 mg (free acid equivalent weight) of Compound 4; and
the stabilizing polymer comprises copovidone.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the second composition comprises 300 mg to 400 mg (free acid equivalent weight) of Compound 4;
the stabilizing polymer comprises copovidone; and
the release rate-modifying polymer comprises hydroxypropyl methylcellulose.

In another embodiment of the dosage form:
the first composition comprises (i) 60 mg to 90 mg (free acid equivalent weight) of Compound 1; (ii) 10 mg to 15 mg (free base equivalent weight) of Compound 2; and (iii) 40 mg to 60 mg (free base equivalent weight) of Compound 3; and
the first composition further comprises 25 mg to 225 mg (free acid equivalent weight) of Compound 4;
wherein the dosage form comprises a total amount of Compound 4 (free acid equivalent weight) from 225 mg to 450 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 70 mg to 80 mg (free acid equivalent weight) of Compound 1; (ii) 11 mg to 14 mg (free base equivalent weight) of Compound 2; and (iii) 45 mg to 55 mg (free base equivalent weight) of Compound 3; and
the first composition further comprises 25 mg to 225 mg (free acid equivalent weight) of Compound 4;
wherein the dosage form comprises a total amount of Compound 4 (free acid equivalent weight) from 225 mg to 450 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the first composition further comprises 25 mg to 200 mg (free acid equivalent weight) of Compound 4;
wherein the dosage form comprises a total amount of Compound 4 (free acid equivalent weight) from 300 mg to 400 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the first composition further comprises 25 mg to 200 mg (free acid equivalent weight) of Compound 4;
wherein the dosage form comprises a total amount of Compound 4 (free acid equivalent weight) from 300 mg to 400 mg;
the amount of Compound 4 (free acid equivalent weight) in the first composition is less than or equal to the amount of Compound 4 (free acid equivalent weight) in the second composition; and
the stabilizing polymer comprises copovidone.

In another embodiment of the dosage form:
the first composition comprises (i) 75 mg (free acid equivalent weight) of Compound 1; (ii) 12.5 mg (free base equivalent weight) of Compound 2; and (iii) 50 mg (free base equivalent weight) of Compound 3; and
the first composition further comprises 25 mg to 200 mg (free acid equivalent weight) of Compound 4;
wherein the dosage form comprises a total amount of Compound 4 (free acid equivalent weight) from 300 mg to 400 mg;
the amount of Compound 4 (free acid equivalent weight) in the first composition is less than or equal to the amount of Compound 4 (free acid equivalent weight) in the second composition;
the stabilizing polymer comprises copovidone; and
the release rate-modifying polymer comprises hydroxypropyl methylcellulose.

In another embodiment of the dosage form:
the first composition comprises (i) 40 mg to 60 mg (free acid equivalent weight) of Compound 1; (ii) 6.5 mg to 10.5 mg (free base equivalent weight) of Compound 2; and (iii) 25 mg to 40 mg (free base equivalent weight) of Compound 3; and
the second composition comprises 150 mg to 300 mg (free acid equivalent weight) of Compound 4.

In another embodiment of the dosage form:
the first composition comprises (i) 45 mg to 55 mg (free acid equivalent weight) of Compound 1; (ii) 7.5 mg to 9.5 mg (free base equivalent weight) of Compound 2; and (iii) 30 mg to 37 mg (free base equivalent weight) of Compound 3; and
the second composition comprises 150 mg to 300 mg (free acid equivalent weight) of Compound 4.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the second composition comprises 190 mg to 250 mg (free acid equivalent weight) of Compound 4.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the second composition comprises 190 mg to 250 mg (free acid equivalent weight) of Compound 4; and
the stabilizing polymer comprises copovidone.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the second composition comprises 190 mg to 250 mg (free acid equivalent weight) of Compound 4;
the stabilizing polymer comprises copovidone; and
the release rate-modifying polymer comprises hydroxypropyl methylcellulose.

In another embodiment of the dosage form:
the first composition comprises (i) 40 mg to 60 mg (free acid equivalent weight) of Compound 1; (ii) 6.5 mg to 10.5 mg (free base equivalent weight) of Compound 2; and (iii) 25 mg to 40 mg (free base equivalent weight) of Compound 3; and
the first composition further comprises 25 mg to 150 mg (free acid equivalent weight) of Compound 4;
wherein the dosage form comprises a total amount of Compound 4 (free acid equivalent weight) from 150 mg to 300 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 45 mg to 55 mg (free acid equivalent weight) of Compound 1; (ii) 7.5 mg to 9.5 mg (free base equivalent weight) of Compound 2; and (iii) 30 mg to 37 mg (free base equivalent weight) of Compound 3; and
the first composition further comprises 25 mg to 150 mg (free acid equivalent weight) of Compound 4;
wherein the dosage form comprises a total amount of Compound 4 (free acid equivalent weight) from 150 mg to 300 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the first composition further comprises 25 mg to 135 mg (free acid equivalent weight) of Compound 4;
wherein the dosage form comprises a total amount of Compound 4 (free acid equivalent weight) from 190 mg to 250 mg; and
the amount of Compound 4 (free acid equivalent weight) in the first composition is less than or equal to the amount of Compound 4 (free acid equivalent weight) in the second composition.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the first composition further comprises 25 mg to 135 mg (free acid equivalent weight) of Compound 4;
wherein the dosage form comprises a total amount of Compound 4 (free acid equivalent weight) from 190 mg to 250 mg;
the amount of Compound 4 (free acid equivalent weight) in the first composition is less than or equal to the amount of Compound 4 (free acid equivalent weight) in the second composition; and
the stabilizing polymer comprises copovidone.

In another embodiment of the dosage form:
the first composition comprises (i) 50 mg (free acid equivalent weight) of Compound 1; (ii) 8.3 mg (free base equivalent weight) of Compound 2; and (iii) 33.3 mg (free base equivalent weight) of Compound 3; and
the first composition further comprises 25 mg to 135 mg (free acid equivalent weight) of Compound 4;
wherein the dosage form comprises a total amount of Compound 4 (free acid equivalent weight) from 190 mg to 250 mg;
the amount of Compound 4 (free acid equivalent weight) in the first composition is less than or equal to the amount of Compound 4 (free acid equivalent weight) in the second composition;
the stabilizing polymer comprises copovidone; and
the release rate-modifying polymer comprises hydroxypropyl methylcellulose.

D. Compound 4

The dosage form typically will comprise a pharmaceutically acceptable salt of Compound 4. In one aspect, the salt is an alkali metal salt. In another aspect, the salt is a sodium salt. In another aspect, the salt is a crystalline salt. In another aspect, the salt is a pattern B crystalline monosodium salt having an X-ray powder diffraction pattern comprising one or more peaks selected from the group consisting of 5.4±0.2, 10.8±0.2, 14.4±0.2, 16.3±0.2, 17.0±0.2, 21.6±0.2, 22.1±0.2, and 23.7±0.2 degrees two theta when measured at 25° C. with monochromatic Cu-K$_\alpha$1 radiation; or an X-ray powder diffraction pattern comprising one or more peaks selected from the group consisting of 5.4±0.2, 10.8±0.2, 14.4±0.2, 16.3±0.2, 17.0±0.2, 18.8±0.2, 19.2±0.2, 19.6±0.2, 21.6±0.2, 22.1±0.2, 23.7±0.2, 28.8±0.2, 29.1±0.2, and 31.8±0.2 degrees two theta when measured at 25° C. with monochromatic Cu-K$_\alpha$1 radiation; or an X-ray powder diffraction pattern comprising three or more peaks selected from the group consisting of 5.4±0.2, 10.8±0.2, 16.3±0.2, 22.1±0.2, and 23.7±0.2 degrees two theta when measured at 25° C. with monochromatic Cu-K$_\alpha$1 radiation; or an X-ray powder diffraction pattern comprising peaks at 5.4±0.2, 10.8±0.2, 16.3±0.2, and 22.1±0.2 degrees two theta when measured at 25° C. with monochromatic Cu-K$_\alpha$1 radiation. In another aspect, the pattern B monosodium salt is a pattern B monosodium salt monohydrate. In another aspect, the salt is an amorphous salt. In another aspect, the salt is an amorphous monosodium salt.

The amount of Compound 4 (free acid equivalent weight) in the second composition generally is at least 20% by weight of the second composition. In one aspect, the amount of Compound 4 (free acid equivalent weight) in the second composition is at least 25% by weight of the second composition. In another aspect, the amount of Compound 4 (free acid equivalent weight) in the second composition is at least 30% by weight of the second composition. In another aspect, the amount of Compound 4 (free acid equivalent weight) in the second composition is at least 35% by weight of the second composition. In another aspect, the amount of Compound 4 (free acid equivalent weight) in the second composition is at least 40% by weight of the second composition. In another aspect, the amount of Compound 4 (free acid equivalent weight) in the second composition is 20% to 60% percent by weight of the second composition. In another aspect, the amount of Compound 4 (free acid equivalent weight) in the second composition is 25% to 55% percent by weight of the second composition. In another aspect, the amount of Compound 4 (free acid equivalent weight) in the second composition is 35% to 50% percent by weight of the second composition.

E. Stabilizing Polymer

The amount of the stabilizing polymer, or combination of stabilizing polymers, in the second composition generally is at least 5% by weight of the second composition. In one aspect, the amount of the stabilizing polymer, or combination of stabilizing polymers, in the second composition is at least 10% by weight. In another aspect, the amount of the stabilizing polymer, or combination of stabilizing polymers, in the second composition is at least 15% by weight. In another aspect, the amount of the stabilizing polymer, or combination of stabilizing polymers, in the second composition is at least 20% by weight. In another aspect, the amount of the stabilizing polymer, or combination of stabilizing polymers, in the second composition is at least 25% by weight. In another aspect, the amount of the stabilizing polymer, or combination of stabilizing polymers, in the second composition is at least 30% by weight. In another aspect, the amount of the stabilizing polymer, or combination of stabilizing polymers, in the second composition is 10% to 60% percent by weight. In another aspect, the amount of the stabilizing polymer, or combination of stabilizing polymers, in the second composition is 15% to 55% percent by weight. In another aspect, the amount of the stabilizing polymer, or combination of stabilizing polymers, in the second composition is 20% to 50% percent by weight. In another aspect, the amount of the stabilizing polymer, or combination of stabilizing polymers, in the second composition is 25% to 45% percent by weight. In another aspect, the amount of the stabilizing polymer, or combination of stabilizing polymers, in the second composition is 25% to 40% percent by weight.

In one embodiment, the weight ratio of the stabilizing polymer, or combination of stabilizing polymers, to Compound 4 (free acid equivalent weight) in the second composition is from 4:1 to 1:8. In one aspect, the weight ratio of the stabilizing polymer, or combination of stabilizing polymers, to Compound 4 (free acid equivalent weight) in the second composition is 2:1 to 1:4. In another aspect, the weight ratio of the stabilizing polymer, or combination of stabilizing polymers, to Compound 4 (free acid equivalent weight) in the second composition is 1:1 to 1:3.5. In another aspect, the weight ratio of the stabilizing polymer, or combination of stabilizing polymers, to Compound 4 (free acid equivalent weight) in the second composition is 1:1.5 to 1:3.5. In another aspect, the weight ratio of the stabilizing polymer, or combination of stabilizing polymers, to Compound 4 (free acid equivalent weight) in the second composition is 1:2 to 1:3.

When Compound 4 is present in both the first composition and the second composition of the dosage form, the first composition may further comprise a stabilizing polymer, or combination of stabilizing polymers, in the same manner as previously described for the second composition. In such dosage forms, the weight ratio of the stabilizing polymer, or combination of stabilizing polymers, to Compound 4 (free acid equivalent weight) in the first composition is from 4:1 to 1:8, or as otherwise described above for the various aspects of the second composition.

The stabilizing polymer, or combination of stabilizing polymers, selected generally will inhibit precipitation of Compound 4. In one aspect, the stabilizing polymer, or combination of stabilizing polymers, inhibits precipitation of Compound 4 by at least 10% to 80% relative to a substantially identical dosage form that does not contain the stabilizing polymer, or combination of stabilizing polymers. In one aspect, the stabilizing polymer, or combination of stabilizing polymers, inhibits precipitation of Compound 4 by at least 10% relative to a substantially identical dosage form that does not contain the stabilizing polymer, or combination of stabilizing polymers. In another aspect, the stabilizing polymer, or combination of stabilizing polymers, inhibits precipitation of Compound 4 by at least 20%. In another aspect, the stabilizing polymer, or combination of stabilizing polymers, inhibits precipitation of Compound 4 by at least 30%. In another aspect, the stabilizing polymer, or combination of stabilizing polymers, inhibits precipitation of Compound 4 by at least 40%. In another aspect, the stabilizing polymer, or combination of stabilizing polymers, inhibits precipitation of Compound 4 by at least 50%. In another aspect, the stabilizing polymer, or combination of stabilizing polymers, inhibits precipitation of Compound 4 by at least 60%. In another aspect, the stabilizing polymer, or combination of stabilizing polymers, inhibits precipitation of Compound 4 by at least 70%. In another aspect, the stabilizing polymer, or combination of stabilizing polymers, inhibits precipitation of Compound 4 by at least 80%.

In one embodiment, the stabilizing polymer, or combination of stabilizing polymers, selected for the dosage form inhibits precipitation of Compound 4 as determined by the process comprising:
  (a) preparing a test solution comprising Compound 4, or a salt thereof, and the stabilizing polymer, or combination of stabilizing polymers;
  (b) preparing a control solution, the control solution being substantially identical to the test solution except that the control solution does not contain the stabilizing polymer, or combination of stabilizing polymers;
  (c) maintaining the test mixture and the control solution under the same conditions for a test period; and
  (d) determining at the end of the test period the extent to which precipitation of Compound 4, or a salt thereof, is inhibited in the test solution relative to the control solution.

Suitable methods for determining whether precipitation of Compound 4 has been inhibited in the test solution relative to the control solution include UV/Vis spectrophotometry using an in situ UV/Vis probe; HPLC assay of the supernatant solution after removing particles; and other conventional methods known to those of skill in the art.

In one aspect, the stabilizing polymer, or combination of stabilizing polymers, inhibits precipitation of Compound 4 by at least 10% to 80% relative to a substantially identical dosage form that does not contain the stabilizing polymer, or combination of stabilizing polymers, as determined by the process comprising: (a) preparing a test solution comprising Compound 4, or a salt thereof, and the stabilizing polymer, or combination of stabilizing polymers; (b) preparing a control solution, the control solution being substantially identical to the test solution except that the control solution does not contain the stabilizing polymer, or combination of stabilizing polymers; (c) maintaining the test mixture and the control solution under the same conditions for a test period; and (d) determining at the end of the test period the extent to which precipitation of Compound 4, or a salt thereof, is inhibited in the test solution relative to the control solution by UV/Vis spectrophotometry using an in situ UV/Vis probe.

It is hypothesized that in dosage forms comprising a salt of Compound 4 but lacking a sufficient amount of the stabilizing polymer, or combination of stabilizing polymers, the salt is rapidly converted to the relatively insoluble free acid when the salt comes into contact with the acidic environment of the stomach. The free acid then precipitates on the surface of the solid dosage form without being released into the surrounding medium and/or precipitates out of the surrounding medium. This precipitation of the free acid results in a smaller amount of the administered dose of Compound 4 dissolving in the medium and being available for uptake and lowers the overall bioavailability of Compound 4. It is further hypothesized that the incorporation of the stabilizing polymer, or combination of stabilizing polymers, in the dosage form creates a microenvironment in the gastrointestinal tract in which the salt of Compound 4 dissolves to provide the free acid and the stabilizing polymer, or combination of stabilizing polymers, then functions to maintain the free acid in a supersaturated state in solution rather than precipitating out of solution. Because the amount of dissolved free acid increases and free acid precipitation is reduced, a larger amount of the administered dose is absorbed and the bioavailability of Compound 4 is increased.

As a result, the drug loading in a unit dose formulation comprising a salt of Compound 4 and a stabilizing polymer, or combination of stabilizing polymers, can be reduced without a reduction in Compound 4 bioavailability relative to a similar unit dose formulation having a higher drug loading but otherwise lacking a sufficient amount of the stabilizing polymer, or combination of stabilizing polymers. By facilitating a reduction in the required drug loading of the unit dosage form, the stabilizing polymer, or combination of stabilizing polymers, effectively facilitates a corresponding reduction in the size of the unit dosage form where desirable.

Pharmaceutically acceptable stabilizing polymers, or combinations of pharmaceutically acceptable stabilizing polymers, generally will include, for example, compressible stabilizing polymers, or compressible combinations of stabilizing polymers, and non-acidic stabilizing polymers, or non-acidic combinations of stabilizing polymers. In one aspect, the stabilizing polymer, or combination of pharmaceutically acceptable stabilizing polymers, comprises a compressible stabilizing polymer, or compressible combination of stabilizing polymers. In another aspect, the stabilizing polymer, or combination of pharmaceutically acceptable stabilizing polymers, comprises a non-acidic polymer, or non-acidic combination of stabilizing polymers.

Specific pharmaceutically acceptable stabilizing polymers, or combinations of pharmaceutically acceptable stabilizing polymers, include stabilizing polymers, or combinations of stabilizing polymers, selected from the group consisting of copovidone, polyvinylpyrrolidone, hydroxypropyl methylcellulose, polyvinyl caprolactam-polyvinyl acetate-polyethylene glycol graft copolymer (SOLUPLUS®), and combinations thereof; wherein the hydroxypropyl methylcellulose has a viscosity less than 100 centipoise in a 2% solution (i.e., a 2% aqueous solution) at a temperature of 20° C. In one aspect, the stabilizing polymer, or combination of stabilizing polymers, is selected from the group consisting of copovidone, polyvinylpyrrolidone, hydroxypropyl methylcellulose, and combinations thereof; wherein the hydroxypropyl methylcellulose has a viscosity less than 100 centipoise in a 2% solution at a temperature of 20° C. In another aspect, the stabilizing polymer, or combination of stabilizing polymers, is selected from the group consisting of homopolymers or copolymers of N-vinyl pyrrolidone and cellulose esters. In another aspect, the stabilizing polymer, or combination of stabilizing polymers, comprises copovidone. In another aspect, the stabilizing polymer, or combination of stabilizing polymers, comprises polyvinylpyrrolidone. In another aspect, the stabilizing polymer, or combination of stabilizing polymers, comprises hydroxypropyl methylcellulose having a viscosity less than 100 centipoise in a 2% solution at a temperature of 20° C. In another aspect, the stabilizing polymer, or combination of stabilizing polymers, comprises polyvinyl caprolactam-polyvinyl acetate-polyethylene glycol graft copolymer (SOLUPLUS®). In another aspect, the dosage form comprises two or more stabilizing polymers selected from the group consisting of copovidone, polyvinylpyrrolidone, hydroxypropyl methylcellulose, and polyvinyl caprolactam-polyvinyl acetate-polyethylene glycol graft copolymer (SOLUPLUS®); wherein the hydroxypropyl methylcellulose has a viscosity less than 100 centipoise in a 2% solution at a temperature of 20° C.

F. Release Rate-Modifying Polymer

The amount of the release rate-modifying polymer, or combination of release rate-modifying polymers, in the second composition generally is at least 5% by weight of the second composition. In one aspect, the amount of the release rate-modifying polymer, or combination of release rate-modifying polymers, in the second composition is at least 10% by weight. In another aspect, the amount of the release rate-modifying polymer, or combination of release rate-modifying polymers, in the second composition is at least 15% by weight. In another aspect, the amount of the release rate-modifying polymer, or combination of release rate-modifying polymers, in the second composition is at least 20% by weight. In another aspect, the amount of the release rate-modifying polymer, or combination of release rate-modifying polymers, in the second composition is 5% to 60% percent by weight. In another aspect, the amount of the release rate-modifying polymer, or combination of release rate-modifying polymers, in the second composition is 10% to 50% percent by weight. In another aspect, the amount of the release rate-modifying polymer, or combination of release rate-modifying polymers, in the second composition is 15% to 40% percent by weight. In another aspect, the amount of the release rate-modifying polymer, or combination of release rate-modifying polymers, in the second composition is 15% to 30% percent by weight.

In one embodiment, the weight ratio of the release rate-modifying polymer, or combination of release rate-modifying polymers, to Compound 4 (free acid equivalent weight) in the second composition is from 4:1 to 1:8. In one aspect, the weight ratio of the release rate-modifying polymer, or combination of release rate-modifying polymers, to Compound 4 (free acid equivalent weight) in the second composition is 1:4 to 4:1. In another aspect, the weight ratio of the release rate-modifying polymer, or combination of release rate-modifying polymers, to Compound 4 (free acid equivalent weight) in the second composition is the weight ratio of the release rate-modifying polymer, or combination of release rate-modifying polymers, to Compound 4 (free acid equivalent weight) in the second composition is 1:3 to 2:1. In another aspect, the weight ratio of the release rate-modifying polymer, or combination of release rate-modifying polymers, to Compound 4 (free acid equivalent weight) in the second composition is 1:2.5 to 1:1.

Pharmaceutically acceptable release rate-modifying polymers, or combinations of pharmaceutically acceptable release rate-modifying polymers, generally will include, for example, compressible release rate-modifying polymers, or compressible combinations of release rate-modifying polymers, and non-acidic release rate-modifying polymers, or non-acidic combinations of release rate-modifying polymers. In one aspect, the release rate-modifying polymer, or combination of pharmaceutically acceptable release rate-modifying polymers, comprises a compressible release rate-modifying polymer, or compressible combination of release rate-modifying polymers. In another aspect, the release rate-modifying polymer, or combination of pharmaceutically acceptable release rate-modifying polymers, comprises a non-acidic polymer, or non-acidic combination of release rate-modifying polymers.

Specific pharmaceutically acceptable release rate-modifying polymers, or combinations of pharmaceutically acceptable release rate-modifying polymers, include release rate-modifying polymers, or combinations of release rate-modifying polymers, selected from the group consisting of polyvinylpyrolidone, hydroxypropyl methylcellulose, ethylcellulose polymers, copovidone, polyvinyl acetate, methacrylate/methacrylic free acid copolymers, polyethylene glycols, polyethylene oxides, and polaxamers. In one aspect, the release rate-modifying polymers, or combinations of pharmaceutically acceptable release rate-modifying polymers, are selected from the group consisting of polyvinylpyrolidone (such as polyvinylpyrrolidone (PVP) K17, PVP K25, PVP K30, and PVP K90); hydroxypropyl methylcellulose (such as hydroxypropyl methylcellulose (HPMC) E3, HPMC E5, HPMC E6, HPMC E15, HPMC E4M, HPMC E10M, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, and HPMC P550; ethylcellulose polymers (such as Ethocel 4, Ethocel 7, Ethocel 10, Ethocel 14, and Ethocel 20); copovidone (vinylpyrrolidone-vinyl acetate copolymer 60/40), polyvinyl acetate, polyvinyl caprolactam-polyvinyl acetate-polyethylene glycol graft copolymer (SOLUPLUS®), methacrylate/methacrylic free acid copolymers (such as Eudragit L100-55, Eudragit L100, and Eudragit S100); polyethylene glycols (such as polyethylene glycol (PEG) 400, PEG 600, PEG 1450, PEG 3350, PEG 4000, PEG 6000, and PEG 8000); and polaxamers (such as poloxamer 124, poloxamer 188, poloxamer 237, poloxamer 338, and poloxamer 407). In another aspect, the release rate-modifying polymer, or combination of release rate-modifying polymers, is selected from the group consisting of copovidone, polyvinylpyrrolidone, and hydroxypropyl methylcellulose. In another aspect, the release rate-modifying polymer, or combination of release rate-modifying polymers, comprises hydroxypropyl methylcellulose. In another aspect, the release rate-modifying polymer, or combination of release rate-modifying polymers, comprises hydroxypropyl methylcellulose giving an apparent viscosity at 2% weight in water at 20° C. of 80 centipoise to 120,000 centipoise at 20° C. In another aspect, the release rate-modifying polymer, or combination of release rate-modifying polymers, comprises a hydroxypropyl methylcellulose selected from the group consisting of K100, K4M, K15M, and K100M hydroxypropyl methylcelluloses.

In one embodiment of the dosage forms of the present disclosure, the stabilizing polymer comprises copovidone and the release rate-modifying polymer comprises hydroxypropyl methylcellulose.

G. Granulation

The Compound 4 starting material employed in the preparation of the dosage form can be granulated or ungranulated. It may be beneficial to use granulated Compound 4, for example, to improve bulk handling properties of the Compound 4 starting material during the preparation of the dosage form. In one embodiment, at least a portion of the Compound 4 used in the preparation of the dosage form (e.g., as the Compound 4 starting material for the first composition, the second composition, or both) is provided in the form of granules comprising Compound 4, wherein the granules are prepared by granulating Compound 4 with at least a portion of one or more of the excipients (see Section II.I. below) present in the dosage form.

In one embodiment, the dosage form is prepared by a process comprising:
  granulating (i) a mixture comprising at least a portion of the Compound 4 with at least a portion of the stabilizing polymer, or combination of stabilizing polymers, to provide granules comprising Compound 4; (ii) a mixture comprising at least a portion of the Compound 4 with at least a portion of the release rate-modifying polymer, or combination of release rate-modifying polymers, to provide granules comprising Compound 4; or (iii) a mixture comprising at least a portion of the Compound 4 with at least a portion of the stabilizing polymer, or combination of stabilizing polymers, and at least a portion of the release rate-modifying polymer, or combination of stabilizing polymers, to provide granules comprising Compound 4; and
  preparing the second composition using the granules as a source of at least a portion of the Compound 4 present in the second composition.

As previously discussed, a portion of the total amount of Compound 4 in the dosage form also may be present in the first composition. In such dosage forms, at least a portion of the Compound 4 used in the preparation of the first composition can be provided in the form of granules comprising Compound 4, wherein the granules are prepared by granulating Compound 4 with at least a portion of the stabilizing polymer, or combination of stabilizing polymers. In one embodiment, the dosage form is prepared by a process comprising:
  granulating a mixture comprising at least a portion of the Compound 4 with at least a portion of the stabilizing polymer, or combination of stabilizing polymers, to provide granules comprising Compound 4; and
  preparing the first composition using the granules as a source of at least a portion of the Compound 4 present in the first composition.

In another embodiment, the dosage form is prepared by a process comprising:
  granulating a mixture comprising at least a portion of the Compound 4 with at least a portion of the stabilizing polymer, or combination of stabilizing polymers, to provide granules comprising Compound 4;
  preparing the first composition using the granules as a source of at least a portion of the Compound 4 present in the first composition; and
  preparing the second composition using the granules as a source of at least a portion of the Compound 4 present in the second composition.

In another embodiment, the dosage form is prepared by a process comprising:
- granulating (i) a mixture comprising at least a portion of the Compound 4 with at least a portion of the stabilizing polymer, or combination of stabilizing polymers, to provide a first population of granules comprising Compound 4;
- granulating (i) a mixture comprising at least a portion of the Compound 4 with at least a portion of the release rate-modifying polymer, or combination of release rate-modifying polymers, to provide a second population of granules comprising Compound 4; or (ii) a mixture comprising at least a portion of the Compound 4 with at least a portion of the stabilizing polymer, or combination of stabilizing polymers, and at least a portion of the release rate-modifying polymer, or combination of stabilizing polymers, to provide a second population of granules comprising Compound 4;
- preparing the first composition using the first population of granules as a source of at least a portion of the Compound 4 present in the first composition; and
- preparing the second composition using the second population of granules as a source of at least a portion of the Compound 4 present in the second composition.

In another embodiment, at least a portion of the Compound 4 is dry granulated during the preparation of the dosage form with at least a portion of one or more of the excipients that are present in the final dosage form.

In another embodiment, at least a portion of the Compound 4 is wet granulated during the preparation of the dosage form with at least a portion of one or more of the excipients that are present in the final dosage form. In one aspect, at least a portion of the Compound 4 is wet (high shear) granulated with at least a portion of one or more of the excipients that are present in the final dosage form. In another aspect, a liquid comprising water is added to the granulation mixture during wet granulation.

In another embodiment, at least a portion of the Compound 4 is fluid bed granulated during the preparation of the dosage form with at least a portion of one or more of the excipients that are present in the final dosage form. In one aspect, a liquid comprising water is added to the granulation mixture during the fluid bed granulation. In another aspect, the granulation mixture is sprayed with a liquid comprising water during the fluid bed granulation.

In general, the moisture content of the granulation mixture during fluid bed granulation is controlled to provide an acceptable level of adhesion between the Compound 4 particles and the copovidone particles. As the weight ratio of Compound 4 to total polymer in the granulation mixture increases (i.e., as the relative amount of Compound 4 present in the granulation mixture increases), the target moisture content selected for the granulation mixture during granulation typically will increase. In addition, it may be beneficial to maintain the granulation mixture in the fluid bed at the specified moisture content for an additional period of time (i.e., a "hold period") to further facilitate additional growth, tighter particle size distribution, and/or improved mechanical properties of the granules. In one aspect, the granulation mixture comprises no more than 20 weight percent liquid during the granulation. In another aspect, the granulation mixture comprises no more than 14 weight percent liquid during the granulation. In another aspect, the granulation mixture comprises from 5 weight percent liquid to 20 weight percent liquid when the addition of the liquid to the granulation mixture has been completed (i.e., prior to drying the granulation mixture). In another aspect, the granulation mixture comprises from 8 weight percent liquid to 14 weight percent liquid when the addition of the liquid to the granulation mixture has been completed.

In each and every embodiment, example, preference and aspect described herein, at least a portion of the Compound 4 can be, for example, fluid bed granulated with (a) at least a portion of the pharmaceutically acceptable stabilizing polymer, or combination of pharmaceutically acceptable stabilizing polymers, and/or (b) at least a portion of the pharmaceutically acceptable release rate-modifying polymer, or combination of pharmaceutically acceptable stabilizing polymers, prior to blending with the other components of the formulation; and the weight ratio of Compound 4 (free acid equivalent weight) to total polymer (i.e., the combined weight of stabilizing polymer and release rate-modifying polymer) in the resulting granules is from 4:1 to 1:8.

In each and every embodiment, example, preference and aspect described herein, the Compound 4 starting material used in the granulation can, for example, have a particle size distribution that satisfies one or more of the following conditions: (a) a $D_{10}$ particle size distribution less than 20 µm, (b) a $D_{50}$ particle size distribution less than 50 µm, and/or (c) a $D_{90}$ particle size distribution less than 150 µm. In one aspect, the Compound 4 starting material has a $D_{90}$ particle size distribution less than 100 µm. In another aspect, the Compound 4 starting material has a particle size distribution that satisfies one or more of the following conditions: (a) a $D_{10}$ particle size distribution from 1 µm to 20 µm, (b) a $D_{50}$ particle size distribution from 10 µm to 50 µm, and/or (c) a $D_{90}$ particle size distribution from 40 µm to 100 µm.

In each and every embodiment, example, preference, and aspect described herein, the granules comprising Compound 4 can, for example, have a particle size distribution after granulation, sieving, and/or milling and prior to compression that satisfies one or more of the following conditions: (a) a $D_{10}$ particle size distribution less than 100 µm, (b) a $D_{50}$ particle size distribution less than 300 µm, and/or (c) a $D_{90}$ particle size distribution less than 600 µm. In one aspect, the granules comprising Compound 4 have a particle size distribution after granulation, sieving, and/or milling and prior to compression that satisfies one or more of the following conditions: (a) a $D_{10}$ particle size distribution from 1 µm to 100 µm, (b) a $D_{50}$ particle size distribution from 40 µm to 300 µm, and/or (c) a $D_{90}$ particle size distribution from 100 µm to 600 µm. In another aspect, the Compound 4 granules have a particle size distribution after granulation, sieving, and/or milling and prior to compression that satisfies one or more of the following conditions: (a) a $D_{10}$ particle size distribution from 5 µm to 50 µm, (b) a $D_{50}$ particle size distribution from 80 µm to 130 µm, and/or (c) a $D_{90}$ particle size distribution from 180 µm to 250 µm.

Further discussion on granulation unit operations can be found, for example, in Food and Drug Administration Guidance for Industry, SUPAC-IR/MR: Immediate Release and Modified Release Solid Oral Dosage Forms, Manufacturing Equipment Addendum (January 1999, CMC 9, Revision 1).

H. Compounds 1, 2, and 3

The total drug loading in the first composition of the dosage form generally will be at least 5% by weight of the first composition. In one aspect, the total amount of Compound 1 (free acid equivalent weight), Compound 2 (free base equivalent weight), and Compound 3 (free base equivalent weight) in the first composition is at least 6% by weight of the first composition. In another aspect, the total amount is at least 8% by weight. In another aspect, the total amount is at least 10% by weight. In another aspect, the total amount is at least 12% by weight. In another aspect, the total amount is 6% to 15% percent by weight. In another aspect, the total amount is 8% to 15% percent by weight. In another aspect, the total amount is 10% to 40% percent by weight. In another aspect, the total amount is 15% to 30% percent by weight. In another aspect, the total amount is 15% to 25% percent by weight. In another aspect, the total amount is 20% to 30% percent by weight. In another aspect, the first composition comprises Compound 1, Compound 2, and Compound 3 at a weight ratio (free acid or free base) of 3:2:24 to 60:3:5 (Compound 1:Compound 2:Compound 3). In another aspect, the first composition comprises Compound 1, Compound 2, and Compound 3 at a weight ratio (free acid or free base) of 10:1:2 to 2:1:3 (Compound 1:Compound 2:Compound 3). In another aspect, the weight ratio is 6:1:4 (Compound 1:Compound 2:Compound 3).

In order to achieve the desired total drug loading, the first composition typically will comprise Compound 1, Compound 2, and Compound 3 in the form of an amorphous solid dispersion. In one embodiment, separate amorphous solid dispersions are prepared for each of Compound 1, Compound 2, and Compound 3 (e.g., individual mono-extrudates) and the separate amorphous solid dispersions are used to prepare the first composition. In another embodiment, a single amorphous solid dispersion comprising Compound 1, Compound 2, and Compound 3 (e.g., a co-extrudate) is prepared and used to prepare the first composition.

1. Individual Mono-Extrudates

In one embodiment of the present disclosure, each of the Compound 1, Compound 2, and Compound 3 components of the first composition is prepared as a separate amorphous solid dispersion comprising the active ingredient using hot melt extrusion technology and is milled prior to blending with the other two amorphous dispersions to form the first composition. Accordingly, in one aspect of the dosage form, the first composition comprises particles of a first amorphous solid dispersion comprising Compound 1; particles of a second amorphous solid dispersion comprising Compound 2; and particles of a third amorphous solid dispersion comprising Compound 3. In another aspect, the first amorphous solid dispersion, second amorphous solid dispersion, and the third amorphous solid dispersion each independently comprise at least one pharmaceutically acceptable hydrophilic polymer and at least one pharmaceutically acceptable surfactant. In another aspect, each hydrophilic polymer has a $T_g$ value of at least 50° C. In another aspect, each hydrophilic polymer is a homopolymer or copolymer of N-vinyl pyrrolidone. In another aspect, the hydrophilic polymer is copovidone. In another aspect, each surfactant has a Hydrophilic-Lipophilic Balance value of at least 10. In another aspect, one or more of the first amorphous solid dispersion, second amorphous solid dispersion, and the third amorphous solid dispersion further comprises another surfactant having a Hydrophilic-Lipophilic Balance value of below 10. In another aspect, the first amorphous solid dispersion comprises propylene glycol monolaurate as the surfactant. In another aspect, the first amorphous solid dispersion further comprises vitamin E tocopheryl polyethylene glycol succinate. In another aspect, the second amorphous solid dispersion comprises vitamin E tocopheryl polyethylene glycol succinate as the surfactant. In another aspect, the third amorphous solid dispersion comprises sorbitan monolaurate as the surfactant.

Additional information regarding the preparation of a Compound 1 mono-extrudate, a Compound 2 mono-extrudate, and a Compound 3 mono-extrudate can be found, for example, in published U.S. application US2011/0312973 and published international application WO2011/156578, both of which are incorporated by reference.

2. Co-Extrudate

In another embodiment of the present disclosure, Compound 1, Compound 2, and Compound 3 are prepared as a single amorphous solid dispersion comprising those three active ingredients using hot melt extrusion technology. The amorphous solid dispersion is milled and used to prepare the first composition.

Drug loads in conventional amorphous solid dispersions of poorly soluble compounds are generally no more than 15% by weight because higher drug loads can lead to a substantial reduction in drug release. Consequently, the Triple Tablet used in clinical trials was prepared from separate solid dispersions of Compound 1, Compound 2, and Compound 3, with each of the three solid dispersions having no more than 15% drug loading. As a result of the low drug loading, the Triple Tablet was relatively large in size.

Moreover, hot melt extrusion, a method commonly used to prepare amorphous solid dispersions, often involves the use of high temperature to assist the formation of a melt that is composed of all components of the final solid dispersion. Certain drug substances, such as Compound 3, can reach unacceptable degradation levels at temperatures of beyond 140° C., which considerably limits the use of the hot melt extrusion process to co-formulate Compound 3 with other drug substance(s) when the other drug substance(s) requires higher temperatures to form a suitable melt.

In contrast to conventional understanding, however, it has been found that Compound 1, Compound 2, and Compound 3 can be co-formulated in an amorphous solid dispersion having an increased total drug loading without compromising drug release. This allows the preparation of smaller solid dosage forms (e.g., tablets) comprising all three drug substances. In addition, when Compound 1, Compound 2, and Compound 3 were co-extruded in the hot melt extrusion process, Compound 3 became less susceptible to degradation at high temperatures. Even at a temperature of 165° C., Compound 3 degradation was well within the acceptable levels.

In one embodiment of the present disclosure, the total weight of Compound 1, Compound 2, and Compound 3 in the amorphous solid dispersion is at least 6% by weight relative to the total weight of the amorphous solid dispersion. In one aspect, the total weight is at least 8% by weight relative to the total weight of the amorphous solid dispersion. In another aspect, the total weight is at least 10% by weight relative to the total weight of the amorphous solid dispersion. In another aspect, the total weight is at least 12% by weight relative to the total weight of the amorphous solid dispersion. In another aspect, the total weight is at least 15% by weight relative to the total weight of the amorphous solid dispersion. In another aspect, the total weight is in excess of 15% by weight relative to the total weight of the amorphous solid dispersion. In another aspect, the total weight ranges from 10% to 40% by weight relative to the total weight of the amorphous solid dispersion. In another aspect, the total weight ranges from 15% to 40% by weight relative to the total weight of the amorphous solid dispersion. In another aspect, the total weight ranges from 20% to 40% by weight relative to the total weight of the amorphous solid dispersion. In another aspect, the total weight ranges from 20% to 30% by weight relative to the total weight of the amorphous solid dispersion. In another aspect, the total weight ranges from 25% to 30% by weight relative to the total weight of the amorphous solid dispersion.

In another embodiment, Compound 1 in the amorphous solid dispersion can range from 10% to 20% by weight relative to the total weight of the amorphous solid dispersion; Compound 2 in the amorphous solid dispersion can range from 2% to 5% by weight relative to the total weight of the amorphous solid dispersion; and Compound 3 in the amorphous solid dispersion can range from 5% to 15% by weight relative to the total weight of the amorphous solid dispersion. In one aspect, Compound 1 in the amorphous solid dispersion can range from 15% to 20% by weight relative to the total weight of the amorphous solid dispersion; Compound 2 in the amorphous solid dispersion can range from 2% to 3% by weight relative to the total weight of the amorphous solid dispersion; and Compound 3 in the amorphous solid dispersion can range from 10% to 15% by weight relative to the total weight of the amorphous solid dispersion. In another aspect, Compound 1 in the amorphous solid dispersion can be 15% by weight relative to the total weight of the amorphous solid dispersion; Compound 2 in the amorphous solid dispersion can range from 2% to 3% by weight relative to the total weight of the amorphous solid dispersion; and Compound 3 in the amorphous solid dispersion can be 10% by weight relative to the total weight of the amorphous solid dispersion.

In another embodiment, the amount of Compound 1 in the amorphous solid dispersion can be, for example, 75 mg; the amount of Compound 2 in the amorphous solid dispersion can be, for example, 12.5 mg; and the amount of Compound 3 in the amorphous solid dispersion can be, for example, 50 mg.

In another embodiment, the amorphous solid dispersion can comprise from 50% to 75% by weight, relative to the total weight of the amorphous solid dispersion, of the polymer, and from 2% to 15% by weight, relative to the total weight of the amorphous solid dispersion, of the surfactant. In one aspect, the amorphous solid dispersion can comprise from 50% to 70% by weight, relative to the total weight of the amorphous solid dispersion, of the polymer, and from 5% to 15% by weight, relative to the total weight of the amorphous solid dispersion, of the surfactant. In another aspect, the amorphous solid dispersion can comprise from 55% to 65% by weight, relative to the total weight of the amorphous solid dispersion, of the polymer, and from 5% to 10% by weight, relative to the total weight of the amorphous solid dispersion, of the surfactant. In another aspect, the amorphous solid dispersion can comprise from 60% to 65% by weight, relative to the total weight of the amorphous solid dispersion, of the polymer, and from 5% to 10% by weight, relative to the total weight of the amorphous solid dispersion, of the surfactant.

In another embodiment, the amorphous solid dispersion can be prepared as a compressed core (e.g., a tablet core, layer, or the like), onto which another layer of other excipients or ingredients can be optionally added. For example, the amorphous solid dispersion can be milled, mixed with other excipients or ingredients to form the first composition, and the first composition compressed to form the core. In one aspect, the polymer in the amorphous solid dispersion can range from 50% to 75% by weight relative to the total weight of the compressed core, and the surfactant in the amorphous solid dispersion can range from 5 to 15% by weight relative to the total weight of the compressed core. In another aspect, the polymer in the amorphous solid dispersion can range from 50% to 70% by weight relative to the total weight of the compressed core, and the surfactant in the amorphous solid dispersion can range from 5 to 15% by weight relative to the total weight of the compressed core. In another aspect, the polymer in the amorphous solid dispersion can range from 55% to 65% by weight relative to the total weight of the compressed core, and the surfactant in the amorphous solid dispersion can range from 5 to 10% by weight relative to the total weight of the compressed core. In another aspect, the polymer in the amorphous solid dispersion can range from 60% to 65% by weight relative to the total weight of the compressed core, and the surfactant in the amorphous solid dispersion can range from 5 to 10% by weight relative to the total weight of the compressed core.

In another embodiment, the total weight of Compound 1, Compound 2, and Compound 3 in the amorphous solid dispersion can range from 20% to 40% by weight relative to the total weight of the compressed core. In one aspect, the total weight of Compound 1, Compound 2, and Compound 3 in the amorphous solid dispersion can range from 20% to 30% by weight relative to the total weight of the compressed core. In another aspect, the total weight of Compound 1, Compound 2, and Compound 3 in the amorphous solid dispersion can range from 25% to 30% by weight relative to the total weight of the compressed core. In another aspect, Compound 1 in the amorphous solid dispersion can range from 10% to 20% by weight relative to the total weight of the compressed core; Compound 2 in the amorphous solid dispersion can range from 2% to 5% by weight relative to the total weight of the compressed core; and Compound 3 in the amorphous solid dispersion can range from 5% to 15% by weight relative to the total weight of the compressed core. In another aspect, Compound 1 in the amorphous solid dispersion can range from 15% to 20% by weight relative to the total weight of the compressed core; Compound 2 in the amorphous solid dispersion can range from 2% to 3% by weight relative to the total weight of the compressed core; and Compound 3 in the amorphous solid dispersion can range from 10% to 15% by weight relative to the total weight of the compressed core. In another aspect, Compound 1 in the amorphous solid dispersion can be 15% by weight relative to the total weight of the compressed core; Compound 2 in the amorphous solid dispersion can range from 2% to 3% by weight relative to the total weight of the compressed core; and Compound 3 in the amorphous solid dispersion can be 10% by weight relative to the total weight of the compressed core.

In another embodiment, the hydrophilic polymer can have a $T_g$ of at least 50° C. In one aspect, the hydrophilic polymer has a $T_g$ of at least 80° C. In another aspect, the hydrophilic polymer has a $T_g$ of at least 100° C. In another aspect, the hydrophilic polymer can have a $T_g$ of from 80° C. to 180° C. In another aspect, the hydrophilic polymer can have a $T_g$ of from 100° C. to 150° C.

Although the first composition can comprise a poorly water-soluble or water-insoluble polymer (such as a cross-linked polymer), the first composition generally will comprise a hydrophilic polymer that is a water-soluble polymer. In one aspect, the hydrophilic polymer has an apparent viscosity, when dissolved at 20° C. in an aqueous solution at 2% (w/v), of 1 to 5000 mPa·s. In another aspect, the hydrophilic polymer has an apparent viscosity, when dissolved at 20° C. in an aqueous solution at 2% (w/v), of 1 to 700 mPa·s. In another aspect, the hydrophilic polymer has an apparent viscosity, when dissolved at 20° C. in an aqueous solution at 2% (w/v), of 5 to 100 mPa·s.

The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, polysaccharide, or combinations thereof. Non-limiting examples of suitable hydrophilic polymers include homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropyl methylcellulose, cellulose phthalate, cellulose succinate, cellulose acetate phthalate, hydroxypropyl methylcellulose phthalate, hydroxypropyl methylcellulose succinate, hydroxypropyl methylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, xanthan gum, and combinations thereof. In one aspect, the hydrophilic polymer is copovidone. In another aspect, the hydrophilic polymer is a homopolymer or copolymer of N-vinyl pyrrolidone.

Although the first composition can comprise a surfactant having a Hydrophobic-Lipophilic Balance ("HLB") value less than 10, the first composition generally will comprise a surfactant having an HLB value of at least 10. In one embodiment, the first composition comprises a first surfactant having an HLB of at least 10 and a second surfactant having an HLB value of less than 10, and both surfactants are co-formulated in the amorphous solid dispersion.

The surfactant can be selected, for example, from the group consisting of polyoxyethylene castor oil derivates, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, sorbitan fatty acid mono ester, and combinations thereof. Non-limiting examples of suitable surfactants include polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60), mono fatty acid ester of polyoxyethylene sorbitan, such as mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40) or polyoxyethylene (20) sorbitan monolaurate (Tween® 20), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate (e.g., Lauroglycol), sucrose monostearate, sucrose distearate, sucrose monolaurate, sucrose dilaurate, sorbitan monolaurate, sorbitan monooleate, sorbitan monopalnitate, sorbitan stearate, or combinations thereof. In one aspect, the surfactant is D-alpha-tocopheryl polyethylene glycol 1000 succinate (vitamin E TPGS).

In one embodiment, the polymer is copovidone, and the surfactant is vitamin E TPGS. In another aspect, the polymer is copovidone, the surfactant is vitamin E TPGS, and the amorphous solid dispersion further comprises propylene glycol monolaurate (e.g., Lauroglycol). Propylene glycol monolaurate can range, for example, from 1% to 5% by weight relative to the total weight of the amorphous solid dispersion. Propylene glycol monolaurate can also range, for example, from 1% to 3% by weight relative to the total weight of the amorphous solid dispersion.

In another embodiment, first composition comprises 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the polymer in the amorphous solid dispersion ranges from 50% to 70% by weight relative to the total weight of the amorphous solid dispersion, and the surfactant in the amorphous solid dispersion ranges from 5% to 15% by weight relative to the total weight of the amorphous solid dispersion. In one aspect, the polymer is copovidone, and the surfactant is vitamin E TPGS. In another aspect, the amorphous solid dispersion further comprises from 1% to 5% by weight of propylene glycol monolaurate, relative to the total weight of the amorphous solid dispersion. In another aspect, the amorphous solid dispersion further comprises from 1% to 3% by weight of propylene glycol monolaurate.

In another embodiment, the first composition comprises 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the polymer in the amorphous solid dispersion ranges from 55% to 65% by weight relative to the total weight of the amorphous solid dispersion, and the surfactant in the amorphous solid dispersion ranges from 5% to 10% by weight relative to the total weight of the amorphous solid dispersion. In one aspect, the polymer is copovidone, and the surfactant is vitamin E TPGS. In another aspect, the amorphous solid dispersion further comprises from 1% to 5% by weight of propylene glycol monolaurate, relative to the total weight of the amorphous solid dispersion. In another aspect, the amorphous solid dispersion further comprises from 1% to 3% by weight of propylene glycol monolaurate.

In another embodiment, the first composition comprises 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the polymer in the amorphous solid dispersion ranges from 60% to 65% by weight relative to the total weight of the amorphous solid dispersion, and the surfactant in the amorphous solid dispersion ranges from 5% to 10% by weight relative to the total weight of the amorphous solid dispersion. In one aspect, the polymer is copovidone, and the surfactant is vitamin E TPGS. In another aspect, the amorphous solid dispersion further comprises from 1% to 5% by weight of propylene glycol monolaurate, relative to the total weight of the amorphous solid dispersion. In another aspect, the amorphous solid dispersion further comprises from 1% to 3% by weight of propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core is no more than 800 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core is no more than 700 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core is no more than 600 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core is no more than 500 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core ranges from 400 mg to 500 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core ranges from 500 mg to 600 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core ranges from 600 mg to 700 mg. In one aspect, the polymer is copovidone, and the surfactant is vitamin E TPGS, and the amorphous solid dispersion further comprises propylene glycol monolaurate In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core ranges from 450 mg to 500 mg. In one aspect, the polymer is copovidone, and the surfactant is vitamin E TPGS, and the amorphous solid dispersion further comprises propylene glycol monolaurate.

In another embodiment, the first composition comprises a compressed core which includes 75 mg of Compound 1, 12.5 mg of Compound 2, and 50 mg of Compound 3, all of which are co-formulated with a pharmaceutically acceptable hydrophilic polymer and a pharmaceutically acceptable surfactant in amorphous solid dispersion, wherein the total weight of the compressed core is 500 mg. In one aspect, the polymer is copovidone, and the surfactant is vitamin E TPGS, and the amorphous solid dispersion further comprises propylene glycol monolaurate.

In one embodiment, the amorphous solid dispersion is a solid solution, glass solution, or glass suspension. These types of amorphous solid dispersions are discussed, for example, in Chiou, W. L. and Riegelman, S. (1971), Pharmaceutical applications of solid dispersion systems. J. Pharm. Sci., 60: 1281-1302. In one aspect, the amorphous solid dispersion is a solid solution. In another embodiment, the amorphous solid dispersion is a glassy solution.

In another embodiment, the amorphous solid dispersion comprises or consists of a single-phase (as defined in thermodynamics) in which Compound 1, Compound 2, and Compound 3 are molecularly dispersed in a matrix containing the pharmaceutically acceptable hydrophilic polymer and the pharmaceutically acceptable surfactant. Thermal analysis of the amorphous solid dispersion using differential scanning calorimetry (DSC) typically shows only one single $T_g$, and the amorphous solid dispersion typically does not contain any detectable crystalline compound as measured by X-ray powder diffraction spectroscopy.

I. Additional Excipients

The dosage form optionally may comprise other excipients such as, for example, fillers, disintegrants, glidants, and lubricants. The term "excipient" is used in this disclosure to describe any ingredient other than Compound 1, Compound 2, Compound 3, or Compound 4. The choice of additional excipient(s) will depend to a large extent on factors such as, for example, the effect of the excipient on solubility and stability. The drug loading requirements and resulting dosage form size, however, may effectively limit the amount of additional excipients that may be included in the dosage form.

Examples of pharmaceutically acceptable fillers include, without limitation, microcrystalline cellulose, such as Avicel PH 101, Avicel PH102, Avicel PH 200, Avicel PH 105, Avicel DG, Ceolus KG 802, Ceolus KG 1000, SMCC50 and Vivapur 200; lactose monohydrate, such as Lactose FastFlo; microcrystalline cellulose co-processed with other excipeints, such as microcrystalline cellulose co-processed with lactose monohydrate (MicroceLac 100) and microcrystalline cellulose co-processed with colloidal silicon dioxide (SMCC50, Prosolv 50 and Prosolv HD 90); mixtures of isomaltulose derivatives such as galenIQ; natural or pre-gelatinized potato or corn starch; and other suitable fillers and combinations thereof.

Examples of pharmaceutically acceptable disintegrants include, without limitation, cross-linked polymers such as cross-linked polyvinyl pyrrolidone and cross-linked sodium carboxymethylcellulose (including croscarmellose sodium).

Examples of pharmaceutically acceptable glidants include, without limitation, colloidal silicon dioxide (such as highly dispersed silica (Aerosil®)) and any other suitable glidant such as animal or vegetable fats or waxes.

Examples of pharmaceutically acceptable lubricants include, without limitation, polyethylene glycol (e.g., having a molecular weight of from 1000 to 6000), magnesium stearate, calcium stearate, sodium stearyl fumarate, and talc.

J. In vitro and In vivo Properties of Dosage Form

1. In Vitro Properties

In one aspect, the pharmaceutically acceptable release rate-modifying polymer, or combination of pharmaceutically acceptable release rate-modifying polymers, modifies an in vitro release rate from the dosage form of at least one of the compounds within the dosage form to be less than 75% to less than 35% of the in vitro release rate of the compound from an otherwise identical dosage form lacking the release rate-modifying polymer, or combination of release rate-modifying polymers.

In one aspect, the pharmaceutically acceptable release rate-modifying polymer, or combination of pharmaceutically acceptable release rate-modifying polymers, modifies an in vitro release rate from the dosage form of at least one of the compounds within the dosage form to be less than 75% to less than 35% of the in vitro release rate of the compound from an otherwise identical dosage form lacking the release rate-modifying polymer, or combination of release rate-modifying polymers as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

In one aspect, the pharmaceutically acceptable release rate-modifying polymer, or combination of pharmaceutically acceptable release rate-modifying polymers, modifies an in vitro release rate from the dosage form of at least one of the compounds within the dosage form to be an average in vitro release rate for the compound of 1.0 weight percent/hour (based on the total weight of the compound in the dosage form) to 6.0 weight percent/hour over a sixteen-hour period. In one aspect, the pharmaceutically acceptable release rate-modifying polymer, or combination of pharmaceutically acceptable release rate-modifying polymers, modifies an in vitro release rate from the dosage form of at least one of the compounds within the dosage form to be an average in vitro release rate for the compound of 1.0 weight percent/hour (based on the total weight of the compound in the dosage form) to 6.0 weight percent/hour over a sixteen-hour period as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

In one aspect, the pharmaceutically acceptable release rate-modifying polymer, or combination of pharmaceutically acceptable release rate-modifying polymers, modifies an in vitro release rate from the dosage form of at least one of the compounds within the dosage form to be an average in vitro release rate for the compound of 5 mg/hour to 16 mg/hour over a sixteen-hour period.

In one aspect, the pharmaceutically acceptable release rate-modifying polymer, or combination of pharmaceutically acceptable release rate-modifying polymers, modifies an in vitro release rate from the dosage form of at least one of the compounds within the dosage form to be an average in vitro release rate for the compound of 5 mg/hour to 16 mg/hour over a sixteen-hour period as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

a. Compound 4

In one aspect, the pharmaceutically acceptable release rate-modifying polymer, or combination of pharmaceutically acceptable release rate-modifying polymers, modifies an in vitro release rate of Compound 4 from the dosage form to be less than less than 75% to less than 35% of the in vitro release rate of Compound 4 from an otherwise identical dosage form lacking the release rate-modifying polymer, or combination of release rate-modifying polymers.

In one embodiment, the dosage forms of the present disclosure exhibit an in vitro release rate that is less than 75% of the in vitro release rate exhibited by an otherwise identical dosage form lacking the release rate-modifying polymer, or combination of release rate-modifying polymers, wherein the in vitro release rate is determined using the dissolution test described below in Section II.J.1.c, and represents the average in vitro release rate (mg/hour) for Compound 4 over a four-hour period. In one aspect, the in vitro release rate is less than 65% of the in vitro release rate exhibited by an otherwise identical dosage form lacking the release rate-modifying polymer, or combination of release rate-modifying polymers. In another aspect, the in vitro release rate is less than 55% of the in vitro release rate exhibited by an otherwise identical dosage form lacking the release rate-modifying polymer, or combination of release rate-modifying polymers. In another aspect, the in vitro release rate is less than 45% of the in vitro release rate exhibited by an otherwise identical dosage form lacking the release rate-modifying polymer, or combination of release rate-modifying polymers. In another aspect, the in vitro release rate is less than 35% of the in vitro release rate exhibited by an otherwise identical dosage form lacking the release rate-modifying polymer, or combination of release rate-modifying polymers. In one aspect, the pharmaceutically acceptable release rate-modifying polymer, or combination of pharmaceutically acceptable release rate-modifying polymers, modifies an in vitro release rate of Compound 4 from the dosage form to be an average in vitro release rate for of Compound 4 of 1.0 weight percent/hour (based on the total weight of the compound in the dosage form) to 6.0 weight percent/hour over a sixteen-hour period.

In another embodiment, the dosage forms of the present disclosure exhibit an average in vitro release rate for Compound 4 over a 16 hour period of 1.0 weight percent/hour (based on the total weight of Compound 4 in the dosage form) to 6.0 weight percent/hour as determined using the dissolution test described below in Section II.J.1.c. In one aspect, the average in vitro release rate over a 16 hour period is 1.5 weight percent/hour to 5.5 weight percent/hour. In another aspect, the average in vitro release rate over a 16 hour period is 2.0 weight percent/hour to 5.0 weight percent/hour. In another aspect, the average in vitro release rate over a 16 hour period is 2.0 weight percent/hour to 4.5 weight percent/hour. In another aspect, the average in vitro release rate over a 16 hour period is 2.0 weight percent/hour to 4.0 weight percent/hour. In another aspect, the average in vitro release rate over a 16 hour period is 3.0 weight percent/hour to 3.5 weight percent/hour.

In one aspect, the pharmaceutically acceptable release rate-modifying polymer, or combination of pharmaceutically acceptable release rate-modifying polymers, modifies an in vitro release rate of Compound 4 from the dosage form to be an average in vitro release rate for the compound over a 16 hour period of 1.0 weight percent/hour (based on the total weight of Compound 4 in the dosage form) to 6.0 weight percent/hour as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C. In one aspect, the pharmaceutically acceptable release rate-modifying polymer, or combination of pharmaceutically acceptable release rate-modifying polymers, modifies an in vitro release rate of Compound 4 from the dosage form to be an average in vitro release rate of 5 mg/hour to 16 mg/hour over a sixteen-hour period.

In one aspect, the pharmaceutically acceptable release rate-modifying polymer, or combination of pharmaceutically acceptable release rate-modifying polymers, modifies an in vitro release rate of Compound 4 from the dosage form to be an average in vitro release rate of 5 mg/hour to 16 mg/hour over a 16 hour period.

In another embodiment, the dosage forms of the present disclosure exhibit an average in vitro release rate for Compound 4 over a 16 hour period of 10 mg/hour to 16 mg/hour as determined using the dissolution test described below in Section II.J.1.c. In one aspect, the average in vitro release rate over a 16 hour period is 10 mg/hour to 14 mg/hour. In another aspect, the average in vitro release rate over a 16 hour period is 10 mg/hour to 12 mg/hour. In another aspect, the average in vitro release rate over a 16 hour period is 5 mg/hour to 10 mg/hour. In another aspect, the average in vitro release rate over a 16 hour period is 6 mg/hour to 9 mg/hour. In another aspect, the average in vitro release rate over a 16 hour period is 7 mg/hour to 9 mg/hour.

In one aspect, the pharmaceutically acceptable release rate-modifying polymer, or combination of pharmaceutically acceptable release rate-modifying polymers, modifies an in vitro release rate of Compound 4 from the dosage form to be an average in vitro release rate for the compound of 5 mg/hour to 16 mg/hour over a sixteen-hour period as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

b. Compounds 1, 2, and 3

In one embodiment, the dosage forms of the present disclosure release at least 40% by weight of each of Compounds 1, 2, and 3 within five hours as determined using the dissolution test described below in Section II.J.1.c. In one aspect, the dosage form releases at least 70% of each of Compounds 1, 2, and 3 within ten hours. In one embodiment, the dosage forms of the present disclosure release at least 40% by weight of each of Compounds 1, 2, and 3 within five hours, and at least 70% of each of Compounds 1, 2, and 3 within ten hours.

In one embodiment, the dosage forms of the present disclosure release at least 40% by weight of each of Compounds 1, 2, and 3 within five hours, and the dosage form releases at least 70% of each of Compounds 1, 2, and 3 within ten hours as determined by a dissolution test conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

c. Dissolution Test

The in vitro dissolution test used for evaluating the in vitro release properties of the dosage form as described above in Sections II.J.1.a and II.J.1.b is conducted in 900 mL of a dissolution medium comprising a 0.05 M sodium phosphate buffer pH 6.8 with 15 mM cTAB as a surfactant using a standard USP dissolution Apparatus 2 (paddle) with sinker operating at 100 RPM at 37±0.5° C.

2. In vivo Properties

While the dosage forms of the present disclosure generally will be administered pursuant to a dosage regimen that comprises administering one to four of the dosage forms once daily to the subject or administering two or three of the dosage forms once daily to the subject, each regimen is designed to provide in vivo results within a targeted therapeutic window.

a. Compound 4

In one embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
(a) the average $C_{max}$ value for Compound 4 in the population of human subjects is from 400 ng/mL to 2,000 ng/mL;
(b) the average $AUC_\infty$ value for Compound 4 in the population of human subjects is from 4,000 ng·hr/mL to 30,000 ng·hr/mL;
(c) the average $T_{max}$ value for Compound 4 in the population of human subjects is from 2.5 hours to 10 hours; and/or
(d) the average $C_{24}$ value for Compound 4 in the population of human subjects is from 20 ng/mL to 400 ng/mL.

In one aspect, the daily dosing regimen comprises administering two of the dosage forms once daily to the subject. In another aspect, the daily dosing regimen comprises administering three of the dosage forms once daily to the subject. In another aspect, the dosage forms are administered under non-fasting conditions. In another aspect, the dosage forms are administered under fasting conditions. In another aspect, the daily dosing regimen comprises administering the two or more dosage forms at substantially the same time.

In another embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
(a) the average $C_{max}$ value for Compound 4 in the population of human subjects is from 750 ng/mL to 1,500 ng/mL;
(b) the average $AUC_\infty$ value for Compound 4 in the population of human subjects is from 6,000 ng·hr/mL to 20,000 ng·hr/mL;
(c) the average $T_{max}$ value for Compound 4 in the population of human subjects is from 4 hours to 10 hours; and/or
(d) the average $C_{24}$ value for Compound 4 in the population of human subjects is from 150 ng/mL to 400 ng/mL.

b. Compound 1

In one embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
(a) the average $C_{max}$ value for Compound 1 in the population of human subjects is from 200 ng/mL to 4,000 ng/mL;
(b) the average $AUC_\infty$ value for Compound 1 in the population of human subjects is from 2,000 ng·hr/mL to 25,000 ng·hr/mL; and/or
(c) the average $T_{max}$ value for Compound 1 in the population of human subjects is from 3 hours to 8 hours.

In one aspect, the daily dosing regimen comprises administering two of the dosage forms once daily to the subject. In another aspect, the daily dosing regimen comprises administering three of the dosage forms once daily to the subject. In another aspect, the dosage forms are administered under non-fasting conditions. In another aspect, the dosage forms are administered under fasting conditions. In another aspect, the daily dosing regimen comprises administering the two or more dosage forms at substantially the same time.

In another embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
- (a) the average $C_{max}$ value for Compound 1 in the population of human subjects is from 350 ng/mL to 2,200 ng/mL;
- (b) the average $AUC_\infty$ value for Compound 1 in the population of human subjects is from 2,500 ng·hr/mL to 15,000 ng·hr/mL; and/or
- (c) the average $T_{max}$ value for Compound 1 in the population of human subjects is from 4 hours to 7 hours.

c. Compound 2

In one embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
- (a) the average $C_{max}$ value for Compound 2 in the population of human subjects is from 50 ng/mL to 200 ng/mL;
- (b) the average $AUC_\infty$ value for Compound 2 in the population of human subjects is from 800 ng·hr/mL to 2,000 ng·hr/mL; and/or
- (c) the average $T_{max}$ value for Compound 2 in the population of human subjects is from 3 hours to 7 hours.

In one aspect, the daily dosing regimen comprises administering two of the dosage forms once daily to the subject. In another aspect, the daily dosing regimen comprises administering three of the dosage forms once daily to the subject. In another aspect, the dosage forms are administered under non-fasting conditions. In another aspect, the dosage forms are administered under fasting conditions. In another aspect, the daily dosing regimen comprises administering the two or more dosage forms at substantially the same time.

In another embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
- (a) the average $C_{max}$ value for Compound 2 in the population of human subjects is from 90 ng/mL to 180 ng/mL;
- (b) the average $AUC_\infty$ value for Compound 2 in the population of human subjects is from 1,000 ng·hr/mL to 2,000 ng·hr/mL; and/or
- (c) the average $T_{max}$ value for Compound 2 in the population of human subjects is from 4 hours to 6 hours.

d. Compound 3

In one embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
- (a) the average $C_{max}$ value for Compound 3 in the population of human subjects is from 500 ng/mL to 2,500 ng/mL;
- (b) the average $AUC_\infty$ value for Compound 3 in the population of human subjects is from 3,000 ng·hr/mL to 18,000 ng·hr/mL; and/or
- (c) the average $T_{max}$ value for Compound 3 in the population of human subjects is from 3 hours to 7 hours.

In one aspect, the daily dosing regimen comprises administering two of the dosage forms once daily to the subject. In another aspect, the daily dosing regimen comprises administering three of the dosage forms once daily to the subject. In another aspect, the dosage forms are administered under non-fasting conditions. In another aspect, the dosage forms are administered under fasting conditions. In another aspect, the daily dosing regimen comprises administering the two or more dosage forms at substantially the same time.

In another embodiment, the present disclosure relates to dosage forms that, when administered once daily to a population of human subjects in accordance with a dosing regimen that provides a daily therapeutic amount of Compounds 1, 2, 3, and 4 to the subject, satisfy one or more of the following conditions:
- (a) the average $C_{max}$ value for Compound 3 in the population of human subjects is from 700 ng/mL to 2.000 ng/mL;
- (b) the average $AUC_\infty$ value for Compound 3 in the population of human subjects is from 4,000 ng·hr/mL to 12,000 ng·hr/mL; and/or
- (c) the average $T_{max}$ value for Compound 3 in the population of human subjects is from 3.5 hours to 6 hours.

K. Dosage Form Size and Type

The dosage forms of the present disclosure generally will have a weight less than 1500 mg. In one aspect, oral dosage form has a weight less than 1450 mg. In another aspect, the dosage form has a weight less than 1400 mg. In another aspect, the oral dosage form has a weight less than 1350 mg.

In one embodiment, the dosage form is a tablet. In one aspect, the dosage form is a tablet having a weight from 500 mg to 1500 mg. In another aspect, the dosage form is a tablet having a weight from 900 mg to 1500 mg. In another aspect, the tablet is coated with a polymer coating. In another aspect, the tablet hardness is from 15 kP to 45 kP. In another aspect, the tablet hardness is from 25 kP to 35 kP.

In another embodiment, the dosage form is a tablet comprising at least a first layer and a second layer. The first layer comprises the previously described first composition, and the second layer comprises the previously described second composition.

In another embodiment, the dosage form is a bilayer tablet comprising a first layer comprising the previously described first composition and a second layer comprising the previously described second composition.

In another embodiment, the dosage form is a trilayer tablet comprising a first layer comprising the first composition, a second layer comprising the second composition, and a third layer comprising an immediate release composition comprising Compound 4.

In another embodiment, the dosage form is a tablet comprising a core and at least one exterior layer, wherein the core comprises the first composition and the second composition; and the exterior layer comprises Compound 4. In one aspect, the dosage form is a tablet comprising a core and an exterior layer, wherein the core comprises the first composition and the second composition; and the exterior layer comprises an immediate release composition comprising Compound 4.

In another embodiment, the dosage form is a tablet comprising at least one outer layer comprising the active ingredients Compound 1, Compound 2, Compound 3, and Compound 4, and a second inner core tablet comprising a delayed release composition comprising Compound 4.

In another embodiment, the dosage form is a capsule comprising the first composition and the second composition.

In another embodiment, the dosage form is a sachet comprising the first composition and the second composition.

In another embodiment, the dosage form is a combination of mini-tablets. In one aspect, the dosage form comprising the combination of mini-tablets is selected from the group consisting of a compressed disintegrable tablet, an orally dispersible dosage form, a capsule, and a sachet. In another aspect, the dosage form comprising the combination of mini-tablets is a compressed disintegrable tablet. In another aspect, the dosage form comprising the combination of mini-tablets is an orally dispersible dosage form. In another aspect, the dosage form comprising the combination of mini-tablets is a capsule. In another aspect, the dosage form comprising the combination of mini-tablets is a sachet. In another aspect, the combination of the mini-tablets comprises: (a) at least one mini-tablet comprising the first composition; and (b) at least one mini-tablet comprising the second composition. In another aspect, the combination of the mini-tablets comprises: (a) at least one mini-tablet comprising Compound 1; (b) at least one mini-tablet comprising Compound 2; (c) at least one mini-tablet comprising Compound 3; and (d) at least one mini-tablet comprising Compound 4.

In another embodiment, the dosage form comprises:
(a) a first population of particles comprising Compound 1;
(b) a second population of particles comprising Compound 2;
(c) a third population of particles comprising Compound 3; and
(d) a fourth population of particles comprising Compound 4;
wherein the fourth population comprises at least two sub-populations of particles comprising Compound 4, and wherein each sub-population exhibits a different in vitro release profile for Compound 4 relative to the other sub-populations of particles comprising Compound 4.

In one aspect of the above embodiment, the fourth population comprises at least one sub-population of particles exhibiting an immediate release in vitro release profile for Compound 4; at least one sub-population of particles exhibiting a delayed-release in vitro release profile for Compound 4; at least one sub-population of particles exhibiting an extended-release in vitro release profile for Compound 4. In another aspect, the particles comprising Compound 4 further comprise a pharmaceutically acceptable stabilizing polymer, or combination of pharmaceutically acceptable stabilizing polymers. In another aspect, at least one of the sub-populations of particles comprising Compound 4 further comprises a pharmaceutically acceptable release rate-modifying polymer, or combination of pharmaceutically acceptable release rate-modifying polymers. In another aspect, the particles comprising Compound 1 are in the form of an amorphous solid dispersion. In another aspect, the particles comprising Compound 2 are in the form of an amorphous solid dispersion. In another aspect, the particles comprising Compound 3 are in the form of an amorphous solid dispersion. In another aspect, the weight ratio (free acid or free base) of Compound 1:Compound 2:Compound 3 is from 10:1:2 to 2:1:3 (Compound 1:Compound 2:Compound 3). In another aspect, the weight ratio is 6:1:4 (Compound 1:Compound 2:Compound 3).

In another embodiment, the dosage form is a sachet comprising the first population of particles, the second population of particles, the third population of particles, and the fourth population of particles.

In another embodiment, the dosage form comprises:
(a) a first population of particles comprising Compound 1, Compound 2, and Compound 3; and
(d) a second population of particles comprising Compound 4;
wherein the second population comprises at least two sub-populations of particles comprising Compound 4, and wherein each sub-population exhibits a different in vitro release profile for Compound 4 relative to the other sub-populations of particles comprising Compound 4.

In one aspect of the above embodiment, the second population comprises at least one sub-population of particles exhibiting an immediate release in vitro release profile for Compound 4; at least one sub-population of particles exhibiting a delayed-release in vitro release profile for Compound 4; at least one sub-population of particles exhibiting an extended-release in vitro release profile for Compound 4. In another aspect, the particles comprising Compound 4 further comprise a pharmaceutically acceptable stabilizing polymer, or combination of pharmaceutically acceptable stabilizing polymers. In another aspect, at least one of the sub-populations of particles comprising Compound 4 further comprises a pharmaceutically acceptable release rate-modifying polymer, or combination of pharmaceutically acceptable release rate-modifying polymers. In another aspect, the particles comprising Compound 1, Compound 2, and Compound 3 are in the form of an amorphous solid dispersion. In another aspect, the weight ratio (free acid or free base) of Compound 1:Compound 2:Compound 3 is from 3:2:24 to 60:3:5 (Compound 1:Compound 2:Compound 3). In another aspect, the weight ratio (free acid or free base) of Compound 1:Compound 2:Compound 3 is from 10:1:2 to 2:1:3 (Compound 1:Compound 2:Compound 3). In another aspect, the weight ratio is 6:1:4 (Compound 1:Compound 2:Compound 3).

In another embodiment, the dosage form is a sachet comprising the first population of particles and the second population of particles.

In another embodiment, the dosage form is an orally dispersible dosage form. The larger dosage form dimensions associated with a fixed dose combination product due to the higher-drug loading can present challenges (such as swallowing difficulties) for certain patients, especially pediatric and geriatric patients. As a result, patient compliance and use in pediatric patients may be limited. An orally dispersible dosage form (e.g., a dispersible dosage form that can disintegrate to fine dispersion within 30 seconds when in contact with water) can overcome such problems associated with dosage form size. Since the dispersible dosage form yields a fine dispersion upon immersion in water, the tablet dimensions should not impact patient compliance. In general, the dispersible dosage form can be prepared in any suitable manner including freeze-drying and direct compression methods. Excipients may include a pharmaceutically acceptable dispersing agent (such as lactose, glucose, cyclodextrin, sucrose, xylitol, mannitol, and sorbitol), a pharmaceutically acceptable disintegrant (such as croscarmellose sodium, cross-linked PVP, sodium starch glycolate, maize starch, carboxymethyl cellulose calcium, carboxymethyl cellulose sodium, and microcrystalline cellulose), and, optionally, a pharmaceutically acceptable lubricant (such as magnesium stearate, calcium stearate, aluminum stearate, stearic acid, sodium stearyl fumarate, talc, sodium benzoate, glyceryl mono fatty acid, glyceryl monostearate, glyceryl dibehenate, glyceryl palmito-stearic esters, polyethylene glycol, hydrogenated cotton seed oil, castor seed oil, and sucrose esters). The resulting blend can be incorporated into any suitable dosage form which facilitates the release of the active ingredients. Examples of such dosage forms include but are not limited to freeze-dried tablets, directly-compressed tablets, and lyophilized powders. The active ingredients can be provided, for example, in the form of individual mono-extrudates (Compounds 1, 2, and 3), co-extrudates (Compounds 1, 2, and 3), and mini-tablets.

L. Additional Representative Embodiments

In one embodiment, the solid dosage form comprises:
(a) Compound 1, wherein Compound 1 is:

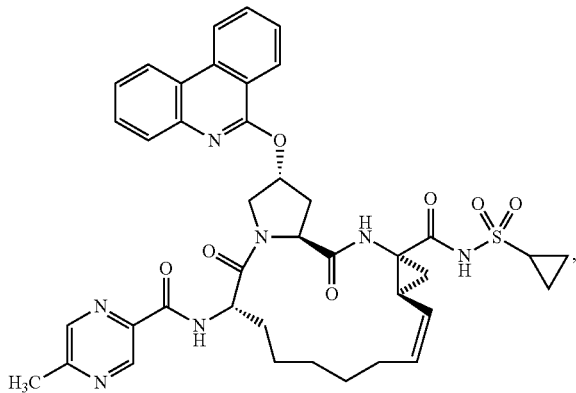 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

or a pharmaceutically acceptable salt thereof;
(b) Compound 2, wherein Compound 2 is:

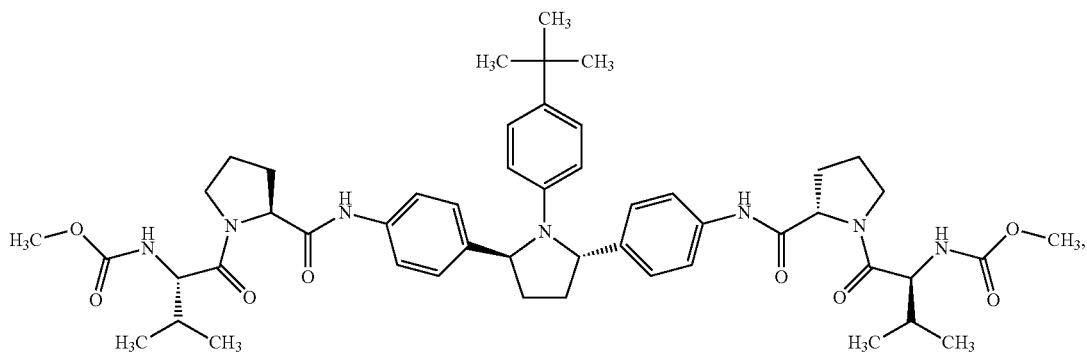 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

or a pharmaceutically acceptable salt thereof;
(c) Compound 3, wherein Compound 3 is ritonavir, or a pharmaceutically acceptable salt thereof;
(d) Compound 4, wherein Compound 4 is:

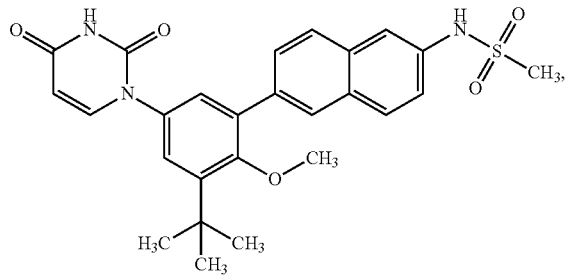 [SMILES: COc1c(-c2ccc3cc(NS(C)(=O)=O)ccc3c2)cc(-n2ccc(=O)[nH]c2=O)cc1C(C)(C)C]

or a pharmaceutically acceptable salt thereof; and
(e) a pharmaceutically acceptable stabilizing polymer, or combination of pharmaceutically acceptable stabilizing polymers.

In one aspect of the solid dosage form: (a) Compound 1 is present in an amount of 40 mg to 180 mg (free acid equivalent weight); (b) Compound 2 is present in an amount of 5 mg to 30 mg (free base equivalent weight); (c) Compound 3 is present in an amount of 25 mg to 120 mg (free base equivalent weight); (d) Compound 4 is present in an amount of 75 mg to 900 mg (free acid equivalent weight) of Compound 4; and (e) the dosage form comprises a pharmaceutically acceptable polymer, or combination of pharmaceutically acceptable polymers in an amount of 350 mg to 2500 mg. In another aspect of the solid dosage form: (a) Compound 1 is present in an amount of 40 mg to 90 mg (free acid equivalent weight); (b) Compound 2 is present in an amount of 5 mg to 15 mg (free base equivalent weight); (c) Compound 3 is present in an amount of 25 mg to 60 mg (free base equivalent weight); (d) Compound 4 is present in an amount of 75 mg to 450 mg (free acid equivalent weight) of Compound 4; and (e) the dosage form comprises a pharmaceutically acceptable polymer, or combination of pharmaceutically acceptable polymers in an amount of 400 mg to 1500 mg. In another aspect of the solid dosage form: (a) Compound 1 is present in an amount of 40 mg to 60 mg (free acid equivalent weight); (b) Compound 2 is present in an amount of 6.5 mg to 10.5 mg (free base equivalent weight); (c) Compound 3 is present in an amount of 25 mg to 40 mg (free base equivalent weight); (d) Compound 4 is present in an amount of 150 mg to 300 mg (free acid equivalent weight) of Compound 4; and (e) the dosage form comprises a pharmaceutically acceptable polymer, or combination of pharmaceutically acceptable polymers in an amount of 500 mg to 1000 mg. In another aspect of the solid dosage form: (a) Compound 1 is present in an amount of 45 mg to 55 mg (free acid equivalent weight); (b) Compound 2 is present in an amount of 7.5 mg to 9.5 mg (free base equivalent weight); (c) Compound 3 is present in an amount of 30 mg to 37 mg (free base equivalent weight); (d) Compound 4 is present in an amount of 150 mg to 300 mg (free acid equivalent weight) of Compound 4; and (e) the dosage form comprises a pharmaceutically acceptable polymer, or combination of pharmaceutically acceptable polymers in an amount of 550 mg to 750 mg.

In one aspect of the embodiment, the solid dosage form comprises a first composition comprising Compound 1, Compound 2, and Compound 3; and a second composition comprising Compound 4. In another aspect, the solid dosage form comprises a first composition comprising Compound 1, Compound 2, Compound 3, and Compound 4; and a second composition comprising Compound 4. In one aspect, the dosage form is a bilayer tablet comprising at least a first layer comprising the first composition and at least a second layer comprising the second composition. Unless otherwise specified, the terms "first layer" and "second layer" are used in a non-limiting manner and are intended to encompass bilayer tablets prepared in any tableting sequence (i.e., the first layer can prepared first followed by the second layer or the second layer can be prepared first followed by the first layer).

In one aspect, (a) the solid dosage form comprises a first composition comprising Compound 1, Compound 2, and Compound 3; and a second composition comprising Compound 4; (b) Compound 1 is present in an amount of 40 mg to 180 mg (free acid equivalent weight); (c) Compound 2 is present in an amount of 5 mg to 30 mg (free base equivalent weight); (d) Compound 3 is present in an amount of 25 mg to 120 mg (free base equivalent weight); (e) Compound 4 is present in an amount of 75 mg to 900 mg (free acid equivalent weight) of Compound 4; and (f) the second composition comprises a pharmaceutically acceptable stabilizing polymer, or combination of pharmaceutically acceptable stabilizing polymers in an amount of 20 mg to 500 mg. In another aspect, (a) the solid dosage form comprises a first composition comprising Compound 1, Compound 2, and Compound 3; and a second composition comprising Compound 4; (b) Compound 1 is present in an amount of 40 mg to 90 mg (free acid equivalent weight); (c) Compound 2 is present in an amount of 5 mg to 15 mg (free base equivalent weight); (d) Compound 3 is present in an amount of 25 mg to 60 mg (free base equivalent weight); (e) Compound 4 is present in an amount of 75 mg to 450 mg (free acid equivalent weight) of Compound 4; and (f) the second composition comprises a pharmaceutically acceptable stabilizing polymer, or combination of pharmaceutically acceptable stabilizing polymers in an amount of 25 mg to 400 mg. In another aspect, (a) the solid dosage form comprises a first composition comprising Compound 1, Compound 2, and Compound 3; and a second composition comprising Compound 4; (b) Compound 1 is present in an amount of 40 mg to 60 mg (free acid equivalent weight); (c) Compound 2 is present in an amount of 6.5 mg to 10.5 mg (free base equivalent weight); (d) Compound 3 is present in an amount of 25 mg to 40 mg (free base equivalent weight); (e) Compound 4 is present in an amount of 150 mg to 300 mg (free acid equivalent weight) of Compound 4; and (f) the second composition comprises a pharmaceutically acceptable stabilizing polymer, or combination of pharmaceutically acceptable stabilizing polymers in an amount of 30 mg to 250 mg. In another aspect, (a) the solid dosage form comprises a first composition comprising Compound 1, Compound 2, and Compound 3; and a second composition comprising Compound 4; (b) Compound 1 is present in an amount of 45 mg to 55 mg (free acid equivalent weight); (c) Compound 2 is present in an amount of 7.5 mg to 9.5 mg (free base equivalent weight); (d) Compound 3 is present in an amount of 30 mg to 37 mg (free base equivalent weight); (e) Compound 4 is present in an amount of 150 mg to 300 mg (free acid equivalent weight) of Compound 4; and (f) the second composition comprises a pharmaceutically acceptable stabilizing polymer, or combination of pharmaceutically acceptable stabilizing polymers in an amount of 50 mg to 150 mg. In each of these aspects, the dosage form can be, for example, a bilayer tablet comprising the first composition and the second composition.

In one aspect of the embodiment, the second composition further comprises the pharmaceutically acceptable stabilizing polymer, or combination of pharmaceutically acceptable stabilizing polymers, in an amount of at least 5% by weight of the second composition. In another aspect, the stabilizing polymer, or combination of stabilizing polymers are selected from the group consisting of homopolymers or copolymers of N-vinyl pyrrolidone and cellulose esters. In another aspect, the stabilizing polymer, or combination of stabilizing polymers, comprises a stabilizing polymer selected from the group consisting of copovidone, polyvinylpyrrolidone, hydroxypropyl methylcellulose, polyvinyl caprolactam-polyvinyl acetate-polyethylene glycol graft copolymer (SOLUPLUS®), and combinations thereof; wherein the hydroxypropyl methylcellulose has a viscosity less than 100 centipoise in a 2% solution of at a temperature of 20° C. In another aspect, the stabilizing polymer, or combination of stabilizing polymers, comprises copovidone.

In one aspect of the embodiment, the second composition further comprises a pharmaceutically acceptable release rate-modifying polymer, or combination of pharmaceutically acceptable release rate-modifying polymers, in an amount of at least 5% by weight of the second composition. In another aspect, the release rate-modifying polymer, or combination of release rate-modifying polymers, comprises a release rate-modifying polymer selected from the group consisting of copovidone, polyvinylpyrrolidone, and hydroxypropyl methylcellulose. In another aspect, the stabilizing polymer, or combination of stabilizing polymers, comprises copovidone; and the release rate-modifying polymer, or combination of release rate-modifying polymers comprises hydroxypropyl methylcellulose. In another aspect, the stabilizing polymer, or combination of stabilizing polymers, and the release rate-modifying polymer, or combination of release rate-modifying polymers, are the same.

In one aspect of the embodiment, the second composition further comprises the pharmaceutically acceptable stabilizing polymer, or combination of pharmaceutically acceptable stabilizing polymers, in an amount of at least 5% by weight of the second composition; and further comprises a pharmaceutically acceptable release rate-modifying polymer, or combination of pharmaceutically acceptable release rate-modifying polymers, in an amount of at least 5% by weight of the second composition. In another aspect, the stabilizing polymer, or combination of stabilizing polymers are selected from the group consisting of homopolymers or copolymers of N-vinyl pyrrolidone and cellulose esters; and the release rate-modifying polymer, or combination of release rate-modifying polymers, comprises a release rate-modifying polymer selected from the group consisting of copovidone, polyvinylpyrrolidone, and hydroxypropyl methylcellulose. In another aspect, the stabilizing polymer, or combination of stabilizing polymers, comprises a stabilizing polymer selected from the group consisting of copovidone, polyvinylpyrrolidone, hydroxypropyl methylcellulose, polyvinyl caprolactam-polyvinyl acetate-polyethylene glycol graft copolymer (SOLUPLUS®), and combinations thereof; wherein the hydroxypropyl methylcellulose has a viscosity less than 100 centipoise in a 2% solution of at a temperature of 20° C.; and the release rate-modifying polymer, or combination of release rate-modifying polymers, comprises a release rate-modifying polymer selected from the group consisting of copovidone, polyvinylpyrrolidone, and hydroxypropyl methylcellulose. In another aspect, the stabilizing polymer, or combination of stabilizing polymers, comprises copovidone; and the release rate-modifying polymer, or combination of release rate-modifying polymers comprises hydroxypropyl methylcellulose.

In one aspect of the embodiment, the first composition comprises an amorphous solid dispersion comprising one or more of Compound 1, Compound 2, and/or Compound 3. In another aspect, the amorphous solid dispersion further comprises at least one pharmaceutically acceptable hydrophilic polymer and at least one pharmaceutically acceptable surfactant.

In one aspect of the embodiment, the $D_{90}$ particle size distribution for Compound 4 is less than 150 µm. In another aspect of the solid dosage form, the $D_{90}$ particle size distribution for Compound 4 is less than 100 µm.

In one embodiment, the solid dosage form comprises:
(a) a first composition comprising:
(i) 40 mg to 90 mg (free acid equivalent weight) of Compound 1;
(ii) 5 mg to 15 mg (free base equivalent weight) of Compound 2; and
(iii) 25 mg to 60 mg (free base equivalent weight) of Compound 3; and
(b) a second composition comprising:
(i) 75 mg to 450 mg (free acid equivalent weight) of Compound 4;
(ii) a pharmaceutically acceptable stabilizing polymer, or combination of pharmaceutically acceptable stabilizing polymers, in an amount from 10% by weight to 60% by weight of the second composition; and
(iii) a pharmaceutically acceptable release rate-modifying polymer, or combination of pharmaceutically acceptable release rate-modifying polymers, in an amount from 5% by weight to 60% by weight of the second composition.

In one embodiment, the solid dosage form comprises:
(a) a first composition comprising:
(i) 40 mg to 60 mg (free acid equivalent weight) of Compound 1;
(ii) 6.5 mg to 10.5 mg (free base equivalent weight) of Compound 2; and
(iii) 25 mg to 40 mg (free base equivalent weight) of Compound 3; and
(b) a second composition comprising:
(i) 150 mg to 300 mg (free acid equivalent weight) of Compound 4;
(ii) a pharmaceutically acceptable stabilizing polymer, or combination of pharmaceutically acceptable stabilizing polymers, in an amount from 15% by weight to 55% by weight of the second composition; wherein the stabilizing polymer, or combination of stabilizing polymers, comprises a stabilizing polymer selected from the group consisting of copovidone, polyvinylpyrrolidone, hydroxypropyl methylcellulose, polyvinyl caprolactam-polyvinyl acetate-polyethylene glycol graft copolymer (SOLUPLUS®), and combinations thereof; wherein the hydroxypropyl methylcellulose has a viscosity less than 100 centipoise in a 2% solution of at a temperature of 20° C.; and
(iii) a pharmaceutically acceptable release rate-modifying polymer, or combination of pharmaceutically acceptable release rate-modifying polymers, in an amount from 10% by weight to 50% by weight of the second composition; wherein the release rate-modifying polymer, or combination of release rate-modifying polymers, comprises a release rate-modifying polymer selected from the group consisting of polyvinylpyrrolidone, hydroxypropyl methylcellulose, ethylcellulose polymers, copovidone, polyvinyl acetate, methacrylate/methacrylic free acid copolymers, polyethylene glycols, and polaxamers.

In one embodiment, the solid dosage form comprises:
(a) a first composition comprising:
(i) 45 mg to 55 mg (free acid equivalent weight) of Compound 1;
(ii) 7.5 mg to 9.5 mg (free base equivalent weight) of Compound 2; and
(iii) 30 mg to 37 mg (free base equivalent weight) of Compound 3; and
(b) a second composition comprising:
(i) 150 mg to 300 mg (free acid equivalent weight) of Compound 4;
(ii) a pharmaceutically acceptable stabilizing polymer, or combination of pharmaceutically acceptable stabilizing polymers, in an amount from 15% by weight to 55% by weight of the second composition; wherein the stabilizing polymer, or combination of stabilizing polymers, comprises a stabilizing polymer selected from the group consisting of copovidone, polyvinylpyrrolidone, hydroxypropyl methylcellulose, polyvinyl caprolactam-polyvinyl acetate-polyethylene glycol graft copolymer (SOLUPLUS®), and combinations thereof; wherein the hydroxypropyl methylcellulose has a viscosity less than 100 centipoise in a 2% solution of at a temperature of 20° C.; and
(iii) a pharmaceutically acceptable release rate-modifying polymer, or combination of pharmaceutically acceptable release rate-modifying polymers, in an amount from 10% by weight to 50% by weight of the second composition; wherein the release rate-modifying polymer, or combination of release rate-modifying polymers, comprises a release rate-modifying polymer selected from the group consisting of copovidone, polyvinylpyrrolidone, and hydroxypropyl methylcellulose.

In one embodiment, the solid dosage form comprises:
(a) a first composition comprising:
(i) 45 mg to 55 mg (free acid equivalent weight) of Compound 1;
(ii) 7.5 mg to 9.5 mg (free base equivalent weight) of Compound 2; and
(iii) 30 mg to 37 mg (free base equivalent weight) of Compound 3; and
(b) a second composition comprising:
(i) 150 mg to 300 mg (free acid equivalent weight) of Compound 4;
(ii) a pharmaceutically acceptable stabilizing polymer, or combination of pharmaceutically acceptable stabilizing polymers, in an amount from 20% by weight to 50% by weight of the second composition; wherein the stabilizing polymer, or combination of stabilizing polymers, comprises copovidone; and
(iii) a pharmaceutically acceptable release rate-modifying polymer, or combination of pharmaceutically acceptable release rate-modifying polymers, in an amount from 15% by weight to 40% by weight of the second composition; wherein the release rate-modifying polymer, or combination of release rate-modifying polymers, comprises hydroxypropyl methylcellulose.

In one embodiment, the solid dosage form comprises:
(a) a first composition comprising:
(i) 50 mg (free acid equivalent weight) of Compound 1;
(ii) 8.3 mg (free base equivalent weight) of Compound 2; and
(iii) 33.3 mg (free base equivalent weight) of Compound 3; and
(b) a second composition comprising:
(i) 150 mg to 300 mg (free acid equivalent weight) of Compound 4; wherein the D90 particle size distribution for the Compound 4 present in the dosage form is less than 100 μm;
(ii) a pharmaceutically acceptable stabilizing polymer, or combination of pharmaceutically acceptable stabilizing polymers, in an amount from 20% by weight to 50% by weight of the second composition; wherein the stabilizing polymer, or combination of stabilizing polymers, comprises copovidone; and
(iii) a pharmaceutically acceptable release rate-modifying polymer, or combination of pharmaceutically acceptable release rate-modifying polymers, in an amount from 15% by weight to 40% by weight of the second composition; wherein the release rate-modifying polymer, or combination of release rate-modifying polymers, comprises hydroxypropyl methylcellulose.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition. The second composition comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition. The second composition comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition. The second composition comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first composition. The second composition comprises 30-50% a pharmaceutically acceptable salt of Compound 4, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first composition. The second composition comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first composition. The second composition comprises 216.2 mg Compound 4 monosodium salt monohydrate, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first composition. The second composition comprises 30-50% a pharmaceutically acceptable salt of Compound 4, 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first composition. The second composition comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first composition. The second composition comprises 216.2 mg Compound 4 monosodium salt monohydrate, 30% copovidone, and 30% hypromellose, wherein all percentages are weight percentages relative to the total weight of the second composition.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first composition. The second composition comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first composition. The second composition comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first composition. The second composition comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises 30-50% a pharmaceutically acceptable salt of Compound 4, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises 216.2 mg Compound 4 monosodium salt monohydrate, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises 30-50% a pharmaceutically acceptable salt of Compound 4, 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first composition. The second composition comprises 216.2 mg Compound 4 monosodium salt monohydrate, 30% copovidone, and 30% hypromellose, wherein all percentages are weight percentages relative to the total weight of the second composition.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are each formulated in separate amorphous solid dispersions, and each solid dispersion comprises (1) the hydrophilic polymer or the combination of hydrophilic polymers and (2) the surfactant or one of the combination of surfactants. These amorphous solid dispersions can be milled and then compressed into the first composition. The second composition comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first composition. The second composition comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first composition, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first composition. The second composition comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises 30-50% a pharmaceutically acceptable salt of Compound 4, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises 216.2 mg Compound 4 monosodium salt monohydrate, 20-40% copovidone, and 20-40% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises 30-50% a pharmaceutically acceptable salt of Compound 4, 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second composition.

In yet another embodiment, the present invention features a pharmaceutical solid dosage form comprising two compositions. The first composition comprises Compound 1, Compound 2 and Compound 3, each of which is formulated in amorphous solid dispersion, and the second composition comprises a pharmaceutically acceptable salt of Compound 4 in a crystalline form. The first composition comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first composition, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first composition. The second composition comprises 216.2 mg Compound 4 monosodium salt monohydrate, 30% copovidone, and 30% hypromellose, wherein all percentages are weight percentages relative to the total weight of the second composition.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 30% copovidone, and 30% hypromellose, wherein all percentages are weight percentages relative to the total weight of the second layer.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer.

The second layer comprises 216.2 mg Compound 4 monosodium salt monohydrate, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 216.2 mg Compound 4 monosodium salt monohydrate, 30% copovidone, and 30% hypromellose, wherein all percentages are weight percentages relative to the total weight of the second layer.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or the combination of hydrophilic polymers and (2) the surfactant or one of the combination of surfactants. These amorphous solid dispersions can be milled and then compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 20-40% copovidone, and 20-40% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 30% copovidone, and 30% hypromellose, wherein all percentages are weight percentages relative to the total weight of the second layer.

In each and every embodiment, aspect and example described herein, when the pharmaceutical solid dosage form is dissolved in 900 mL of a dissolution medium using a standard USP dissolution Apparatus 2 (paddle) operating at 100 RPM at 37° C., the solid dosage form can, for example, have the following release profile: 50-60% Compound 1 in the solid dosage form is released within 1 hour, 50-60% Compound 2 in the solid dosage form is released within 1 hour, 50-60% Compound 3 in the solid dosage form is released within 1 hour, and 0.5-2% Compound 4 in the solid dosage form is released within 1 hour. The dissolution medium is 0.05 M sodium phosphate buffer (pH 6.8) with 15 mM cTAB as a surfactant.

In each and every embodiment, aspect and example described herein, when the pharmaceutical solid dosage form is dissolved in 900 mL of a dissolution medium using a standard USP dissolution Apparatus 2 (paddle) operating at 100 RPM at 37° C., the solid dosage form can, for example, have the following release profile: 95-100% Compound 1 in the solid dosage form is released within 4 hours, 95-100% Compound 2 in the solid dosage form is released within 4 hours, 95-100% Compound 3 in the solid dosage form is released within 4 hours, and 10-15% Compound 4 in the solid dosage form is released within 4 hours. The dissolution medium is 0.05 M sodium phosphate buffer (pH 6.8) with 15 mM cTAB as a surfactant.

In each and every embodiment, aspect and example described herein, when the pharmaceutical solid dosage form is dissolved in 900 mL of a dissolution medium using a standard USP dissolution Apparatus 2 (paddle) operating at 100 RPM at 37° C., the solid dosage form can, for example, have the following release profile: 95-100% Compound 1 in the solid dosage form is released within 6 hours, 95-100% Compound 2 in the solid dosage form is released within 6 hours, 95-100% Compound 3 in the solid dosage form is released within 6 hours, and 15-20% Compound 4 in the solid dosage form is released within 6 hours. The dissolution medium is 0.05 M sodium phosphate buffer (pH 6.8) with 15 mM cTAB as a surfactant.

In each and every embodiment, aspect and example described herein, when the pharmaceutical solid dosage form is dissolved in 900 mL of a dissolution medium using a standard USP dissolution Apparatus 2 (paddle) operating at 100 RPM at 37° C., the solid dosage form can, for example, have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, and 40-60% Compound 4 in the solid dosage form is released within 16 hours. The dissolution medium is 0.05 M sodium phosphate buffer (pH 6.8) with 15 mM cTAB as a surfactant.

In each and every embodiment, aspect and example described herein, when the pharmaceutical solid dosage form is dissolved in 900 mL of a dissolution medium using a standard USP dissolution Apparatus 2 (paddle) operating at 100 RPM at 37° C., the solid dosage form can, for example, have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

Accordingly, in another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 216.2 mg Compound 4 monosodium salt monohydrate, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 216.2 mg Compound 4 monosodium salt monohydrate, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or the combination of hydrophilic polymers and (2) the surfactant or one of the combination of surfactants. These amorphous solid dispersions can be milled and then compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 20-40% copovidone, and 20-40% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 30% copovidone, and 30% hypromellose, wherein all percentages are weight percentages relative to the total weight of the second layer. When the pharmaceutical solid dosage form is dissolved in 900 mL of a dissolution medium using a standard USP dissolution Apparatus 2 (paddle) operating at 100 RPM at 37° C., the solid dosage form can have the following release profile: 100% Compound 1 in the solid dosage form is released within 8 hours, 100% Compound 2 in the solid dosage form is released within 8 hours, 100% Compound 3 in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours. The dissolution medium is 0.05 M sodium phosphate buffer (pH 6.8) with 15 mM cTAB as a surfactant.

In each and every embodiment, aspect and example described in this disclosure, when a single dose consisting of the same three solid dosage forms is administered to humans under non-fasting conditions, it can, for example, produce the following pharmacokinetics profile: the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

Accordingly, in another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer. The second layer comprises 30-50% a pharmaceutically acceptable salt of Compound 4, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, sorbitan monolaurate and lauroglycol, wherein all percentages are weight percentages relative to the total weight of the first layer. The second layer comprises 216.2 mg Compound 4 monosodium salt monohydrate, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are formulated in the same amorphous solid dispersion which comprises (1) the hydrophilic polymer or the combination of hydrophilic polymers and (2) the surfactant or the combination of surfactants. The amorphous solid dispersion can be milled and compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 216.2 mg Compound 4 monosodium salt monohydrate, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 30-50% a pharmaceutically acceptable salt of Compound 4, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are formulated in the same amorphous solid dispersion which comprises copovidone, vitamin E TPGS, lauroglycol and sorbitan monolaurate. The amorphous solid dispersion can be milled and compressed into the first layer. The second layer comprises 216.2 mg Compound 4 monosodium salt monohydrate, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or the combination of hydrophilic polymers and (2) the surfactant or one of the combination of surfactants. These amorphous solid dispersions can be milled and then compressed into the first layer. The second layer comprises 30-50% a pharmaceutically acceptable salt of Compound 4, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% a pharmaceutically acceptable hydrophilic polymer or a combination of pharmaceutically acceptable hydrophilic polymers, and 5-10% a pharmaceutically acceptable surfactant or a combination of pharmaceutically acceptable surfactants, wherein all percentages are weight percentages relative to the total weight of the first layer, and wherein Compound 1, Compound 2 and Compound 3 are each formulated in separate amorphous solid dispersions, and each solid dispersion comprises (1) the hydrophilic polymer or one of the combination of hydrophilic polymers and (2) the surfactant or one of the combination of surfactants. These amorphous solid dispersions can be milled and then compressed into the first layer. The second layer comprises 216.2 mg Compound 4 monosodium salt monohydrate, 20-40% a pharmaceutically acceptable stabilizing polymer or a combination of pharmaceutically acceptable stabilizing polymers, and 20-40% a pharmaceutically acceptable release rate-modifying polymer or a combination of pharmaceutically acceptable release rate-modifying polymers, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, sorbitan monolaurate and lauroglycol, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 20-40% copovidone, and 20-40% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 5-10% Compound 1, 1-5% Compound 2, 2-8% Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 30-50% a pharmaceutically acceptable salt of Compound 4, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises a pharmaceutically acceptable salt of Compound 4 in an amount equivalent to 200 mg Compound 4 (e.g., 216.2 mg Compound 4 monosodium salt monohydrate), 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In yet another embodiment, the present invention features a pharmaceutical solid dosage form which is a tablet comprising two layers. The first layer comprises Compound 1, Compound 2 and Compound 3, each of which is formulated in amorphous solid dispersion, and the second layer comprises a pharmaceutically acceptable salt of Compound 4 in a crystalline form. The first layer comprises 50 mg Compound 1, 8.33 mg Compound 2, 33.33 mg Compound 3, 70-85% copovidone, and 5-10% a combination of vitamin E TPGS, lauroglycol and sorbitan monolaurate, wherein all percentages are weight percentages relative to the total weight of the first layer, and wherein Compound 1, Compound 2 and Compound 3 are each formulated in separate amorphous solid dispersions. The solid dispersion comprising Compound 1 can comprise copovidone, vitamin E TPGS and lauroglycol; the solid dispersion comprising Compound 2 can comprise copovidone and vitamin E TPGS; and the solid dispersion comprising Compound 3 can comprise copovidone and sorbitan monolaurate. These amorphous solid dispersions can be milled and then compressed into the first layer. The second layer comprises 216.2 mg Compound 4 monosodium salt monohydrate, 30% copovidone, and 30% hypromellose, wherein all percentages are weight percentages relative to the total weight of the second layer. When a single dose consisting of three solid dosage forms of this embodiment is administered to humans under non-fasting conditions, the AUC∞ for Compound 1 is 4000-5000 ng·h/mL, the AUC∞ for Compound 2 is 1500-2500 ng·h/mL, the AUC∞ for Compound 3 is 7000-9000 ng·h/mL, and the AUC∞ for Compound 4 is 10000-20000 ng·h/mL.

In each and every embodiment, aspect and example described in this application, the size of the pharmaceutical solid dosage form can be, for example, 1000-1600 mg.

In each and every embodiment, aspect and example described in this disclosure, the size of the pharmaceutical solid dosage form can be, for example, 1200-1400 mg.

In each and every embodiment, aspect and example described in this disclosure, the size of the pharmaceutical solid dosage form can be, for example, 1300-1400 mg.

III. METHODS OF TREATMENT

In one embodiment, the disclosed solid dosage forms can be used for treating a disease that can be treated by inhibiting HCV RNA polymerase.

In another embodiment, the disclosed solid dosage forms can be used for treating HCV infection in a subject in need of such treatment. In one aspect, the subject is suffering from both HCV infection and human immunodeficiency virus (HIV) infection.

In another embodiment, the disclosed solid dosage forms can be used for treating liver disease in a subject in need of such treatment. In one aspect, the liver disease is end-stage liver disease. In another aspect, the liver disease is cirrhosis. In another aspect, the liver disease is hepatocellular carcinoma. In another aspect, the treatment delays the progression of the liver disease.

These methods of treatment comprise administering to the subject one or more of the disclosed solid dosage forms, and, optionally, one or more additional therapeutic agents. In one aspect, the method comprises administering at least one of the dosage forms once daily to the subject. In one aspect, the at least one dosage forms administered once daily to the subject is a tablet. In another aspect, the method comprises administering two of the dosage forms once daily to the subject. In one aspect, the at least one dosage forms administered once daily to the subject are tablets. In another aspect, the method comprises administering three of the dosage forms once daily to the subject. In one aspect, the at least three dosage forms administered once daily to the subject are tablets. In another aspect, the dosage forms are administered under non-fasting conditions. In another aspect, the dosage forms are administered under fasting conditions. In another aspect, the method comprises administering the two or more dosage forms once daily at substantially the same time. In another aspect, the subject in need of treatment is suffering from, or is susceptible to, HCV infection.

IV. COMBINATION THERAPY

The methods of treatment of the present disclosure also comprise combination therapy in which the disclosed solid dosage forms are co-administered with a second (or even a third, fourth, etc.) composition, such as, for example, a composition containing another therapeutic agent used to treat HCV infection (e.g., interferon or interferon/ribavirin combination, or an HCV inhibitor such as, for example, an HCV polymerase inhibitor or an HCV protease inhibitor or an NS5a inhibitor). The disclosed solid dosage forms also can be co-administered with therapeutic agents other than therapeutic agents used to treat HCV infection (e.g., anti-HIV agents). In these co-administration embodiments, the disclosed solid dosage forms and the second, etc. composition(s) may be administered in a substantially simultaneous manner (e.g., or within about five minutes of each other), in a sequential manner, or both. It is contemplated that such combination therapies may include administering the additional therapeutic agent(s) multiple times between the administration of the disclosed solid dosage forms. The time period between the administration of each additional therapeutic agent(s) may range from a few seconds (or less) to several hours or days, and will depend on, for example, the properties of the additional therapeutic agent as formulated (e.g., potency, solubility, bioavailability, half-life, and kinetic profile), as well as the condition of the patient.

V. KITS

The present disclosure also relates to kits comprising one or more solid dosage forms of the present disclosure. The kit optionally can comprise one or more additional therapeutic agents and/or instructions, for example, instructions for using the kit. In one embodiment, the kit comprises a plurality of separate packages with each package containing a daily dose of the solid dosage forms (e.g., a package containing two or three of the solid dosage forms).

VI. METHODS OF PREPARATION

The present disclosure also relates to methods for preparing the solid dosage forms described in this specification, including those methods described in the Examples below.

In one embodiment, the disclosure relates to methods for preparing a single amorphous solid dispersion comprising Compounds 1, 2 and 3 that can be used to in the preparation of the dosage form. The amorphous solid dispersion can be prepared by a variety of techniques such as, without limitation, melt-extrusion, spray-drying, co-precipitation, freeze drying, or other solvent evaporation techniques, with melt-extrusion and spray-drying being preferred.

In another embodiment, the method generally comprises, for example: (1) preparing a melt comprising Compound 1, Compound 2, Compound 3, a pharmaceutically acceptable hydrophilic polymer, and a pharmaceutically acceptable surfactant; and (2) solidifying the melt. The solidified melt can comprise any amorphous solid dispersion described or contemplated herein. The method can further comprise milling the solidified melt, followed by compressing the milled product with one or more other excipients or ingredients to form a tablet core. These other excipients or ingredients can include, for example, coloring agents, flavoring agents, lubricants or preservatives. In one aspect, the melt is formed at a temperature from 150° C. to 180° C. In another aspect, the melt is formed at a temperature from 150° C. to 170° C. In another aspect, the melt is formed at a temperature from 150° C. to 160° C. In another aspect, the melt is formed at a temperature from 160° C. to 170° C.

The melt-extrusion process typically comprises the steps of preparing a melt which includes the active ingredients (i.e., Compound 1, Compound 2, and Compound 3), the hydrophilic polymer(s) and optionally the surfactant(s), and then cooling the melt until it solidifies. "Melting" means a transition into a liquid or rubbery state in which it is possible for one component to get embedded, such as homogeneously embedded, in the other component or components. In many cases, the polymer component(s) will melt and the other components including the active ingredients and surfactant(s) will dissolve in the melt thereby forming a solution. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredients efficiently. In addition, it may be convenient first to melt the polymer(s) and then to mix in and homogenize the active ingredients. In one example, all materials except surfactant(s) are blended and fed into an extruder, while the surfactant(s) is molten externally and pumped in during extrusion.

In the melt-extrusion process, the active ingredients can be employed in their solid forms, such as their respective crystalline forms. The active ingredients can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose such as extruders or kneaders. Suitable extruders may include single screw extruders, intermeshing screw extruders or multi-screw extruders, such as twin screw extruders, which can be co-rotating or counter-rotating and, optionally, be equipped with kneading disks. It will be appreciated that the working temperatures will be determined by the kind of extruder or the kind of configuration within the extruder that is used. Friction and shearing of the material in the extruder may provide a substantial amount of energy to the mixture and aid in the formation of a homogeneous melt of the components. However, part of the energy needed to melt, mix and dissolve the components in the extruder can be provided by heating elements.

The consistency of the melt can range from thin to pasty to viscous. Shaping of the extrudate can be conveniently carried out by a calender with two counter-rotating rollers with mutually matching depressions on their surface. The extrudate can be cooled and allowed to solidify. The extrudate can also be cut into pieces, either before solidification (hot-cut) or after solidification (cold-cut).

The solidified extrusion product can be further milled, ground or otherwise reduced to granules. The solidified extrudate, as well as each granule produced, comprises a solid dispersion, such as a solid solution, of the active ingredients in a matrix comprised of the hydrophilic polymer(s) and the pharmaceutically acceptable surfactant(s). The extrusion product can also be blended with other active ingredient(s) and/or additive(s) before being milled or ground into granules. The granules can be further processed into suitable solid oral dosage forms.

In one example, copovidone and one or more surfactants (e.g., vitamin E TPGS in combination with propylene glycol monolaurate) are mixed and granulated, followed by the addition of aerosil and Compound 1, Compound 2, and Compound 3. The mixture is milled, and then subjected to extrusion. The extrudate thus produced can be milled and sieved for further processing to make capsules or tablets. Surfactant(s) employed in this example can be added, for example, through liquid dosing during extrusion.

Alternatively, the amorphous solid dispersion can be prepared using the approach of solvent evaporation, via spray-drying, which provides the advantage of allowing for processing at lower temperatures, if needed, and also allows for other modifications to the process in order to further improve powder properties. The spray-dried powder can then be formulated further, if needed, and final drug product is flexible with regards to whether capsule, tablet or any other solid dosage form is desired.

Exemplary spray-drying processes and spray-drying equipment are described in K. Masters, SPRAY DRYING HANDBOOK (Halstead Press, New York, 4$^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus to be essentially solid and to form a fine powder to avoid sticking to the apparatus wall. The spray-dried product can be collected by removing the material manually, pneumatically, mechanically or by other suitable means. The actual length of time to achieve the desired level of dryness depends on the size of the droplets, the formulation, and spray dryer operation. Following the solidification, the solid powder may stay in the spray drying chamber for additional time (e.g., 5 seconds to 60 seconds) to further evaporate solvent from the solid powder. The final solvent content in the solid dispersion as it exits the dryer is generally at a sufficiently low level so as to improve the stability of the final product. For instance, the residual solvent content of the spray-dried powder can be less than 2% by weight. The residual solvent content may be within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other suitable processes.

Like the solid extrudate described above, the spray dried product contains a solid dispersion, such as a solid solution, of the active ingredients in a matrix comprised of the hydrophilic polymer(s) and the pharmaceutically acceptable surfactant(s).

Before feeding into a spray dryer, the active ingredients, the hydrophilic polymer(s), as well as other excipients such as the pharmaceutically acceptable surfactant(s), can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground into granules or powders before compression. Compression can be performed in a tablet press, such as in a steel die between two moving punches.

At least one additive selected from flow regulators, binders, lubricants, fillers, disintegrants, or plasticizers may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates (such as silicium dioxide), magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives or ingredients may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack; or other active pharmaceutical ingredients.

Accordingly, one representative embodiment relates to a method of making the dosage forms described in this specification, wherein the method comprises:
(a) preparing a melt comprising Compound 1, Compound 2, Compound 3, a hydrophilic polymer, and a surfactant;
(b) solidifying the melt to form an amorphous solid dispersion;
(c) preparing a first composition comprising the amorphous solid dispersion;
(d) preparing a second composition comprising Compound 4; and
(e) formulating the first composition and the second composition to provide the dosage form.

In one aspect, the preparing the first composition step further comprises: (a) milling the solidified melt to provide particles of the amorphous solid dispersion; and (b) optionally combining the particles of the amorphous solid dispersion with one or more excipients to provide the first composition. In another aspect, the melt is prepared at a temperature of 150° C. to 170° C. In another aspect, the melt is prepared at a temperature of 160° C. to 170° C.

Another representative embodiment relates to a method of making the dosage forms described in this specification, wherein the method comprises:
(a) preparing the first composition comprising Compound 1, Compound 2, and Compound 3;
(b) granulating (i) a mixture comprising at least a portion of the Compound 4 with at least a portion of the stabilizing polymer, or combination of stabilizing polymers, to provide granules comprising Compound 4; (ii) a mixture comprising at least a portion of the Compound 4 with at least a portion of the release rate-modifying polymer, or combination of release rate-modifying polymers, to provide granules comprising Compound 4; or (iii) a mixture comprising at least a portion of the Compound 4 with at least a portion of the stabilizing polymer, or combination of stabilizing polymers, and at least a portion of the release rate-modifying polymer, or combination of stabilizing polymers, to provide granules comprising Compound 4;
(c) preparing the second composition using the granules as a source of at least a portion of the Compound 4 present in the second composition; and
(d) formulating the first composition and the second composition to provide the dosage form.

VII. PRODUCT-BY-PROCESS

The present disclosure also relates to solid dosage forms prepared in accordance with any of the methods described in this specification, including the methods described in the Examples below.

In one embodiment, the dosage form is prepared by a process comprising:
granulating (i) a mixture comprising at least a portion of the Compound 4 with at least a portion of the stabilizing polymer, or combination of stabilizing polymers, to provide granules comprising Compound 4; (ii) a mixture comprising at least a portion of the Compound 4 with at least a portion of the release rate-modifying polymer, or combination of release rate-modifying polymers, to provide granules comprising Compound 4; or (iii) a mixture comprising at least a portion of the Compound 4 with at least a portion of the stabilizing polymer, or combination of stabilizing polymers, and at least a portion of the release rate-modifying polymer, or combination of stabilizing polymers, to provide granules comprising Compound 4; and
preparing the second composition using the granules as a source of at least a portion of the Compound 4 present in the second composition.

VIII. EXAMPLES

Unless otherwise stated, in the formulations described in the Examples below: (i) the Compound 1 free acid was used; (ii) the Compound 2 free base was used; (iii) the Compound 3 free base was used; and the Compound 4 monosodium salt monohydrate was used.

Example 1

Bilayer Tablet (Formulation C5-12)

Bilayer tablets (Formulation C5-12) comprising a first bilayer blend containing Compound 1, Compound 2, and Compound 3, and a second bilayer containing Compound 4 were prepared. The specific composition of the resulting Formulation C5-12 is set forth in Table 1-A below.

TABLE 1-A

Bilayer Tablet (Formulation C5-12)

| COMPONENT | FUNCTION | FORMULATION C5-12 (mg/TABLET) |
|---|---|---|
| BILAYER 1 | | |
| Compound 1 Mono-Extrudate | | |
| Compound 1 | Drug Substance | 50.00 |
| Copovidone | Polymer Carrier | 256.67 |
| Vitamin E, TPGS | Surfactant/Plasticizer | 16.67 |

TABLE 1-A-continued

Bilayer Tablet (Formulation C5-12)

| COMPONENT | FUNCTION | FORMULATION C5-12 (mg/TABLET) |
|---|---|---|
| Lauroglycol FCC | Surfactant/Plasticizer | 6.67 |
| Colloidal Silicon Dioxide | Glidant | 3.33 |
| Compound 2 Mono-Extrudate | | |
| Compound 2 | Drug Substance | 8.33 |
| Copovidone | Polymer Carrier | 144.9 |
| Vitamin E, TPGS | Surfactant/Plasticizer | 11.67 |
| Colloidal Silicon Dioxide | Glidant | 1.67 |
| Compound 3 Mono-Extrudate | | |
| Compound 3 | Drug Substance | 33.33 |
| Copovidone | Polymer Carrier | 164.44 |
| Sorbitan Monolaurate | Surfactant/Plasticizer | 22.22 |
| Colloidal Silicon Dioxide | Glidant | 2.22 |
| Colloidal Silicon Dioxide | Glidant | 1.8 |
| Total Bilayer 1 Weight | | 723.9 |
| BILAYER 2 (200 mg Compound 4) | | |
| Compound 4 granules: Compound 4 (55.7%) | Drug Substance (Compound 4) | 216.2[1] |
| Copovidone Type K 28 (44.3%) | Polymer (Copovidone) | 172.0 |
| Hypromellose 2208, USP/EP, 20,700 mPa · S (Premium CR) | Polymer | 173.2 |
| Colloidal Silicon Dioxide | Glidant | 1.44 |
| Magnesium Stearate, NF/EP, Impalpable Powder (Veget. Grade) | Lubricant | 14.46 |
| Total Bilayer 2 Weight | | 577.3 |
| TABLET WEIGHT(mg) | | 1301.2 |

[1]Equivalent to 200.0 mg of Compound 4 (free acid).

Each of the Compound 1, Compound 2, and Compound 3 components was prepared as a separate amorphous solid dispersion comprising the active ingredient using hot melt extrusion technology and milled prior to blending with the other two amorphous solid dispersions. The Compound 1 mono-extrudate and the Compound 3 mono-extrudate were prepared as described in Example 4 of published U.S. application US2011/0312973. The Compound 2 mono-extrudate was prepared as described in Example 1 of published international application WO2011/156578.

A. Compound 1 Mono-Extrudate

As stated above, the Compound 1 mono-extrudate was prepared using hot melt extrusion technology in which Compound 1 was converted from crystalline to amorphous form and uniformly distributed in a polymer-surfactant matrix. The Compound 1 mono-extrudate prepared contained: (i) copovidone as a carrier polymer, (ii) colloidal silicon dioxide as a glidant to aid in powder flow into the extruder, and (iii) vitamin E tocopheryl polyethylene glycol succinate (vitamin E TPGS) and propylene glycol monolaurate, type I (Lauroglycol™ FCC) as surfactants/plasticizers. The specific composition of the Compound 1 mono-extrudate prepared is set forth below in Table 1-B.

TABLE 1-B

Compound 1 Mono-Extrudate

| COMPONENT | FUNCTION | WEIGHT PERCENT |
|---|---|---|
| Compound 1 | Drug Substance | 15[1] |
| Copovidone | Polymer Carrier | 77 |
| Vitamin E, TPGS | Surfactant/Plasticizer | 5 |
| Lauroglycol FCC | Surfactant/Plasticizer | 2 |
| Colloidal Silicon Dioxide | Glidant | 1 |

[1]Weight/weight % based on free acid equivalent amount of Compound 1.

B. Compound 2 Mono-Extrudate

As stated above, the Compound 2 mono-extrudate was prepared using hot melt extrusion technology in which Compound 2 was converted from crystalline to amorphous form and uniformly distributed in a polymer-surfactant matrix. The Compound 2 mono-extrudate contains: (i) copovidone as a carrier polymer, (ii) colloidal silicon dioxide as a glidant to aid in powder flow into the extruder, and (iii) vitamin E tocopheryl polyethylene glycol succinate (vitamin E TPGS) as a surfactant/plasticizer. The specific composition of the Compound 2 mono-extrudate prepared is set forth below in Table 1-C.

TABLE 1-C

Compound 2 Mono-Extrudate

| COMPONENT | FUNCTION | WEIGHT PERCENT |
|---|---|---|
| Compound 2 | Drug Substance | 5[1] |
| Copovidone | Polymer Carrier | 87 |
| Vitamin E, TPGS | Surfactant/Plasticizer | 7 |
| Colloidal Silicon Dioxide | Glidant | 1 |

[1]Weight/weight % based on free base equivalent amount of Compound 2.

C. Compound 3 Mono-Extrudate

As stated above, the Compound 3 mono-extrudate was prepared using hot melt extrusion technology in which Compound 3 was converted from crystalline to amorphous form and uniformly distributed in a polymer-surfactant matrix. The Compound 3 mono-extrudate prepared contained: (i) copovidone as a carrier polymer, (ii) colloidal silicon dioxide as a glidant to aid in powder flow into the extruder, and (iii) sorbitan monolaurate as a surfactant/plasticizer. The specific composition of the Compound 3 mono-extrudate prepared is set forth below in Table 1-D.

TABLE 1-D

Compound 3 Mono-Extrudate

| COMPONENT | FUNCTION | WEIGHT PERCENT |
|---|---|---|
| Compound 3 | Drug Substance | 15[1] |
| Copovidone | Polymer Carrier | 74 |
| Sorbitan Monolaurate | Surfactant/Plasticizer | 10 |
| Colloidal Silicon Dioxide | Glidant | 1 |

[1]Weight/weight % based on free acid equivalent amount of Compound 3.

D. First Bilayer Blend

A first bilayer blend comprising the Compound 1 mono-extrudate, the Compound 2 mono-extrudate, and the Compound 3 mono-extrudate was prepared. The mono-extrudates were each milled, combined in a 46: 23:31 ratio (Compound 1:Compound 2:Compound 3) based on the weight percent of active ingredient, and blended with additional colloidal silicon dioxide to form the first bilayer blend having the composition reported in Table 1-E below.

TABLE 1-E

| First Bilayer Blend (Formulation C5-12) | |
|---|---|
| COMPONENT | AMOUNT (mg/TABLET) |
| Compound 1 Mono-Extrudate | 333.3 |
| Compound 2 Mono-Extrudate | 166.7 |
| Compound 3 Mono-Extrudate | 222.2 |
| Colloidal Silicon Dioxide, NF/EP | 1.8 |
| TOTAL | 724.0 |

E. Compound 4 Granules

Compound 4 was granulated with copovidone in a fluid bed granulation process. Compound 4 was added together with copovidone to the fluid bed granulator. The powders were fluidized with heated air at approximately 35° C. to 55° C. and water was subsequently sprayed from the top onto the fluidized powder bed. The water was sprayed at a rate sufficient to increase the moisture content of the granulation to a target of approximately 8% to 14% moisture. The water spray rate was then slightly reduced to maintain the granulation at the target moisture content for a hold period of approximately 15 minutes or longer. The spraying was subsequently stopped. The heated air temperature was increased and the granulation was dried until the moisture content was reduced to no greater than about 2 w/w %. The $D_{50}$ particle size distribution of the granules was between 80 and 130 microns. This method of granulation improved the bulk handling properties of the resulting combination of Compound 4 and copovidone while maintaining the intrinsic small particle size of Compound 4. The resulting Compound 4 granules had the composition reported in Table 1-F below.

TABLE 1-F

| Compound 4 Granules (Formulation C5-12) | |
|---|---|
| COMPONENT | WEIGHT PERCENT |
| Compound 4 (monosodium salt monohydrate) | 55.7 |
| Copovidone Type K 28 | 44.3 |
| Purified Water | — |
| TOTAL | 100 |

The Compound 4 granules prepared as described above were then blended with HPMC Hypromellose 2208, colloidal silicon dioxide, and magnesium stearate to form the second bilayer blend used in the preparation of Formulation C5-12. The specific composition of the second bilayer blend is set forth in Table 1-G below.

TABLE 1-G

| Second Bilayer Blend (Formulation C5-12) BILAYER 2 (200 mg Compound 4) | | |
|---|---|---|
| Compound 4 granules: Compound 4 (55.7%) Copovidone Type K 28 (44.3%) | Compound 4 Copovidone) | 216.2[1] 172.0 |
| Hypromellose 2208, USP/EP, 20,700 mPa · S (Premium CR) | | 173.2 |
| Colloidal Silicon Dioxide | | 1.44 |
| Magnesium Stearate, NF/EP, Impalpable Powder (Veget. Grade) | | 14.46 |
| Total | | 577.3 |

[1]Equivalent to 200.0 mg of Compound 4 (free acid).

F. Tablet Preparation (Formulation C5-12)

Formulation C5-12 was prepared by loading a unit dose of the second bilayer blend into the tablet die (oval, concave tooling, 10 mm width×18.8 mm length) on an automated bilayer tablet press, compressing the second bilayer blend with a compression force of approximately 4 kN, loading a unit dose of the first bilayer blend into the same tablet die on top of the previously compressed second bilayer blend, and compressing the first bilayer blend with a compression force of approximately 25 kN.

Example 2

Sink Conditions Dissolution Testing

The release profiles of Formulation C5-12 of Example 1 were evaluated in a Sink Conditions dissolution study. The study was conducted in 900 mL of dissolution medium using a standard USP dissolution Apparatus 2 (paddle) operating at 100 RPM at 37±0.5° C. The dissolution medium was a 0.05 M sodium phosphate buffer pH 6.8 with 15 mM cTAB as a surfactant.

Results for the Compound 1 component of Formulation C5-12 of Example 1 are reported in Table 2-A below.

Results for the Compound 2 component of Formulation C5-12 of Example 1 are reported in Table 2-B below.

Results for the Compound 3 component of Formulation C5-12 of Example 1 are reported in Table 2-C below.

Results for the Compound 4 component of Formulation C5-12 of Example 1 are reported in Table 2-D (% Released) and Table 2-E (mg Released) below.

TABLE 2-A

| Sink Conditions Dissolution Release Profile (Compound 1) | | | | | | |
|---|---|---|---|---|---|---|
| | Time (Hours) | | | | | |
| | 1 | 4 | 6 | 8 | 12 | 16 |
| % Released | 54 | 98 | 99 | 102 | 102 | 101 |
| Std. Dev. (N = 6) | 3.2 | 2.1 | 2.3 | 2.4 | 2.2 | 2.2 |

TABLE 2-B

| Sink Conditions Dissolution Release Profile (Compound 2) | | | | | | |
|---|---|---|---|---|---|---|
| | Time (Hours) | | | | | |
| | 1 | 4 | 6 | 8 | 12 | 16 |
| % Released | 55 | 98 | 99 | 103 | 102 | 102 |
| Std. Dev. (N = 6) | 2.8 | 1.8 | 1.9 | 2.1 | 2.2 | 2.1 |

TABLE 2-C

| Sink Conditions Dissolution Release Profile (Compound 3) | | | | | | |
|---|---|---|---|---|---|---|
| | Time (Hours) | | | | | |
| | 1 | 4 | 6 | 8 | 12 | 16 |
| % Released | 58 | 99 | 100 | 103 | 102 | 100 |
| Std. Dev. (N = 6) | 2.9 | 2.1 | 1.9 | 2.2 | 2.2 | 2.0 |

TABLE 2-D

Sink Conditions Dissolution Release Profile
(Compound 4: Percent Released)

| | Time (Hours) | | | | | | | |
|---|---|---|---|---|---|---|---|---|
| | 1 | 4 | 6 | 8 | 12 | 16 | 24 | 30 |
| % Released | 1 | 11 | 18 | 25 | 39 | 51 | 70 | 81 |
| Std. Dev. (N = 6) | 0.1 | 0.7 | 1.4 | 1.9 | 2.6 | 3.1 | 3.8 | 3.9 |

TABLE 2-E

Sink Conditions Dissolution Release Profile
(Compound 4: mg Released)

| | Time (Hours) | | | | | | | |
|---|---|---|---|---|---|---|---|---|
| | 1 | 4 | 6 | 8 | 12 | 16 | 24 | 30 |
| mg Released | 2.3 | 25.7 | 42.0 | 58.3 | 91.0 | 119.0 | 163.3 | 189.0 |
| Std. Dev. (N = 6) | 0.2 | 1.6 | 3.3 | 4.4 | 6.1 | 7.2 | 8.9 | 9.1 |

Example 3

FeSSIF Dissolution Testing

Release profiles are obtained for Formulation C5-12 of Example 1 using a Fed-State Simulated Intestinal Fluid ("FeSSIF") dissolution protocol under non-sink conditions. The study is conducted in 450 mL of dissolution medium using a standard USP dissolution Apparatus 2 (paddle) operating at 75 RPM at 37±0.5° C. The dissolution medium is a 0.04 M sodium phosphate buffer pH 6.8 with 11.2 g/L Phares SIF Original Powder (biorelevant.com, Croydon, Surrey, UK) to simulate FeSSIF conditions. Although the Sink Conditions dissolution method discussed in Example 2 provides results that are acceptable for general comparisons of release profiles, that method does not account for the conversion of a Compound 4 salt to the insoluble Compound 4 free acid in vivo and the resulting reduction in Compound 4 bioavailability that has been observed in vivo. The FeSSIF dissolution method provides results that more closely correlate with the observed in vivo results than the Sink Conditions dissolution method.

Example 4

Human Pharmacokinetic Study (Formulation C5-12)

A Phase 1, non-fasting, open-label, single-dose, two-arm, three-period, randomized, crossover study was conducted to evaluate the pharmacokinetics of Formulation C5-12 of Example 1 and several other formulations containing Compounds 1, 2, 3, and 4.

Methodology:

Formulation C5-12 and a second formulation were tested in Arm II of the study. Adult male and female subjects (N=30 for combined Arm I and Arm II studies) in general good health were selected to participate in the study according to the selection criteria. Subjects meeting the selection criteria were randomly assigned to one of the Regimen sequences as shown below in Table 4-A.

TABLE 4-A

| ARM | SEQUENCE NUMBER | NUMBER OF SUBJECTS | REGIMENS | | |
|---|---|---|---|---|---|
| | | | PERIOD 1 | PERIOD 2 | PERIOD 3 |
| II | 1 | 5 | A | * | B |
| | 2 | 5 | * | B | A |
| | 3 | 5 | B | A | * |

* Second formulation.

Study drug was administered as provided below in Table 4-B.

TABLE 4-B

| REGIMEN A (Reference Regimen) | One Single Tablet (i.e., Compound 4 250 mg immediate release tablet) + Two Triple Tablets (each co-formulated tablet contains Compound 1 (75 mg), Compound 2 (12.5 mg), and Compound 3 (50 mg)) are administered under non-fasting conditions in the morning and one Single Tablet is administered under non-fasting conditions in the evening (Day 1 of each period in Arm I and II). |
|---|---|
| REGIMEN B | Three Formulation C5-12 tablets (bi-layer tablet/total dose of Compound 1 (150 mg)/ Compound 2 (25 mg)/Compound 3 (100 mg)/ Compound 4 (600 mg)) are administered in the morning under non-fasting conditions (Day 1 of each period in Arm II). |

Each study regimen was taken orally with approximately 240 mL of water approximately 30 minutes after the start of standardized breakfast. Study regimens were administered orally in the morning on Study Day 1 of each period. For Regimen A the evening dose of the Single Tablet was taken orally with approximately 240 mL of water approximately 30 minutes after the start of the evening snack. Serial blood samples for pharmacokinetic analysis were collected 72 hours after dosing in each period.

Tables 4-C, 4-D, 4-E, and 4-F below below report the Arm II pharmacokinetic data for Formulation C5-12 (separately reported for each of Compounds 1, 2, 3, and 4). Table 4-G presents the relative bioavailability and 90% confidence intervals results for the pharmacokinetic data of Formulation C5-12 relative to the reference regimen. The data presented in Tables 4-C through 4-G are preliminary data and are subject to database lock and final data verification.

Arm II Pharmacokinetic Data (C5-12):

TABLE 4-C

Compound 1 Pharmacokinetic Data (C5-12)

| | GEOMETRIC MEAN (ARITHMETIC MEAN, % CV) (N = 13) | |
|---|---|---|
| PARAMETER (UNIT) | REGIMEN A (REFERENCE REGIMEN) | REGIMEN E (C5-12) |
| $C_{max}$ (ng/mL) | 900 (1340, 100) | 647 (1050, 96) |
| $T_{max}$ (h) | 4.8 (30) | 5.7 (47) |
| $t_{1/2}$ (h) | 5.2 (16) | 5.1 (20) |
| $AUC_t$ (ng · h/mL) | 4670 (6120, 79) | 4310 (5930, 82) |
| $AUC_\infty$ (ng · h/mL) | 4690 (6140, 79) | 4330 (5950, 81) |
| $C_{24}$ (ng/mL) | 24.3 (27.2, 53) | 24.5 (28.2, 60) |

TABLE 4-D

Compound 2 Pharmacokinetic Data (C5-12)

| PARAMETER (UNIT) | REGIMEN A (REFERENCE REGIMEN) GEOMETRIC MEAN (ARITHMETIC MEAN, % CV) (N = 13) | REGIMEN E (C5-12) |
|---|---|---|
| $C_{max}$ (ng/mL) | 113 (117, 27) | 117 (122, 31) |
| $T_{max}$ (h) | 4.5 (25) | 5.2 (18) |
| $t_{1/2}$ (h) | 26.6 (40) | 23.2 (35) |
| $AUC_t$ (ng·h/mL) | 1450 (1500, 24) | 1510 (1560, 25) |
| $AUC_\infty$ (ng·h/mL) | 1640 (1700, 28) | 1670 (1740, 29) |
| $C_{24}$ (ng/mL) | 17.9 (18.7, 29) | 18.7 (19.4, 29) |

TABLE 4-E

Compound 3 Pharmacokinetic Data (C5-12)

| PARAMETER (UNIT) | REGIMEN A (REFERENCE REGIMEN) GEOMETRIC MEAN (ARITHMETIC MEAN, % CV) (N = 13) | REGIMEN E (C5-12) |
|---|---|---|
| $C_{max}$ (ng/mL) | 1170 (1330, 57) | 1160 (1390, 57) |
| $T_{max}$ (h) | 4.0 (27) | 4.9 (35) |
| $t_{1/2}$ (h) | 4.9 (27) | 4.2 (26) |
| $AUC_t$ (ng·h/mL) | 7710 (8630, 51) | 8160 (9470, 54) |
| $AUC_\infty$ (ng·h/mL) | 7900 (8790, 50) | 8270 (9560, 53) |
| $C_{24}$ (ng/mL) | 37.0 (42.6, 55) | 38.8 (46.3, 62) |

TABLE 4-F

Compound 4 Pharmacokinetic Data (C5-12)

| PARAMETER (UNIT) | REGIMEN A (REFERENCE REGIMEN) GEOMETRIC MEAN (ARITHMETIC MEAN, % CV) (N = 13) | REGIMEN E (C5-12) |
|---|---|---|
| $C_{max}$ (ng/mL) | 1240 (1260, 22) | 1350 (1480, 46) |
| $T_{max}$ (h) | 3.1 (34) | 9.7 (39) |
| $t_{1/2}$ (h) | 5.5 (9) | 6.4 (19) |
| $AUC_t$ (ng·h/mL) | 18200 (18800, 26) | 18400 (20200, 47) |
| $AUC_\infty$ (ng·h/mL) | 18400 (18900, 26) | 18600 (20300, 47) |
| $C_{24}$ (ng/mL) | 361 (392, 42) | 290 (344, 64) |

TABLE 4-G

Relative Bioavailability and 90% Confidence Intervals (C5-12)

| PARAMETER | COMPOUND 1 | COMPOUND 2 | COMPOUND 3 | COMPOUND 4 |
|---|---|---|---|---|
| $C_{max}$ | 0.714[a] (0.482-1.056)[b] | 1.038 (0.933-1.155) | 1.001 (0.821-1.220) | 1.094 (0.856-1.398) |
| $AUC_{inf}$ | 0.919 (0.724-1.167) | 1.022 (0.963-1.084) | 1.056 (0.935-1.192) | 1.012 (0.832-1.231) |

[a]Point Estimate
[b]90% Confidence Interval

Arm III Pharmacokinetic Data (C5-12):

After completion of the Arm II study, an Arm III study was conducted to evaluate the steady-state pharmacokinetics of Formulation C5-12 in a 14-day multiple-dose, single period, randomized design (N=12). Three Formulation C5-12 tablets were administered under non-fasting conditions to subjects for 14 days (Study Days 1 through 14).

Tables 4-H, 4-I, 4-J, and 4-K below report the Arm III pharmacokinetic data for Formulation C5-12 (separately reported for each of Compounds 1, 2, 3, and 4). The data presented in Tables 4-H through 4-K are preliminary data and are subject to database lock and final data verification.

TABLE 4-H

Compound 1 Pharmacokinetic Data (C5-12)

| PARAMETER (UNIT) | DAY 1 GEOMETRIC MEAN (ARITHMETIC MEAN, % CV) (N = 14) | DAY 14 | RATIO |
|---|---|---|---|
| $AUC_{24}$ (ng·h/mL) | 4640 (6070, 64) | 10600 (15100, 88) | 2.28 |
| $C_{max}$ (ng/mL) | 651 (991, 77) | 1640 (2530, 95) | 2.52 |
| $C_{24}$ (ng/mL) | 33.7 (38.3, 56) | 33.7 (44.9, 103) | 1.00 |
| $T_{max}$ (h) | 6.7 (41) | 5.1 (27) | |
| $\beta$ (1/h) | — | 0.151 (19) | |
| $t_{1/2}$ (h) | — | 4.6 (19) | |

TABLE 4-I

Compound 2 Pharmacokinetic Data (C5-12)

| PARAMETER (UNIT) | DAY 1 GEOMETRIC MEAN (ARITHMETIC MEAN, % CV) (N = 14) | DAY 14 | RATIO |
|---|---|---|---|
| $AUC_{24}$ (ng·h/mL) | 1280 (1320, 26) | 1720 (1780, 26) | 1.34 |
| $C_{max}$ (ng/mL) | 123 (127, 28) | 135 (141, 34) | 1.10 |
| $C_{24}$ (ng/mL) | 23.4 (24.4, 30) | 40.2 (41.5, 24) | 1.72 |
| $T_{max}$ (h) | 5.5 (29) | 5.6 (18) | |
| $\beta$ (1/h) | — | 0.023 (41) | |
| $t_{1/2}$ (h) | — | 29.8 (43) | |

TABLE 4-J

Compound 3 Pharmacokinetic Data (C5-12)

| PARAMETER (UNIT) | DAY 1 GEOMETRIC MEAN (ARITHMETIC MEAN, % CV) (N = 14) | DAY 14 | RATIO |
|---|---|---|---|
| $AUC_{24}$ (ng·h/mL) | 7230 (7970, 41) | 10700 (11200, 29) | 1.48 |
| $C_{max}$ (ng/mL) | 921 (1030, 44) | 1430 (1500, 28) | 1.55 |
| $C_{24}$ (ng/mL) | 34.7 (41.1, 53) | 40.0 (42.3, 36) | 1.15 |
| $T_{max}$ (h) | 5.4 (38) | 4.7 (17) | |
| $\beta$ (1/h) | — | 0.174 (23) | |
| $t_{1/2}$ (h) | — | 4.0 (23) | |

TABLE 4-K

Compound 4 Pharmacokinetic Data (C5-12)

| PARAMETER (UNIT) | DAY 1 GEOMETRIC MEAN (ARITHMETIC MEAN, % CV) (N = 14) | DAY 14 | RATIO |
|---|---|---|---|
| $AUC_{24}$ (ng·h/mL) | 13600 (15500, 50) | 12000 (13900, 50) | 0.88 |
| $C_{max}$ (ng/mL) | 1320 (1480, 44) | 1250 (1400, 44) | 0.95 |
| $C_{24}$ (ng/mL) | 272 (313, 55) | 172 (210, 61) | 0.63 |
| $T_{max}$ (h) | 9.0 (20) | 9.4 (19) | |
| $\beta$ (1/h) | — | 0.117 (22) | |
| $t_{1/2}$ (h) | — | 5.9 (22) | |

Example 5

Human Pharmacokinetic Study (Formulation C5-12)

A Phase 1, non-fasting, open-label, two-arm, four-period, randomized, crossover study was conducted to compare and characterize the pharmacokinetics of (i) Triple Tablet when co-administered with Single Tablet, and (ii) Formulation C5-12 as discussed below. Part 1 was a single dose, two-treatment, randomized, four period, two sequence replicated crossover study with 88 subjects. Doses in the four periods were separated by at least 10 days. Part 2 was a multiple-dose, two-treatment, two period, randomized crossover study with 66 subjects. Dosing in each period was 14 days and doses in the two periods were separated by at least 10 days.

Methodology:

Adult male and female subjects in general good health were selected to participate in the study according to the selection criteria. Subjects meeting the selection criteria were randomly assigned to one of the sequences of Regimens A and B (four sequences for Arm I and two sequences for Arm II) as shown below in Table 5-A.

TABLE 5-A

| ARM | N | REGIMENS | | | |
|---|---|---|---|---|---|
| | | PERIOD 1 | PERIOD 2 | PERIOD 3 | PERIOD 4 |
| I | 44 | A | B | A | B |
| | 44 | B | A | B | A |
| II | 33 | A | B | | |
| | 33 | B | A | | |

Study drug was administered as provided below in Table 5-B.

TABLE 5-B

| | |
|---|---|
| REGIMEN A (Test Regimen) | Three Film-Coated Formulation C5-12 tablets (total dose of Compound 1 (150 mg)/Compound 2 (25 mg)/Compound 3 (100 mg)/Compound 4 (600 mg)) were administered in the morning under non-fasting conditions on Day 1 of each corresponding period in Arm I, and Days 1 through 14 of each corresponding period in Arm II. |
| REGIMEN B (Reference Regimen) | One Single Tablet (i.e., Compound 4 250 mg immediate release tablet) + Two Triple Tablets (each co-formulated tablet contains Compound 1 (75 mg), Compound 2 (12.5 mg), and Compound 3 (50 mg)) are administered under non-fasting conditions in the morning and one Single Tablet is administered under non-fasting conditions in the evening on Day 1 of each corresponding period in Arm I, and Days 1 through 14 of each corresponding period in Arm II. |

Each study regimen was taken orally with approximately 240 mL of water approximately 30 minutes after the start of standardized breakfast. Study regimens were administered orally in the morning on Study Day 1 of each period. Serial blood samples for pharmacokinetic analysis were collected 72 hours after dosing in each period.

Arm I Pharmacokinetic Data (Single Dose Study):

Tables 5-C, 5-D, 5-E, and 5-F below report the Arm I pharmacokinetic data for Formulation C5-12 (separately reported for each of Compounds 1, 2, 3, and 4). Table 5-G presents the results of a relative bioavailability and 90% confidence interval analysis of the pharmacokinetic data for Formulation C5-12 relative to the reference regimen. The data presented in Tables 5-C through 5-G are preliminary data and are subject to database lock and final data verification by the statistician.

TABLE 5-C

Compound 1 Pharmacokinetic Data (Arm I: C5-12)

| | GEOMETRIC MEAN (ARITHMETIC MEAN, % CV) | |
|---|---|---|
| PARAMETER (UNIT) | REGIMEN A (C5-12) (N = 172) | REGIMEN B (REFERENCE REGIMEN) N = 171 |
| $C_{max}$ (ng/mL) | 618 (996, 97) | 935 (1360, 82) |
| $T_{max}$ (h) | 5.0 (5.8, 32) | 5.0 (5.1, 27) |
| $t_{1/2}$ (h) | 6.15 (1.46) | 6.02 (1.36) |
| $AUC_t$ (ng·h/mL) | 4460 (6450, 86) | 5470 (7170, 75) |
| $AUC_\infty$ (ng·h/mL) | 4490 (6480, 85) | 5490 (7270, 74) |

TABLE 5-D

Compound 2 Pharmacokinetic Data (Arm I: C5-12)

| | GEOMETRIC MEAN (ARITHMETIC MEAN, % CV) | |
|---|---|---|
| PARAMETER (UNIT) | REGIMEN A (C5-12) (N = 172) | REGIMEN B (REFERENCE REGIMEN) (N = 171) |
| $C_{max}$ (ng/mL) | 124 (133, 33) | 131 (136, 33) |
| $T_{max}$ (h) | 5.0 (5.3, 17) | 5.0 (5.1, 15) |
| $t_{1/2}$ (h) | 37.9 (15.3) | 39.2 (14.2) |
| $AUC_t$ (ng·h/mL) | 1660 (1770, 32) | 1630 (1680, 31) |
| $AUC_\infty$ (ng·h/mL) | 1800 (1910, 33) | 1760 (1840, 30) |

TABLE 5-E

Compound 3 Pharmacokinetic Data (Arm I: C5-12)

| | GEOMETRIC MEAN (ARITHMETIC MEAN, % CV) | |
|---|---|---|
| PARAMETER (UNIT) | REGIMEN A (C5-12) (N = 172) | REGIMEN B (REFERENCE REGIMEN) (N = 171) |
| $C_{max}$ (ng/mL) | 1130 (1320, 48) | 1430 (1540, 42) |
| $T_{max}$ (h) | 4.0 (4.9, 32) | 4.0 (4.5, 23) |
| $t_{1/2}$ (h) | 4.52 (0.99) | 4.47 (0.86) |
| $AUC_t$ (ng·h/mL) | 7450 (9140, 61) | 8610 (9690, 58) |
| $AUC_\infty$ (ng·h/mL) | 8090 (9360, 59) | 8750 (9920, 56) |

TABLE 5-F

Compound 4 Pharmacokinetic Data (Arm I: C5-12)

| | GEOMETRIC MEAN (ARITHMETIC MEAN, % CV) | |
|---|---|---|
| PARAMETER (UNIT) | REGIMEN A (C5-12) (N = 172) | REGIMEN B (REFERENCE REGIMEN) (N = 171) |
| $C_{max}$ (ng/mL) | 1060 (1210, 46) | 1030 (1110, 36) |
| $T_{max}$ (h) | 8.0 (8.4, 32) | 4.0 (4.2, 28) |
| $t_{1/2}$ (h) | 6.91 (1.99) | 5.80 (1.17) |
| $AUC_t$ (ng·h/mL) | 12700 (15200, 54) | 14800 (15900, 38) |
| $AUC_\infty$ (ng·h/mL) | 12900 (15300, 54) | 14900 (16100, 38) |

TABLE 5-G

Relative Bioavailability and 90% Confidence Intervals (Arm I: C5-12)

| REGIMEN | PARAMETER | POINT ESTIMATE | 90% CONFIDENCE INTERVAL |
|---|---|---|---|
| | COMPOUND 1 | | |
| A vs. B | $C_{max}$ | 0.685 | 0.625-0.750 |
| | | 0.689 | 0.091 |
| | $AUC_t$ | 0.849 | 0.790-0.911 |
| | $AUC_{inf}$ | 0.850 | 0.792-0.912 |
| | COMPOUND 2 | | |
| A vs. B | $C_{max}$ | 0.960 | 0.926-0.995 |
| | AUCt | 1.037 | 1.011-1.064 |
| | $AUC_{24}$ | 1.035 | 1.009-1.062 |
| | COMPOUND 3 | | |
| A vs. B | $C_{max}$ | 0.821 | 0.777-0.867 |
| | AUCt | 0.914 | 0.880-0.949 |
| | $AUC_{24}$ | 0.923 | 0.893-0.953 |
| | COMPOUND 4 | | |
| A vs. B | $C_{max}$ | 1.032 | 0.950-1.121 |
| | AUCt | 0.859 | 0.787-0.936 |
| | $AUC_{24}$ | 0.863 | 0.793-0.939 |

Arm II Pharmacokinetic Data (Multiple Dose Study):

Tables 5-H, 5-I, 5-J, and 5-K below report the Arm II pharmacokinetic data for Formulation C5-12 (separately reported for each of Compounds 1, 2, 3, and 4). Table 5-L presents the results of a relative bioavailability and 90% confidence interval analysis of the pharmacokinetic data for Formulation C5-12 relative to the reference regimen. The data presented in Tables 5-H through 5-L are preliminary data and are subject to database lock and final data verification by the statistician.

TABLE 5-H

Compound 1 Pharmacokinetic Data (Arm II: C5-12)

| PARAMETER (UNIT) | GEOMETRIC MEAN (ARITHMETIC MEAN, % CV) (N = 63) | |
|---|---|---|
| | REGIMEN A (C5-12) | REGIMEN B (REFERENCE REGIMEN) |
| $AUC_{24}$ (ng·h/mL) | 8900 (13500, 96) | 9240 (13200, 82) |
| $C_{max}$ (ng/mL) | 1500 (2290, 86) | 1947 (2810, 85) |
| $T_{max}$ (h) | 5.0 (5.2, 30) | 4.0 (4.2, 22) |
| $C_{24}$ (ng/mL) | 34.6 (54.2, 141) | 30.4 (38.9, 73) |
| $\beta$ (1/h) | 0.129 (0.132, 20) | 0.128 (0.130, 17) |
| $t_{1/2}$ (h) | 5.2 (20) | 5.3 (17) |

TABLE 5-I

Compound 2 Pharmacokinetic Data (Arm II: C5-12)

| PARAMETER (UNIT) | GEOMETRIC MEAN (ARITHMETIC MEAN, % CV) (N = 63) | |
|---|---|---|
| | REGIMEN A (C5-12) | REGIMEN B (REFERENCE REGIMEN) |
| $AUC_{24}$ (ng·h/mL) | 1390 (1470, 34) | 1240 (1330, 37) |
| $C_{max}$ (ng/mL) | 128 (135, 31) | 117 (127, 35) |
| $T_{max}$ (h) | 5.0 (5.0, 11) | 5.0 (4.8, 18) |
| $C_{24}$ (ng/mL) | 30.5 (33.5, 46) | 26.6 (29.6, 49) |
| $\beta$ (1/h) | 0.019 (0.020, 34) | 0.019 (0.020, 34) |
| $t_{1/2}$ (h) | 35.1 (34) | 35.0 (34) |

TABLE 5-J

Compound 3 Pharmacokinetic Data (Arm II: C5-12)

| PARAMETER (UNIT) | GEOMETRIC MEAN (ARITHMETIC MEAN, % CV) (N = 63) | |
|---|---|---|
| | REGIMEN A (C5-12) | REGIMEN B (REFERENCE REGIMEN) |
| $AUC_{24}$ (ng·h/mL) | 8670 (9470, 43) | 9580 (10700, 50) |
| $C_{max}$ (ng/mL) | 1340 (1440, 39) | 1680 (1800, 44) |
| $T_{max}$ (h) | 4.0 (4.6, 21) | 4.0 (4.1, 19) |
| $C_{24}$ (ng/mL) | 36.2 (44.3, 76) | 35.1 (43.2, 73) |
| $\beta$ (1/h) | 0.147 (0.152, 25) | 0.142 (0.145, 23) |
| $t_{1/2}$ (h) | 4.6 (25) | 4.8 (23) |

TABLE 5-K

Compound 4 Pharmacokinetic Data (Arm II: C5-12)

| PARAMETER (UNIT) | GEOMETRIC MEAN (ARITHMETIC MEAN, % CV) (N = 63) | |
|---|---|---|
| | REGIMEN A (C5-12) | REGIMEN B (REFERENCE REGIMEN) |
| $AUC_{24}$ (ng·h/mL) | 8810 (10300, 55) | 9770 (10600, 42) |
| $C_{max}$ (ng/mL) | 799 (896, 46) | 879 (932, 40) |
| $T_{max}$ (h) | 8.0 (8.4, 35) | 4.0 (5.2, 79) |
| $C_{24}$ (ng/mL) | 116 (155, 87) | 162 (183, 55) |
| $\beta$ (1/h) | 0.104 (0.111, 30) | 0.122 (0.127, 44) |
| $t_{1/2}$ (h) | 6.2 (30) | 5.5 (24) |

TABLE 5-L

Relative Bioavailability and 90% Confidence Intervals (Arm II: C5-12)

| REGIMEN | PARAMETER | POINT ESTIMATE | 90% CONFIDENCE INTERVAL |
|---|---|---|---|
| | COMPOUND 1 | | |
| A vs. B | $C_{max}$ | 0.727 | 0.642-0.823 |
| | $AUC_{24}$ | 0.903 | 0.817-0.998 |
| | $C_{24}$ | 1.055 | 0.970-1.147 |
| | COMPOUND 2 | | |
| A vs. B | $C_{max}$ | 1.087 | 1.006-1.174 |
| | AUCt | 1.091 | 1.065-1.119 |
| | $AUC_{24}$ | 1.098 | 1.064-1.132 |
| | COMPOUND 3 | | |
| A vs. B | $C_{max}$ | 0.793 | 0.747-0.843 |
| | AUCt | 0.894 | 0.847-0.944 |
| | $AUC_{24}$ | 1.009 | 0.946-1.075 |
| | COMPOUND 4 | | |
| A vs. B | $C_{max}$ | 0.905 | 0.823-0.995 |
| | AUCt | 0.893 | 0.810-0.986 |
| | $AUC_{24}$ | 0.710 | 0.622-0.812 |

With respect to the observed pharmacokinetics of Formulation C5-12 relative to the reference regimen in Arm I of the study:

(1) $C_{max}$ for Compound 1 was lower (by 30%) than $C_{max}$ for the reference regimen. Otherwise, the exposures for Compound 1, Compound 2, Compound 3, and Compound 4 were comparable (less than 20% difference) to exposures from the reference regimen. Based on the exposures-efficacy of Compound 1, Compound 2, and Compound 3, however, these differences were not deemed clinically significant.

(2) For the AUC of Compound 4 and Compound 1 and the $C_{max}$ of Compound 3, the lower 90% confidence bounds were slightly lower than 0.80 (less than 2% difference) and the geometric mean exposures were within 20% of the exposures from the reference regimen. These differences were not deemed clinically significant.

With respect to the observed pharmacokinetics of Formulation C5-12 relative to the reference regimen in Arm II of the study:

(1) Compound 1 and Compound 3 exposures ($C_{24,ss}$ and $AUC_{24,ss}$) were bioequivalent (point estimate and 90% confidence interval for the geometric mean ratio ("GMR") within 0.80-1.25) to exposures from the reference regimen except for $C_{max,ss}$, which was lower (by 27% and 21%, respectively) than $C_{max,ss}$ for the reference regimen. Based on the exposures-efficacy, however, the difference in $C_{max,ss}$ was not deemed clinically significant.

(2) Compound 2 exposures were bioequivalent (point estimate and 90% confidence interval for the GMR within 0.80-1.25) to exposures from the reference regimen.

(3) Compound 4 exposures ($C_{max,ss}$ and $AUC_{24,ss}$) were bioequivalent (point estimate and 90% confidence interval for the GMR within 0.80-1.25) to exposures from the reference regimen except for the $C_{24,ss}$ ($C_{trough}$) which was lower (by 29%) than the $C_{24,ss}$ ($C_{trough}$) for the reference regimen. Based on the exposures-efficacy, however, the difference in $C_{trough}$ was not deemed clinically significant.

It should be understood that the above-described embodiments and the examples are given by way of illustration, not limitation. Various changes and modifications within the scope of the present invention will become apparent to those skilled in the art from the present description.

All references (patent and non-patent) cited above are incorporated by reference into this patent disclosure. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A solid dosage form comprising a first composition and a second composition, wherein:

the first composition comprises 50 mg of (Compound 1)

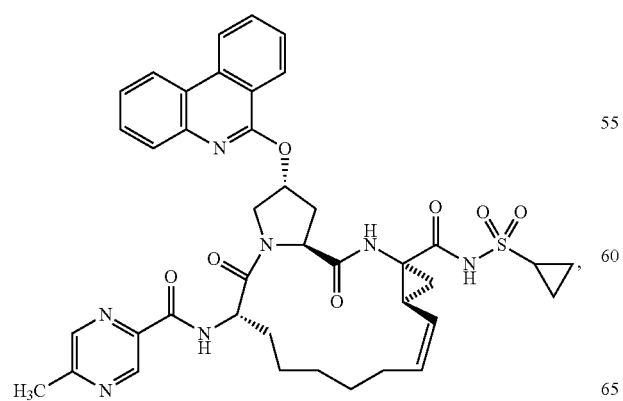

8.33 mg of (Compound 2)

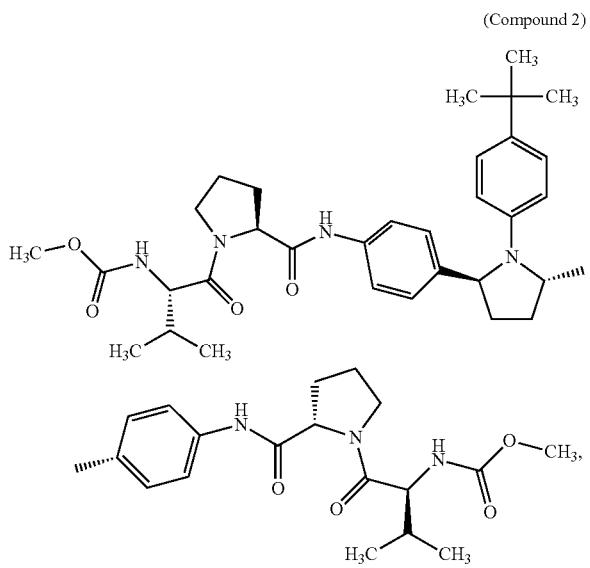

33.33 mg of ritonavir, 70-85% by weight of copovidone; and 5% to 10% by weight of a pharmaceutically acceptable surfactant or a combination of pharmaceutically acceptable surfactants, wherein all percentages are weight percentages relative to the total weight of the first composition, and wherein Compound 1, Compound 2 and ritonavir are formulated in amorphous solid dispersion;

the second composition comprises 216.2 mg sodium monohydrate salt of (Compound 4)

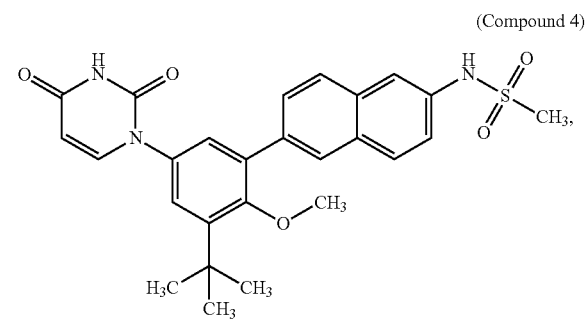 [SMILES: COc1c(-c2ccc3cc(NS(C)(=O)=O)ccc3c2)cc(-n2ccc(=O)[nH]c2=O)cc1C(C)(C)C]

20-40% copovidone, and 20-40% hypromellose, wherein all percentages are weight percentages relative to the total weight of the second composition;

when dissolved in 900 mL of a dissolution medium using a standard USP dissolution Apparatus 2 (paddle) operating at 100 RPM at 37° C., 50-60% Compound 1 in the solid dosage form is released within 1 hour, 50-60% Compound 2 in the solid dosage form is released within 1 hour, 50-60% ritonavir in the solid dosage form is released within 1 hour, and 0.5-2% Compound 4 in the solid dosage form is released within 1 hour, wherein the dissolution medium is 0.05 M sodium phosphate buffer (pH 6.8) with 15 mM cetyltrimethylammonium bromide (cTAB), and the total weight of the solid dosage form is 1200-1400 mg.

2. A method for treating hepatitis C virus (HCV) infection in a patient in need of such treatment, wherein the method comprises administering once daily to the patient at least one solid dosage form of claim 1.

3. A method for treating HCV infection in a patient in need of such treatment, wherein the method comprises administering once daily to the patient three solid dosage forms of claim 1.

4. A solid dosage form comprising a first composition and a second composition, wherein:
- the first composition comprises 50 mg of Compound 1, 8.33 mg of Compound 2, 33.33 mg of ritonavir, 70-85% by weight of copovidone; and 5% to 10% by weight of a pharmaceutically acceptable surfactant or a combination of pharmaceutically acceptable surfactants, wherein all percentages are weight percentages relative to the total weight of the first composition, and wherein Compound 1, Compound 2 and ritonavir are formulated in amorphous solid dispersion;
- the second composition comprises 216.2 mg sodium monohydrate salt of Compound 4, 20-40% copovidone, and 20-40% hypromellose, wherein all percentages are weight percentages relative to the total weight of the second composition;
- when dissolved in 900 mL of a dissolution medium using a standard USP dissolution Apparatus 2 (paddle) operating at 100 RPM at 37° C., 95-100% Compound 1 in the solid dosage form is released within 4 hours, 95-100% Compound 2 in the solid dosage form is released within 4 hours, 95-100% ritonavir in the solid dosage form is released within 4 hours, and 10-15% Compound 4 in the solid dosage form is released within 4 hours, wherein the dissolution medium is 0.05 M sodium phosphate buffer (pH 6.8) with 15 mM cTAB, and
- the total weight of the solid dosage form is 1200-1400 mg.

5. A method for treating HCV infection in a patient in need of such treatment, wherein the method comprises administering once daily to the patient at least one solid dosage form of claim 4.

6. A method for treating HCV infection in a patient in need of such treatment, wherein the method comprises administering once daily to the patient three solid dosage forms of claim 4.

7. A solid dosage form comprising a first composition and a second composition, wherein:
- the first composition comprises 50 mg of Compound 1, 8.33 mg of Compound 2, 33.33 mg of ritonavir, 70-85% by weight of copovidone; and 5% to 10% by weight of a pharmaceutically acceptable surfactant or a combination of pharmaceutically acceptable surfactants, wherein all percentages are weight percentages relative to the total weight of the first composition, and wherein Compound 1, Compound 2 and ritonavir are formulated in amorphous solid dispersion;
- the second composition comprises 216.2 mg sodium monohydrate salt of Compound 4, 20-40% copovidone, and 20-40% hypromellose, wherein all percentages are weight percentages relative to the total weight of the second composition;
- when dissolved in 900 mL of a dissolution medium using a standard USP dissolution Apparatus 2 (paddle) operating at 100 RPM at 37° C., 95-100% Compound 1 in the solid dosage form is released within 6 hours, 95-100% Compound 2 in the solid dosage form is released within 6 hours, 95-100% ritonavir in the solid dosage form is released within 6 hours, and 15-20% Compound 4 in the solid dosage form is released within 6 hours, wherein the dissolution medium is 0.05 M sodium phosphate buffer (pH 6.8) with 15 mM cTAB, and
- the total weight of the solid dosage form is 1200-1400 mg.

8. A method for treating HCV infection in a patient in need of such treatment, wherein the method comprises administering once daily to the patient at least one solid dosage form of claim 7.

9. A method for treating HCV infection in a patient in need of such treatment, wherein the method comprises administering once daily to the patient three solid dosage forms of claim 7.

10. A solid dosage form comprising a first composition and a second composition, wherein:
- the first composition comprises 50 mg of Compound 1, 8.33 mg of Compound 2, 33.33 mg of ritonavir, 70-85% by weight of copovidone; and 5% to 10% by weight of a pharmaceutically acceptable surfactant or a combination of pharmaceutically acceptable surfactants, wherein all percentages are weight percentages relative to the total weight of the first composition, and wherein Compound 1, Compound 2 and ritonavir are formulated in amorphous solid dispersion;
- the second composition comprises 216.2 mg sodium monohydrate salt of Compound 4, 20-40% copovidone, and 20-40% hypromellose, wherein all percentages are weight percentages relative to the total weight of the second composition;
- when dissolved in 900 mL of a dissolution medium using a standard USP dissolution Apparatus 2 (paddle) operating at 100 RPM at 37° C., 100% Compound 1 in the solid dosage form is released within 8 hours, 100% Compound 2 in the solid dosage form is released within 8 hours, 100% ritonavir in the solid dosage form is released within 8 hours, 20-30% Compound 4 in the solid dosage form is released within 8 hours, 30-40% Compound 4 in the solid dosage form is released within 12 hours, and 40-60% Compound 4 in the solid dosage form is released within 16 hours, wherein the dissolution medium is 0.05 M sodium phosphate buffer (pH 6.8) with 15 mM cTAB, and
- the total weight of the solid dosage form is 1200-1400 mg.

11. A method for treating HCV infection in a patient in need of such treatment, wherein the method comprises administering once daily to the patient at least one solid dosage form of claim 10.

12. A method for treating HCV infection in a patient in need of such treatment, wherein the method comprises administering once daily to the patient three solid dosage forms of claim 10.

13. A solid dosage form comprising a first composition and a second composition, wherein:
- the first composition comprises 50 mg of Compound 1, 8.33 mg of Compound 2, 33.33 mg of ritonavir, 70-85% by weight of copovidone; and 5% to 10% by weight of a pharmaceutically acceptable surfactant or a combination of pharmaceutically acceptable surfactants, wherein all percentages are weight percentages relative to the total weight of the first composition, and wherein Compound 1, Compound 2 and ritonavir are formulated in amorphous solid dispersion;
- the second composition comprises 216.2 mg sodium monohydrate salt of Compound 4, 20-40% copovidone, and 20-40% hypromellose, wherein all percentages are weight percentages relative to the total weight of the second composition;
- when dissolved in 900 mL of a dissolution medium using a standard USP dissolution Apparatus 2 (paddle) operating at 100 RPM at 37° C., 100% Compound 1 in the solid dosage form is released within 8 hours, 100% Compound 2 in the solid dosage form is released within 8 hours, 100% ritonavir in the solid dosage form is released within 8 hours, 20-30% Compound 4 in the solid dosage form is released within 8 hours, 30-40% Compound 4 in the solid dosage form is released within 12 hours, 40-60% Compound 4 in the solid dosage form is released within 16 hours, and 60-80% Compound 4 in the solid dosage form is released within 24 hours, wherein the dissolution medium is 0.05 M sodium phosphate buffer (pH 6.8) with 15 mM cTAB, and the total weight of the solid dosage form is 1200-1400 mg.

14. A method for treating HCV infection in a patient in need of such treatment, wherein the method comprises administering once daily to the patient at least one solid dosage form of claim 13.

15. A method for treating HCV infection in a patient in need of such treatment, wherein the method comprises administering once daily to the patient three solid dosage forms of claim 13.

\* \* \* \* \*

UNITED STATES PATENT AND TRADEMARK OFFICE
CERTIFICATE OF CORRECTION

PATENT NO. : 9,333,204 B2
APPLICATION NO. : 14/677611
DATED : May 10, 2016
INVENTOR(S) : Jonathan M. Miller et al.

Page 1 of 1

It is certified that error appears in the above-identified patent and that said Letters Patent is hereby corrected as shown below:

On the Title Page

Item (72) Inventors should read:
Jonathan M. Miller, Lindhurst, IL (US); John B. Morris, Grayslake, IL (US); Nancy E. Sever, Northbrook, IL (US); Eric A. Schmitt, Libertyville, IL (US); Ping X. Gao, Highland Park, IL (US); Yi Shi, Libertyville, IL (US); Yi Gao, Vernon Hills, IL (US); Bernd Liepold, Dossenheim (DE); Anna Moosmann, Winterbach (DE); Mirko Pauli, Ludwigshafen (DE); Fatih Durak, Ludwigshafen (DE); Thomas Kessler, Schifferstadt (DE); Peter A. Hoelig, Waechtersbach (DE); Karin Rosenblatt, Mannheim (DE); Drazen Kostelac, Mannheim (DE); Rajeev Gokhale, Singapore (SG); Mark Costello, Chicago, IL (US); Carl Knable, Elmhurst, IL (US); Susan George, Waukegan, IL (US).

Signed and Sealed this
Fourth Day of February, 2025

Coke Morgan Stewart
*Acting Director of the United States Patent and Trademark Office*